United States Patent
Lian

(10) Patent No.: US 11,202,789 B2
(45) Date of Patent: Dec. 21, 2021

(54) METHOD OF TREATING GLYCOGEN STORAGE DISEASE

(71) Applicant: Viking Therapeutics, Inc., San Diego, CA (US)

(72) Inventor: Brian Lian, Rancho Santa Fe, CA (US)

(73) Assignee: Viking Therapeutics, Inc., San Diego, CA (US)

( * ) Notice: Subject to any disclaimer, the term of this patent is extended or adjusted under 35 U.S.C. 154(b) by 0 days.

(21) Appl. No.: 16/462,515

(22) PCT Filed: Nov. 17, 2017

(86) PCT No.: PCT/US2017/062393
§ 371 (c)(1),
(2) Date: May 20, 2019

(87) PCT Pub. No.: WO2018/094265
PCT Pub. Date: May 24, 2018

(65) Prior Publication Data
US 2019/0343850 A1    Nov. 14, 2019

Related U.S. Application Data

(60) Provisional application No. 62/456,610, filed on Feb. 8, 2017, provisional application No. 62/425,007, filed on Nov. 21, 2016.

(51) Int. Cl.
*A61K 31/665* (2006.01)
*A61K 31/662* (2006.01)
(Continued)

(52) U.S. Cl.
CPC .......... *A61K 31/665* (2013.01); *A61K 31/662* (2013.01); *A61K 31/683* (2013.01);
(Continued)

(58) Field of Classification Search
CPC .. A61K 31/662; A61K 31/665; A61K 31/683; A61K 45/06; A61P 1/16;
(Continued)

(56) References Cited

U.S. PATENT DOCUMENTS 3,120,551 A    2/1964   Goldschmidt et al.
3,357,887 A    12/1967  Kagan et al.
(Continued)

FOREIGN PATENT DOCUMENTS

CN   107469086 A   12/2017
EP   0 580 550     1/1994
(Continued)

OTHER PUBLICATIONS

Austin ( May 1, 2016, Glycogen Storage disease, The patient-parent Handbook).*

(Continued)

*Primary Examiner* — Savitha M Rao
(74) *Attorney, Agent, or Firm* — Knobbe, Martens, Olson & Bear LLP

(57) ABSTRACT

The present disclosure provides methods and compositions for the treatment of hepatic symptoms of glycogen storage diseases through the administration of thyroid hormone receptor agonists. The methods and compositions provided herein are useful in the treatment of hyperlipidemia, hypercholesterolemia, hepatic steatosis, cardiomegaly, hepatomegaly, hepatic fibrosis, and cirrhosis associated with glycogen storage diseases (GSD) and defects of glycogen metabolism. Said compounds may also be useful in the prevention of GSD-related hepatocellular adenoma and hepatocellular carcinoma.

13 Claims, 20 Drawing Sheets

(51) Int. Cl.
  *A61K 31/683* (2006.01)
  *A61K 45/06* (2006.01)
  *A61P 9/00* (2006.01)
  *A61P 43/00* (2006.01)
  *A61P 41/00* (2006.01)
  *A61P 3/10* (2006.01)
  *A61P 3/08* (2006.01)
  *A61P 1/16* (2006.01)
  *A61P 3/06* (2006.01)
  *A61P 35/00* (2006.01)
  *A61P 3/04* (2006.01)

(52) U.S. Cl.
  CPC .............. *A61K 45/06* (2013.01); *A61P 1/16* (2018.01); *A61P 3/04* (2018.01); *A61P 3/06* (2018.01); *A61P 3/08* (2018.01); *A61P 3/10* (2018.01); *A61P 9/00* (2018.01); *A61P 35/00* (2018.01); *A61P 41/00* (2018.01); *A61P 43/00* (2018.01)

(58) Field of Classification Search
  CPC .... A61P 35/00; A61P 3/04; A61P 3/06; A61P 3/08; A61P 3/10; A61P 41/00; A61P 43/00; A61P 9/00
  See application file for complete search history.

(56) References Cited

U.S. PATENT DOCUMENTS

| | | |
|---|---|---|
| 4,069,343 A | 1/1978 | Sellstedt et al. |
| 4,069,347 A | 1/1978 | McCarthy et al. |
| 4,423,227 A | 12/1983 | Batz et al. |
| 4,426,453 A | 1/1984 | Cree et al. |
| 4,554,290 A | 11/1985 | Boger et al. |
| 4,673,691 A | 6/1987 | Bachynsky |
| 4,766,121 A | 8/1988 | Ellis et al. |
| 4,826,876 A | 5/1989 | Ellis et al. |
| 4,910,305 A | 3/1990 | Ellis et al. |
| 5,061,798 A | 10/1991 | Emmett et al. |
| 5,116,828 A | 5/1992 | Miura et al. |
| 5,158,978 A | 10/1992 | Rubin |
| 5,232,946 A | 8/1993 | Hurnaus et al. |
| 5,284,971 A | 2/1994 | Walker et al. |
| 5,324,522 A | 6/1994 | Krenning et al. |
| 5,401,772 A | 3/1995 | Yokoyama et al. |
| 5,519,163 A | 5/1996 | Gibbs et al. |
| 5,569,674 A | 10/1996 | Yokoyama et al. |
| 5,571,840 A | 11/1996 | Mayor et al. |
| 5,627,173 A | 5/1997 | Graeve et al. |
| 5,654,468 A | 8/1997 | Yokoyama et al. |
| 5,663,159 A | 9/1997 | Starrett, Jr. et al. |
| 5,741,803 A | 4/1998 | Pool et al. |
| 5,753,254 A | 5/1998 | Khan et al. |
| 5,854,282 A | 12/1998 | Mellin |
| 5,883,294 A | 3/1999 | Scanlan et al. |
| 5,922,775 A | 7/1999 | Kun et al. |
| 5,951,989 A | 9/1999 | Heymann |
| 6,107,517 A | 8/2000 | Scanlan et al. |
| 6,117,873 A | 9/2000 | Acklin et al. |
| 6,147,061 A | 11/2000 | Reiter |
| 6,194,454 B1 | 2/2001 | Dow |
| 6,221,911 B1 | 4/2001 | Lavin et al. |
| 6,236,946 B1 | 5/2001 | Scanlan et al. |
| 6,266,622 B1 | 7/2001 | Scanlan et al. |
| 6,326,398 B1 | 12/2001 | Chiang et al. |
| 6,344,481 B1 | 2/2002 | Cornelius et al. |
| 6,361,992 B1 | 3/2002 | Szkudlinski et al. |
| 6,380,255 B1 | 4/2002 | Lavin et al. |
| 6,414,002 B1 | 7/2002 | Cheng et al. |
| 6,414,026 B1 | 7/2002 | Billingham |
| 6,441,015 B2 | 8/2002 | Aspnes et al. |
| 6,465,687 B1 | 10/2002 | Li et al. |
| 6,468,755 B1 | 10/2002 | Shoelson |
| 6,492,424 B1 | 12/2002 | Apelqvist et al. |
| 6,495,533 B1 | 12/2002 | Matsui et al. |
| 6,534,676 B2 | 3/2003 | Markin et al. |
| 6,545,015 B2 | 4/2003 | Cheng et al. |
| 6,545,018 B2 | 4/2003 | Chiang et al. |
| 6,555,582 B1 | 4/2003 | Schwartz et al. |
| 6,566,372 B1 | 5/2003 | Zhi et al. |
| 6,576,636 B2 | 6/2003 | Webb et al. |
| 6,608,049 B2 | 8/2003 | Waltering et al. |
| 6,620,830 B2 | 9/2003 | Chiang |
| 6,625,201 B1 | 9/2003 | Wang et al. |
| 6,664,291 B2 | 12/2003 | Chiang et al. |
| 6,673,815 B2 | 1/2004 | Devasthale et al. |
| 6,680,340 B2 | 1/2004 | Cheng et al. |
| 6,689,896 B2 | 2/2004 | Kukkola |
| 6,716,877 B2 | 4/2004 | Markin |
| 6,723,744 B2 | 4/2004 | Aspnes et al. |
| 6,727,271 B2 | 4/2004 | Cheng et al. |
| 6,747,048 B2 | 6/2004 | Zhang et al. |
| 6,787,652 B1 | 9/2004 | Dow et al. |
| 6,794,406 B2 | 9/2004 | Haning et al. |
| 6,806,381 B2 | 10/2004 | Chidambaram et al. |
| 6,825,201 B2 | 11/2004 | Wang et al. |
| 6,831,102 B2 | 12/2004 | Rangeland |
| 6,852,706 B1 | 2/2005 | Heber-Katz |
| 6,875,782 B2 | 4/2005 | Cheng et al. |
| 6,982,348 B2 | 1/2006 | Kori et al. |
| 7,015,246 B2 | 3/2006 | Schmeck et al. |
| 7,402,602 B2 | 7/2008 | Bigg et al. |
| 7,514,419 B2 | 4/2009 | Erion et al. |
| 7,799,782 B2 | 9/2010 | Munson et al. |
| 7,829,552 B2 | 11/2010 | Erion et al. |
| 10,130,643 B2 | 11/2018 | Cable et al. |
| 2001/0051645 A1 | 12/2001 | Chiang |
| 2001/0051657 A1 | 12/2001 | Chiang et al. |
| 2002/0006946 A1 | 1/2002 | Aspnes et al. |
| 2002/0045751 A1 | 4/2002 | Kukkola |
| 2002/0049226 A1 | 4/2002 | Chiang et al. |
| 2002/0107390 A1 | 8/2002 | Kukkola |
| 2002/0123521 A1 | 9/2002 | Lavin |
| 2003/0027862 A1 | 2/2003 | Haning et al. |
| 2003/0040535 A1 | 2/2003 | Aspnes et al. |
| 2003/0078288 A1 | 4/2003 | Haning et al. |
| 2003/0078289 A1 | 4/2003 | Aspnes et al. |
| 2003/0114521 A1 | 6/2003 | Chiang et al. |
| 2003/0153513 A1 | 8/2003 | Shiomi et al. |
| 2003/0166724 A1 | 9/2003 | Rangeland |
| 2004/0029187 A1 | 2/2004 | Palmer |
| 2004/0039028 A1 | 2/2004 | Zhang et al. |
| 2004/0077694 A1 | 4/2004 | Chiang et al. |
| 2004/0097589 A1 | 5/2004 | Yi-Lin et al. |
| 2004/0110951 A1 | 6/2004 | Chiang |
| 2004/0116387 A1 | 6/2004 | Malm et al. |
| 2004/0116391 A1 | 6/2004 | Piccariello et al. |
| 2004/0142868 A1 | 7/2004 | Sleeman |
| 2004/0152783 A1 | 8/2004 | Olon et al. |
| 2004/0157844 A1 | 8/2004 | Dow et al. |
| 2004/0219218 A1 | 11/2004 | Martino et al. |
| 2004/0220147 A1 | 11/2004 | Malm et al. |
| 2005/0004184 A1 | 1/2005 | Ryono et al. |
| 2005/0038122 A1 | 2/2005 | Rangeland |
| 2005/0054727 A1 | 3/2005 | Rangeland |
| 2005/0085541 A1 | 4/2005 | Shiohara et al. |
| 2006/0046980 A1* | 3/2006 | Erion ................. A61P 5/14 514/79 |
| 2009/0118236 A1 | 5/2009 | Erion et al. |
| 2010/0081634 A1 | 4/2010 | Erion et al. |
| 2015/0045389 A1 | 2/2015 | Madden et al. |
| 2016/0319548 A1 | 11/2016 | Shevlin |
| 2017/0105956 A1 | 4/2017 | Kaminski et al. |
| 2017/0112864 A1 | 4/2017 | Cable et al. |
| 2018/0243263 A1 | 8/2018 | Jain et al. |
| 2018/0360846 A1 | 12/2018 | Lefebvre |
| 2019/0083515 A1 | 3/2019 | Cable et al. |

(56) References Cited

U.S. PATENT DOCUMENTS

| | | | |
|---|---|---|---|
| 2019/0255080 A1 | 8/2019 | Lian et al. | |
| 2020/0179412 A1 | 6/2020 | Lian et al. | |

FOREIGN PATENT DOCUMENTS

| | | | |
|---|---|---|---|
| EP | 1 297 833 | 4/2003 | |
| EP | 1 471 049 | 10/2004 | |
| EP | 1 666 035 | 6/2006 | |
| EP | 2 428 516 | 3/2012 | |
| EP | 1 689 383 | 10/2012 | |
| JP | 2007-512359 | 5/2007 | |
| JP | 2012-513394 | 6/2012 | |
| JP | 2019-516783 | 6/2019 | |
| KR | 10-2001-0020472 | 3/2001 | |
| MX | MX/a/2019/003032 | 10/2019 | |
| WO | WO 89/08458 | 9/1989 | |
| WO | WO 90/08155 | 7/1990 | |
| WO | WO 90/10636 | 9/1990 | |
| WO | WO 91/06569 | 5/1991 | |
| WO | WO 91/11181 | 8/1991 | |
| WO | WO 95/00135 | 1/1995 | |
| WO | WO 95/24919 | 9/1995 | |
| WO | WO 96/05190 | 2/1996 | |
| WO | WO 96/40048 | 12/1996 | |
| WO | WO 97/21993 | 6/1997 | |
| WO | WO 98/07435 | 2/1998 | |
| WO | WO 98/41216 | 9/1998 | |
| WO | WO 98/57919 | 12/1998 | |
| WO | WO 99/00353 | 1/1999 | |
| WO | WO 99/26966 | 6/1999 | |
| WO | WO 99/29321 | 6/1999 | |
| WO | WO 99/38376 | 8/1999 | |
| WO | WO 99/45016 | 9/1999 | |
| WO | WO 99/62507 | 12/1999 | |
| WO | WO 00/00468 | 1/2000 | |
| WO | WO 00/07972 | 2/2000 | |
| WO | WO 00/39077 | 7/2000 | |
| WO | WO 00/51971 | 9/2000 | |
| WO | WO 00/52015 | 9/2000 | |
| WO | WO 00/58279 | 10/2000 | |
| WO | WO 01/13936 | 3/2001 | |
| WO | WO 01/18013 | 3/2001 | |
| WO | WO 01/36365 | 5/2001 | |
| WO | WO 01/60784 | 8/2001 | |
| WO | WO 01/72692 | 10/2001 | |
| WO | WO 01/79287 | 10/2001 | |
| WO | WO 01/94293 | 12/2001 | |
| WO | WO 01/98256 | 12/2001 | |
| WO | WO 02/03914 | 1/2002 | |
| WO | WO 02/04515 | 1/2002 | |
| WO | WO 02/05834 | 1/2002 | |
| WO | WO 02/11666 | 2/2002 | |
| WO | WO 02/26752 | 4/2002 | |
| WO | WO 02/32408 | 4/2002 | |
| WO | WO 02/060374 | 8/2002 | |
| WO | WO 02/062780 | 8/2002 | |
| WO | WO 02/066017 | 8/2002 | |
| WO | WO 02/072528 | 9/2002 | |
| WO | WO 02/079181 | 10/2002 | |
| WO | WO 02/092550 | 11/2002 | |
| WO | WO 03/003013 | 1/2003 | |
| WO | WO 03/015771 | 2/2003 | |
| WO | WO 03/018515 | 3/2003 | |
| WO | WO 03/039456 | 5/2003 | |
| WO | WO 03/061557 | 7/2003 | |
| WO | WO 03/061567 | 7/2003 | |
| WO | WO 03/070169 | 8/2003 | |
| WO | WO 03/075835 | 9/2003 | |
| WO | WO 03/084915 | 10/2003 | |
| WO | WO 03/094845 | 11/2003 | |
| WO | WO 03/099864 | 12/2003 | |
| WO | WO 03/105760 | 12/2003 | |
| WO | WO 04/007430 | 1/2004 | |
| WO | WO 2004/005342 | 1/2004 | |
| WO | WO 04/014318 | 2/2004 | |
| WO | WO 04/018421 | 3/2004 | |
| WO | WO 04/026097 | 4/2004 | |
| WO | WO 04/041208 | 5/2004 | |
| WO | WO 04/065620 | 8/2004 | |
| WO | WO 04/066929 | 8/2004 | |
| WO | WO 04/067482 | 8/2004 | |
| WO | WO 04/078947 | 9/2004 | |
| WO | WO 04/091636 | 10/2004 | |
| WO | WO 04/093799 | 11/2004 | |
| WO | WO 04/103289 | 12/2004 | |
| WO | WO 05/009433 | 2/2005 | |
| WO | WO 05/016862 | 2/2005 | |
| WO | WO 05/021895 | 3/2005 | |
| WO | WO 05/028488 | 3/2005 | |
| WO | WO 05/042556 | 5/2005 | |
| WO | WO 05/051298 | 6/2005 | |
| WO | WO 05/123729 | 12/2005 | |
| WO | WO 06/128055 | 11/2006 | |
| WO | WO 06/128056 | 11/2006 | |
| WO | WO 06/128058 | 11/2006 | |
| WO | WO 07/009913 | 1/2007 | |
| WO | WO 2009/089093 | 7/2009 | |
| WO | WO 2010/074992 | 7/2010 | |
| WO | WO 2011/038207 | 3/2011 | |
| WO | WO 2017/184811 | 10/2017 | |
| WO | WO 2018/053036 | 3/2018 | |
| WO | WO 2018/094265 | 5/2018 | |
| WO | WO 2018/193006 | 10/2018 | |
| WO | WO 2018/226604 | 12/2018 | |
| WO | WO 2019/005816 | 1/2019 | |
| WO | WO 2020/117962 | 6/2020 | |
| WO | WO 2020/117987 | 6/2020 | |

OTHER PUBLICATIONS

International Search Report and Written Opinion, re PCT Application No. PCT/US2017/062393, dated Jun. 20, 2018.
Alexander et al.,Drugs and Their Structural Motifs, Chapter 1, pp. 28-29, Metabolism, Pharmacokinetics and Toxicity of Functional Groups—Impact of Chemical Building Blocsk on ADMET, 2010.
Alonso-Merino, et al., "Thyroid hormones inhibit TGF-p signaling and attenuate fibrotic responses," PNAS, 2016, vol. 113(24), pp. E3451-E3460.
Amma, L.L., et al., "Distinct Tissue-Specific Roles for Thyroid Hormone Receptors p and al in Regulation of Type 1 Deiodinase Expression," Mot. Endocrinol. 15:467-475, The Endocrine Society (2001).
Anderson, S.N., et al., "Activation of Electrophilic Aromatic Substitution by the Substituent -CH2Co(dmgH)2py. Products of Reaction of Benzylcobaloximes with Halogens in Acetic Acid," J. Chern. Soc. Perkin Trans. II 311-318, Royal Society of Chemistry (1972).
Annett, R.G., et al., "Enzymatically catalysed decarboxylation of P-carboxyaspartic acid (Asa)," Can. J. Chern. 68:886-887, NRC Research Press (1990).
Antons, K.A., et al., "Clinical Perspectives of Starin-Induced Rhabdomyolysis," Am. J. Med. 119:400-409, Excerpta Medica (May 2006).
Apriletti, J.W., et al., "Molecular and Structural Biology of Thyroid Hormone Receptors," Clin. Exp. Pharmacol. Physiol. 25:S2-SI 1, Blackwell Science Asia (1998).
Archer, S.J., et al., "Hepatitis C Virus NS3 Protease Requires Its NS4A Cofactor Peptide for Optimal Binding of a BoronicAcid Inhibitor as Shown by NMR,"Chern. Biol. 9:79-92, Elsevier Science Ltd (Jan. 2002).
Arnold, S., et al., "3,5-Diiodothyronine binds to subunit Va of cytochrome-c oxidase and abolishes the allosteric inhibition of respiration by ATP," Eur. J. Biochem. 252:325-330, Blackwell Science Ltd (1998).
Arnold, L.A., et al., "Discovery of Small Molecule Inhibitors of the Interaction of the Thyroid Hormone Receptor with Transcriptional Coregulators," J. Biol. Chern. 280:43048-43055, American Society for Biochemistry and Molecular Biology (Dec. 2005).
Auerbach, B.J., et al., "Comparative Effects of HMG-CoA reductase inhibitors on apo B production in the casein-fed rabbit: Atorvastatin versus Lovastatin," Atherosclerosis 115:173-180, Elsevier Science Ltd (1995).

(56) References Cited

OTHER PUBLICATIONS

Auberson, Y.P., et al., "N-Phosphonoalkyl-5-Aminomethylquinoxaline-2,3-Diones: In Vivo Active AMPA and NMDA (Glycine) Antagonists," Bioorg. Med. Chem. Lett. 9:249-254, Elsevier Science Ltd (1999).

Ayajiki, K., et al., "Endothelial and Neuronal Functions in Cerebral and Temporal Arteries from Monkeys Fed a High Cholesterol Diet," J. Cardiovascular Pharmacol. 40:456-466, Lippincott Williams & Wilkins (Sep. 2002).

Ayers, et al., "Thyroid hormone analogues: their role in treatment of hyperlipidemia," J. Endocrinol. Diabetes Obes 2(3): 1042. 2014.

Ball, S.G., et al., "3,5-Diiodo-L-thyronine (T2) has selective thyromimetic effects in vivo and in vitro," J. Mal. Endocrinol. 19:137-147, Society for Endocrinology (1997).

Baxter, J.D., et al., "Structure-Based Design and Synthesis of a Thyroid Homone Receptor (TR) Antagonist," Endocrinology 143:517-524, Endocrine Society (Feb. 2002).

Baxter, J.D., et al., "Selective activation of thyroid hormone signaling pathways by GC-1: a new approach to controlling cholesterol and body weight," Trends Endocrinol. Metab. 15:154-157, Elsevier Science Ltd (May/Jun. 2004).

Beg, M.A.A. and Clark, H.C., "Chemistry of the Trifluoromethyl Group, Part III. Phenyltrifluoromethylphospine and Related Compounds," Can. J. Chem. 39:564-570, NRC Research Press (1962).

Beg, M.A.A. and Clark, H.C., "Chemistry of the Trifluoromethyl Group, Part IV. Diphenyltrifluoromethylphophine and Complex Formation by Phenyltrifluoromethylphospines," Can. J. Chem. 40:283-288, NRC Research Press (1962).

Benayoud, F. and Hammond, G.B., "An expedient synthesis of (a,a-difluoroprop-2-ynyl) phosphonate esters," Chem. Commun. 1447-1448, Royal Society of Chemistry (1996).

Bhattacharya, "Investigation and management of the hepatic glycogen storage diseases," Transl Pediatrics, vol. 4, No. 3, Jan. 1, 2015.

Bianco, A.C., et al., "Biochemistry, Cellular and Molecular Biology, and Physiolgical Roles of the Iodothyronine Selenodeiodinases," Endocrine Rev. 23:38-89, The Endocrine Society (Feb. 2002).

Bilger, C., et al., "A Convenient One-Pot Synthesis of Aralkyl Bromides and Iodides by Reductive Halogenation of Aromatic Carbonyl Compounds," Synthesis 902-904, Georg Thieme Verlag (1988).

Blennemann, B., et al., "Tissue-Specific Regulation of Fatty Acid Synthesis by Thyroid Hormone," Endocrinology 130:637-643, The Endocrine Society (1992).

Bobyleva, V., et al., "Decrease in mitochondrial energy coupling by thyroid hormones: a physiological effect rather than a pathological hyperthyroidism consequence," FEBS Lett. 430:409-413, Elsevier Science Ltd (1998).

Bocan, T.M.A., et al., "HMG-CoA reductase and ACAT inhibitors act synergistically to lower plasma cholesterol and limit atherosclerotic lesion development in the cholesterol-fed rabbit," Atherosclerosis 139:21-30, Elsevier Science Ltd. (1998).

Bogardus, J.B. and Higuchi, T., "Kinetics and Mechanism of Hydrolysis of Labile Quaternary Ammonium Derivatives of Tertiary Amines," J. Pharm. Sci. 71:729-735, Wiley (1982).

Bohmer, V. and Vogt, W., "7.(o-Hydroxyphenyl)methylphosphinic acids: Synthesis and Potentiometric Determination of their pKa Values," Helvetica Chimica Acta 76:139-149, Verlag Helvetica Chimica Acta (1993).

Boyd, E.A., et al., "Facile Synthesis of Functionalised PhenylphosphinicAcid Derivatives," Tetrahedron Lett. 37:1651-1654, Elsevier Science Ltd (1996).

Boyd, E.A. and Regan, A.C., "Synthesis of y-Keto-substituted Phosphinic Acids from Bis(trimethylsilyl)phosponite and a,P-Unsaturated Ketones," Tetrahedron Lett. 332:813-816, Elsevier Science Ltd (1992).

Boyer et al., "Synthesis and Biological Evaluation of a Series of Liver-Selective Phosphonic Acid Thyroid Hormone Receptor Agonists and Their Prodrugs", J. Med. Chem., 517075-7093 (2008).

Briel, D., et al., "3-Amino-5-phenoxythiophenes: Syntheses and Structure-Function Studies of a Novel Class of Inhibitors of Cellular L-Triiodothyronine Uptake," J. Med. Chem. 42:1849-1854, American Chemical Society (1999).

Brooks, et al., "Large Animal Models and New Therapies for Glycogen Storage Disease," J Inherit Metab Dis. May 2015; 38(3): 505-509.

Brown, K., et al., "Accelerator Mass Spectrometry for Biomedical Research," Meth. Enzymol. 402:423-443, Academic Press (Nov. 2005).

Cabalska, et al., "Treatment with D-thyroxine of patients with glycogen storage diseases type VI and Via," Materia Medica Polona, Wydawnietwa Handlu Zagranicznego, Warsaw, PL, vol. 19, No. 4, Sep. 30, 1987.

Cable, et al., "Reduction of Hepatic Steatosis in Rats and Mice After Treatment with a Liver-Targeted Thyroid Hormone Receptor Agonist," Hepatology, 2009, vol. 49, pp. 407-417.

Carvalho, et al., "Glycogen Storage Disease type 1a - a secondary cause for hyperlipidemia: report of five cases," Journal of Diabetes & Metabolic Disorders 2013, 12:25.

Christian, M.S. and Trenton, N.A., "Evaluation of thyroid function in neonatal and adult rats: The neglected endocrine mode of action," Pure Appl. Chem. 75:2055-2068, International Union of Pure and Applied Chemistry (Nov. 2003).

Chou, et al., "Glycogen storage disease type 1 and G6Pase-p deficiency: etiology and therapy," Nat Rev Endocrinol. Dec. 2010; 6(12): 676-688.

Cimmino, M., et al., "Demonstration of in vivo metabolic effects of 3,5-di-iodothyronine," J. Endocrinol. 149:319-325, Society for Endocrinology (1996).

Clutterbuck, P.W. and Cohen, J.B., "The Aryl and Alkyl Sulphonamides," J. Chem. Soc. 123:2507-2515, Royal Society of Chemistry (1923).

Collazo, A-M.G., et al., "Thyroid receptor ligands. Part 5: Novel bicyclic agonist ligands selective forthe thyroid hormone recepter B," Bioorg. Med. Chem. Lett. 16:1240-1244, Elsevier Science Ltd. (Mar. 2006).

Columbano, A., et al., "The Thyroid Hormone Receptor- Agonist GC-1 Induces Cell Proliferation in Rat Liver and Pancreas," Endocrinology 147:3211-3218, Endocrine Society (Mar. 2006).

Connolly, et al., "Future Pharmacotherapy for Non-alcoholic Steatohepatitis (NASH): Review of Phase 2 and 3 Trials," Journal of Clinical and Translational Hepatology (2018) vol. 6, pp. 264-275. Epub Jun. 28, 2018.

Corrie, J.E.T. and Trentham, D.R., "Synthetic, Mechanistic and Photochemical Studies of Phosphate Esters of Substituted Benzoins," J. Chem. Soc. Perkin Trans. 1: 2409-2417, Chemical Society (1992).

Crimmins, M.T., et al., "Asymmetric Aldol Additions: Use of Titanium Tetrachloride and (-)-Sparteine for the Soft Enolization of N-Acyl Oxazolidinones, Oxazolidinethiones, and Thiazolidinethiones," J. Org. Chem. 66:894-902, American Chemical Society (2001).

Croxall, W.J., et al., "Organic Reactions with Boron Fluoride. XI. The Condensation of Propylene with m-andp-Hydroxybenzoic acids," J. Am. Chem. Soc. 57:1549-1551, American Chemical Society (1935).

Danzi, S., et al., "Triiodothyronine-mediated myosin heavy chain gene transcription in the heart," Am. J. Physiol. Heart Circ. Physiol. 284:H2255-H2262, The American Physiological Society (2003).

Database Beilstein, (Online), Beilstein Registry No. 7222862, 6 pages, Beilstein Institute for Organic Chemistry, Frankfurt-Main, DE.

Database Beilstein, (Online), Beilstein Registry No. 7505261, 2 pages, Beilstein Institute for Organic Chemistry, Frankfurt-Main, DE.

Database Beilstein, (Online), Beilstein Registry No. 6636402, 4 pages, Beilstein Institute for Organic Chemistry, Frankfurt-Main, DE.

Database CAplus, Chemical Abstract Service, Columbus Ohio, Enrion, M.D., et al., "Preparation of phosphonic acid-containing liver-selective thyromimetics effective against metabolic diseases," WO 2005-0512986, 16 pages (created Jun. 2005).

(56) References Cited

OTHER PUBLICATIONS

Davis, R. and Untch, K.G., "Direct one-step Conversion of Alcohols into Nitriles," J. Org. Chem. 46:2985-2987, American Chemical Society (1981).

Davis, P.J., et al., "Comparison of the mechanisms of nongenomic actions of thyroid hormone and steroid hormones," J. Endocrinol. Invest. 25: 377-388, Italian Society of Endocrinology (Apr. 2002).

De Brabandere, V.I., et al., "Isotope Dilution-Liquid Chromatography/ Electrospray Ionization-Tandem Mass Spectrometry forthe Determination of Serum Thyroxine as a Potential Reference Method," Rapid Commun. Mass Spectrometry 12:1099-1103, Wiley (1998).

De Sandro, V., et al., "Comparison of the Effects of Propylthiouracil, Amiodarone, Diphenylhydantoin, Phenobarbital, and 3-Methylcholanthrene on Hepatic and Renal T4 Metabolisn and Thyroid Gland Function in Rats," Toxicol. Appl. Pharmacol. 111:263-278, Academic Press (1991).

Demori, I., et al., "3,-5-diiodothyronine Mimics the Effect of Triiodothyronine on Insulin-like growth Factor Binding Protein-4 Expression in Cultured Rat Hepatocytes," Harm. Metab. Res. 36:679-685, Georg Thieme Verlag (Oct. 2004).

Deprele, S. and Montchamp, J.-L., "A novel and convenient preparation of hypophosphite esters," J. Organometallic Chem. 643-644:154-163, Elsevier Science Ltd (Aug. 2002).

Dhawan, B. and Redmore, D., "1,2-Alkanediol Bis(Dihydrogen Phosphates)," Synth. Commun. 18:327-331, Georg Thieme Verlag (1988).

Dingwall, J.G., et al., "Diethoxymethylphosphonites and Phospinates. Intermediates for the Synthesis of a,P-and y-Aminoalkylphosphonous Acids," Tetrahedron 45:3787-3808, Pergamon Press (1989).

DiStefano III, J.J. and Feng, D., "Comparative Aspects of the Distrubution, Metabolism, and Excretion of Six lodothyronines in the Rat," Endocrinology 123:2514-2525, Endocrine Society (1988).

Docter, R., et al., "Inhibition of Uptake of Thyroid Hormone into Rat Hepatocytes by Preincubation with N-Bromoacetyl-3,3 ',5-Triiodothyronine," Endocrinology 123:1520-1525, The Endocrine Society (1988).

Dow, R.L., et al., "Discovery of a Novel Series of 6-Azauracil-Based Thyroid Hormone Receptor Ligands: Potent, TRP Subtype-Selective Thyromimetics," Bioorg. Med. Chem. Lett. 13:379-382, Elsevier Science Ltd (Nov. 2003).

Duntas, "Thyroid Disease and Lipids," Thyroid, vol. 12, No. 4, 2002.

Drechsler, U. and Hanack, M., "An Easy Route from Catechols to Phthalonitriles," Synlett 1207-1208, Georg Thieme Verlag (1998).

Earle, M.J., et al., "The first high yield green route to a pharmaceutical in a room temperature ionic liquid," Green Chem. 2:261-262, Royal Society of Chemistry (2000).

Ebdrup, S., et al., "Structure-activity relationship for aryl and heteroarly boronic acid inhibitors of homone-sensitive lipase," Bioorg. Med. Chem. 13:2305-2312, Elsevier Science Ltd (Jan. 2005).

Edmundson, R.S., et al., "Cyclic Organophosphorus Compounds. Part 23. Configurational Assignments in the 4-Phenyl-1 ,3,2A.5-dioxaphosphorinane Series. X-Ray Molecular Structure of cis-2-Benzylamino-4-phenyl-1,3,2-dioxaphosphorinane 2- Oxide," J. Chem. Res. Synop. 5:122-123, Science Reviews, Ltd. (1989).

Edwards, M.L., et al., "Difluoromethyldiphenylphosphine oxide. A new reagent for conversion of carbonyl compounds to 1,1 -difluoroolefins," Tetrahedron Lett. 31:5571-5574, Elsevier Science Ltd (1990).

Eisch, J.J., et al., "Rearrangement and Cleavage of [(Aryloxy)methyl]silanes by Organolithium Reagents: Conversion of Phenols into Benzylic alcohols," J. Org. Chem. 47:5051-5056, American Chemical Society (1982).

Ekins, R., "Validity of Analog Free Thyroxin Immunoassays" Clin. Chem. 33:2137-2152, American Association For Clinical Chemistry (1987).

Endres, et al., "D-Thyroxine Treatment in Glycogen Storage Disease Type Via," Pediatric Research, vol. 18, No. 8, Aug. 1, 1984.

Erion, M.D., et al., "Design, Synthesis, and Characterization of a Series of Cytochrome P450 SA-Activated Prodrugs (HepDirect Prodrugs) Useful for Targeting Phosph(on)ate-Based Drugs to the Liver," J. Am. Chern. Soc. 126:5154-5163, American Chemical Society (Apr. 2004).

Erion, M.D., et al., "Liver-Targeted Drug Delivery Using HepDirect Prodrugs," J. Pharmacol. Exper. Ther. 312:554-560, American Society for Pharmacology and Experimental Therapeutics (Feb. 2005).

Erion, et al., "Targeting thyroid hormone receptor- agonists to the liver reduces cholesterol and triglycerides and improves the therapeutic index," PNAS, Sep. 25, 2007, vol. 104, No. 39.

Fabiano, E., et al., "A Simple Conversion of Alcohols into Amines," Synthesis 190-192, Georg Thieme Verlag (1987).

Faergemann, J., et al., "Dose-Response Effects of Triiodothyroacetic Acid (Triac) and otherThyroid Hormone Analogues on Glucocorticoid-Induced Skin Atrophy in the Haired Mouse," Acta Derm. Venereal. 82:179-183, Society for the Publication of Acta Dermato-Venereologica (Mar. 2002).

Farquhar, D., et al., "Biologically-Cleavable Phosphate Protective Groups: 4- Acyloxy-1,3,2-Dioxaphosphorinanes as Neutral Latent Precursors of Dianionic Phosphates," Tetrahedron Lett. 36:655-658, Elsevier Science Ltd. (1995).

Feinstein, S., et al., "Submitral Atheromatous Lesions in Monkey and Man", Clin. Cardiol. 6:109-115, John Wiley & Sons, Inc. (1983).

Feng, W., et al., "Hormone-Dependent Coactivator Binding to a Hydrophobic Cleft on Nuclear Receptors," Science 280:1747-1749, American Association for the Advancement of Science (1998).

Field, L.D. and Wilkinson, M.P., "A new Synthesis of 1,2-Bis(Bis(Trifluoromethyl)Phosphino)ethane," Tetrahedron Lett. 33:7601-7604, Elsevier Science Ltd (1992).

Fieser, L.F. andArdao, M.I., "Investigation of the Chemical Nature of Gonyleptidine," J. Am. Chem. Soc. 78:774-781, American Chemical Society (1956).

Fleischmann, K., et al., "Synthesis of HR 916 B: The First Technically Feasible Route to the 1-(Pivaloyloxy)ethyl Esters of Cephalosporins," Liebigs Ann. 1735- 1741, Verlag Chemie (1996).

Fong, T.-L., et al., "Hyperthyroidism and Hepatic Dysfunction," J. Clin. Gastroenterol. 14:240-244, Raven Press (1992).

Freitas, F.R.S., et al., "Spared bone mass in rats treated with thyroid hormone receptor TRf3-selective compound GC-1," Am. J. Physiol. Endocrinol. Metab. 285:EI 135-EI 141, American Physiological Society (Sep. 2003).

Freitas, F.R.S., et al.,"The Thyroid Hormone Receptor f3-Specific Agonist GC-1 Selectivity Affects the Bone Development of Hypothyroid Rats," J. Bone Mineral Res. 20:294-304, American Society for Bone and Mineral Research (Nov. 2004).

Froestl, W., et al., "Phosphinic Acid Analogues of GABA. I. New Potent and Selective GABAB Agonists," J. Med. Chem. 38:3297-3312, American Chemical Society (1995).

Froestl, W., et al., "Phosphinic Acid Analogues of GABA. 2. Selective, Orally Active GABAB Antagonists," J. Med. Chem. 38:3313-3331, American Chemical Society (1995).

Fujitaki, et al., "Preclinical Pharmacokinetics of a HepDirect Prodrug of a Novel Phosphonate-Containing Thyroid Hormone Receptor Agonist," The American Society for Pharmacology and Experimental Therapeutics, vol. 36, No. 11,2008.

Gallagher, M. J. and Honegger, H., "Organophosphorus Intermediates. VI. The Acid-Catalysed Reaction of Trialkyl Orthoformates with PhosphinicAcid," Aust. J. Chem. 33:287-294, Commonwealth Scientific And Industrial Research Organization (1980).

Garibaldi, et al. "Destrothyroxine treatment of phosphorylase-kinase deficiency glycogenosis in four boys," Helvetica Paediatrica Acta, Schwabe, Basel, CH, vol. 33, No. 4-5, Oct. 31, 1978.

Gilman, H. and Calloway, N_O_, "Super-Aromatic Properties ofFuran. II. The Friedel-Crafts Reaction," J. Am. Chem. Soc. 55:4197-4205, American Chemical Society (1933).

Goglia, F., et al., "In Vitro binding of 3,5-di-iodo-L-thyronine to rat liver mitochondria," J. Mol. Endocrinol. 13: 275-282, Society for Endocrinology (1994).

Goglia, F., "Biological Effects of 3,5-Diiodothyronine (T2) ," Biochemistry (Moscow) 70:164-172, Pleiades Publishing, Inc. (Feb. 2005).

(56) References Cited

OTHER PUBLICATIONS

Goglia, F., et al., "Interaction of diiodothyronines with isolated cytochrome c oxidase," FEBS Lett. 346:295-298, Elsevier Science Ltd. (1994).
Goodrich, P., et al., "Kinetic Study of the Metal Triflate Catalyzed Benzoylation of Anisole in an Ionic Liquid," Ind. Eng. Chem. Res. 45:6640-6647, American Chemical Society (Sep. 2006).
Goswami, A., et al., "Inhibition by coumadin anticoagulants of enzymatic outer ring monodeiodination of iodothyronines," Biochem. Biophys. Res. Commun. 104:1231-1238, Academic Press (1982).
Goya, R.G., et al., "Effects of Growth Hormone and Thyroxine on Thymulin Secretion in Aging Rats," Neuroendocrinology 58:338-343, S. Karger AG, Basel (1993).
Greco, M.N., et al., "Discovery of Potent, Selective, Orally Active, Nonpeptide Inhibitors of Human Mast Cell Chymase," J. Med. Chem. 50:1727-1730, American Chemical Society (Mar. 2007).
Gregory, R.B. and Berry, M.N., "On the thyroid hormone-induced increase in respiratory capacity of isolated rat hepatocytes," Biochim. Biophys. Acta I 098:6 I- 67, Elsevier Science Ltd. (1991).
Gronemeyer, H., et al., "Principles for Modulation of the Nuclear Receptor Superfamily" Nature Reviews, Drug Discovery 3:950-964, Nature Publishing Group (Nov. 2004).
Grover, G.J., et al., "Development of the Thyroid Homone Receptor P-Subtype Agonist KB-141: A Strategy for Body Weight Reduction and Lipid Lowering with Minimal Cardiac Side Effects," Cardiovascular Drug Rev. 23:133-148, Blackwell Publishing (Nov. 2005).
Grover, G.J., et al., "Selective thyroid hormone receptor-P activation: A strategy for reduction of weight, cholesterol, and lipoprotein (a) with reduced cardiovascular liability," Pnas JOO:I0067-I0072, National Academy of Sciences (Aug. 2003).
Grundy, et al., "Implications of Recent Clinical Trials for the National cholesterol Education Program Adult Treatment Panel III Guidelines," Circulation. 2004;110:227-239; downloaded from http://circ.ahajournals.org/.
Guernik, S., et al., "A novel system consisting of Rh-DuPHOS and ionic liquid for asymmetric hydrogenations," Chem. Commun. 2314-2315, Royal Society of Chemistry (2001).
Hadvary, P. and Weller, T., "202. Conformationally Restricted Analogs of Platelet-Activating Factor (PAP)," Helvetica ChimicaActa 69:1862-1871, Verlag Helvetica Chimica Acta (1986).
Hansen, et al., "Mouse models of nonalcoholic steaohepatitis in preclinical drug development," Drug Discovery Today, vol. 22, No. 11, Nov. 2017.
Hashimoto, A., et al., "Design and synthesis of complementing ligands for mutant thyroid hormone receptor TRP(R320H): a tailor-made approach toward the treatment of resistance to thyroid hormone," Bioorg. Med. Chem. 13:3627- 3639, Elsevier Science Ltd (Jun. 2005).
Haugen, et al., "Drugs That Suppress TSH or Cause Central Hypothyroidism," Best Pract Res Clin endocrinol. Metab. Dec. 2009; 23(6): 793-800.
Hayakawa, Y., et al., "A General Approach to Nucleoside 31- and 5' Monophosphates," Tetrahedron Lett. 28:2259-2262, Elsevier Science Ltd. (1987).
Hedfors, A., et al., "Thyroid Receptor Ligands. 3. Design and Synthesis of 3,5-Dihalo-4-alkoxyphenylalkanoic Acids as Indirect Antagonists of the Thyroid Hormone Receptor," J. Med. Chem. 48:3114-3117, American Chemical Society (May 2005).
Heimberg, M., et al., "Plasma Lipoproteins and Regulation of Heptic Metabolism of Fatty Acids in Altered Thyroid States," Endocrine Rev. 6:590-607, Endocrine Society (1985).
Hennemann, G., et al., "Carrier-Mediated Transport of Thyroid Hormone into Rat Hepatocytes is Rate-Limiting in Total Cellular Uptake and Metabolism," Endocrinology 119:1870-1872, Endocrine Society (1986).
Hennemann, G., "Notes on the History of Cellular Uptake and Deiodination of Thyroid Hormone," Thyroid 15:753-756, Mary Ann Liebert Publishers (Aug. 2005).
Holt, "Thyroxine Therapy in Glycogen-Storage Disease," Nutrition Reviews, vol. 14, No. 7, Jul. 27, 1956.

Holy, A, "Phosphonomethoxyalkyl Analogs of Nucleotides," Curr. Pharm. Des. 9:2567-2592, Bentham Science Publishers (Dec. 2003).
Hopper et al., 1999, CAS: 130:332269.
Horst, C., et al., "3,5-Di-iodo-L-thyronine suppresses TSH in rats in vivo and in rat pituitary fragments in vitro," J. Endocrinol. 145:291-297, Society for Endocrinology (1995).
Horst, C., et al., "Rapid Stimulation of hepatic oxygen consumption by 3,5-di- iodo-L-thyronine," Biochem. J. 261:945-950, Portland Press (1989).
Howarth, J., et al., "Sodium Borohydride Reduction of Aldehydes and Ketones in the Recyclable Ionic Liquid [BMIM]PF 6," Synth. Commun. 31:2935-2938, Taylor & Francis (2001).
Huddleston, J.G., et al., "Characterization and comparison of hydrophilic and hydrophobic room temperature ionic liquids incorporating the imidazolium cation," Green Chem. 3:156-164, Royal Society of Chemistry (2001).
Hum, G., et al., "Synthesis of [Difluoro-(3-alkenylphenyl)-methyl]-phosphonic Acids on Non-crosslinked Polystyrene and Their Evaluation as Inhibitors of PTPIB," Bioorg. Med. Chem. Lett. 12:3471-3474, Elsevier Science Ltd (Aug. 2002).
Hume, J.R., et al., "Anion Transport in Heart," Physiol. Rev. 80:31-81, The American Physiological Society (2000).
Hunter, D.H., et al., "Crown ether catalysis of decarboxylation and decarbalkoxylation of j3-keto acids and malonates: a synthetic application," Can. J. Chem. 58:2271-2277, NRC Research Press (1980).
Ibrahini et al., 2000, CAS: 133:14000.
Ichikawa, K., et al., "Mechanism ofliver-selective thyromimetic activity of Sk&F L-94901: evidence for the presence of a cell-type-specific nuclear iodothyronine transport process," J Endocrinol. 165:391-397, Society for Endocrinology (2000).
Ing, H.R., "The Pharmacology of Homologous Series," Fortschritte der Arzneimittelforschung. Progress in drug research. Progres des recherches pharmaceutiques 20:306-309, Birkhauser Verlag (1964).
Iyer, S. and Liebeskind, L.S., "Regiospecific Synthesis of 2-Methoxy-3-methyl- 1,4-benzoquinones fromMaleoylcobalt Complexes andAlkynes via Lewis Acid Catalysis. A Highly Convergent Route to Isoquinoline Quinones," J Am. Chem. Soc. 109:2759-2770, American Chemical Society (1987).
Jain, M.R., et al., "Dual PPARβ/y agonist saroglitazar improves liver histopathology and biochemistry in experimental NASH models", Liver International, (2018) vol. 38, pp. 1084-1094. Epub Dec. 14, 2017.
Jakobsson, T., et al.," Potential Role of Thyroid Receptor 3 Agonists in the Treatment of Hyperlipidemia", Drugs (2017) vol. 77, pp. 1613-1621.
Jepson, E.M., "Thyroxine analogues as hypocholesterolemic agents," Am. Heart J 67:422-424, Mosby (1964).
Johnson, E.O., et al., "Experimentally-induced hyperthyroidism is associated with activation of the rat hypothalamic-pituitay-adrenal axis," Eur. J Endocrinol. 153:177-185, BioScientifica Ltd (Jul. 2005).
Jones, P.B. and Porter, N.A., "2-Aroylbenzoyl Serine Proteases: Photoreversible Inhibtion or Photoaffinity Labeling?," J Am. Chem. Soc. 121:2753-2761, American Chemical Society (1999).
Jorgensen, E.C., "Thyroid Hormones and Analogs. II. Structure-Activity Relationships," in: Hormonal Proteins and Peptides, Li, C.H., eds., Academic Press, New York, NY, pp. 107-204 (1978).
Jorgensen, E.C., "Thyroid Hormones and Analogs. I. Synthesis, Physical Properties and Theoretical Calculations," in: Hormonal Proteins and Peptides, Li, C.H., eds., Academic Press, New York, NY, pp. 56-105 (1978).
Jorgensen, E.C. and Murray, W.J., "Thyroxine Analogs. 22. Thyromimetic Activity of Halogen-Free Derivatives of 3,5-Dimethyl-L-Thyronine,"J Med. Chem. 17:434-439 (1974).
Kadenbach, B., et al., "Mitochondrial Energy Metabolsim is Regulated via Nuclear-Coded Subunits of Cytochrome C Oxidase," Free Radical Biol. Med. 29:211-221, Elsevier Science Ltd (2000).
Kazemifard, A.G., et al., "Identification and quantitation of sodium-thyroxine and its degradation products by LC using electrochemical and MS detection," J Pharm. Biomed. Anal. 25:697-71 I, Elsevier Science Ltd. (2001).

(56) References Cited

OTHER PUBLICATIONS

Kennedy, J.A., et al., "Influence ofImiprarnine on the Hypothalamic/Pituitary/Thyroid Axis ofthe Rat," Metabolism 46:1429-1434, W.B. Saunders (1997).
Kennedy, J.F, et al., "Isolation of thyroxine-binding globulin (TBG) by immunoadsorption chromatography: some physical and immunochemical characteristics of TBG," Clinica Chimica Acta 129:251-261, Elsevier Science Ltd (1983).
Kido et al., "Current status of hepatic glycogen storage disease in Japan: clinical manifestations, treatments and long-term outcomes," Joural of Human Genetics (2013) 58, 285-292.
Kishnani, et al., "Diagnosis and management of glycogen storage disease type I: a practice guideline ofthe American College of Medical Genetics and Genomics," Genetics in Medicine, submitted Aug. 12, 2014.
Knolker, H-J. and Filali, S., "Transition Metal Complexes in Organic Synthesis, Part 69. Total Synthesis oftheAmaryllidaceae Alkaloids Anhydrolycorinone and Hippadine Using Iron-and Palladium-Mediated Coupling Reactions," Synlett 1752-1754, Georg Thieme Verlag (Jun. 2003).
Kobayashi, H., et al., "Organization ofNucleosides Supported by Boronic-Acid-Appended Poly(L-lysine): Creation of a Novel RNA Mimic," Bull. Chern. Soc. Jpn. 74:1311-1317, The Chemical Society of Japan (2001).
Koehler, K., et al., "Thyroid Receptor Ligands. 6. A High Affinity "Direct Antagonist" Selective for the Thyroid Hormone Receptor," J. Med. Chern. 49:6635-6637, American Chemical Society (Oct. 2006).
Koerner, D., et al., "Binding of Selected Iodothyronine Analogues to Receptor Sites of Isolated Rat Hepatic Nuclei," J. Biol.Chern. 250:6417-6423, American Society for Biochemistry and Molecular Biology (1975).
Koulischer, "Glycogen-Storage Disease : A Study on the Effect of SodiumAThyroxine and Glucagon," AMA Journal of Diseases of Children, vol. 91, No. 2, Feb. 1, 1956.
Krause, B.R., et al., "Opposite effects of beza:fibrate and gemfibrozil in both normal and hypertriglyceridemic rats," Atherosclerosis 127:91-101, Elsevier Science Ltd (1996).
Kvetny, J., "3,5-T2 Stimulates Oxygen Consumption, But Not Glucose Uptake in Human Mononuclear Blood Cells," Horm. Metab. Res. 24:322-325, Georg Thieme Verlag (1992).
Lacoste, AM., et al., "Research Regarding Aminoalkylphosphonic Acids. II. - Iodine Derivatives ofthe Phosphonic Analog of Tyrosine," Bull. Soc. Chim. Biol. 49:1827-1835, Masson Et Cie (1967).
Lacoste, A.-M., et al., "Biochemistry- Synthesis and biological properties ofthe phosphonic analog of thyroxine," C.R. Acad. Sci. Paris 267:1890-1892, Gauthier Villars Editeur (1968).
Lacoste, A.-M., et al., "Endrocrinology. Action ofthe phosphonic analog of thyroxine on post-embryonic development ofthe tadpole of Rana dalmatina Bon," Biol. Soc. Bordeaux 1684-1689 (1967).
Lanni, A., et al., "Specific Binding sites for 3,3-diiodo-L-thyronine (3,3'-T2) in rat liver mitochondria," FEES Lett. 351:237-240, Elsevier Science Ltd (1994).
Lanni, A., et al., "Effect of 3,3'-di-iodothyronine and 3,5-di-iodothyronine on rat liver mitochondria," J. Endocrinol. 136:59-64, Society for Endocrinology (1993).
Lanni, A., et al., "Effect of 3,3'-diiodothyronine and 3,5-diiodothyronine on rat liver oxidative capacity," Mol. Cell. Endocrinol. 86:143-148, Elsevier Scientific Publishers Ireland (1992).
Lanni, A., et al., "Rapid stimulation in vitro ofrat liver cytochrome oxidase activity by 3,5-diiodo-l-thyronine and by 3,3'-diiodo-L-thyronine," Mol. Cell. Endocrinol. 99:89-94, Elsevier Science Ltd (1994).
Lanni, A., et al., "Expression of uncoupling protein-3 and mitochondrial activity in the transition from hypothyroid to hyperthyroid state in rat skeletal muscle," FEBS Lett. 444:250-254, Elsevier Science Ltd. (1999).
Lanni, A., et al., "Calorigenic effect of diiodothyronines in the rat," J. Physiol. 494:831-837, Blackwell Publishing (1996).

Laskorin, B.N., et al., "Preparation and Investigation of the Steric Structure of Sterically Hindered a-oxo Phosphoryl Compounds," Zhurnal Obshchei Khimii 44:1716-1720, RossiiskayaAkademiya Nauk (1974).
Lee, S.-G., et al., "Microwave-assisted Kabachnik-Fields Reaction in Ionic Liquid," Bull. Korean Chern. Soc. 23:667-668, The Korean Chemical Society (Mar. 2002).
Lee, Y.-P., et al., "Effects of Thyroid Hormones on the Guinea Pig," Endocrinology 86:241-250, The Endocrine Society (1970).
Leonard, J.L. and Rosenberg, I.N., "Iodothyronine 5'-Deiodinase from Rat Kidney: Substrate Specificity and the 5'-Deiodination of Reverse Triiodothrvonine, Endocrinolof!"V 107:1376-1383, The Endocrine Society (1980).
Leonard, J.L. and Rosenberg, I.N., "Thyroxine 5-Deiodinase Activity of Rat Kidney: Observations on Activation by Thiols and Inhibition by Propylthiouracil," Endocrinology 103:2137-2144, The Endocrine Society (1978).
Lewis, D.S., "Effects of dietary cholestrol on adipose tissue lipoprotein lipase in the baboon," Biochim. Biophys. Acta 879:44-50, Elsevier Science Ltd (1986).
Li, Y.-L., et al., "Thyroid receptor ligands. Part 4: 4'-amido bioisosteric ligands selective for the thyroid hormone receptor beta," Bioorg. Med. Chern. Lett. 16:884-886, Elsevier Science Ltd (Feb. 2006).
Lian, B., "Evaluation of the Thyroid Receptor Agonist VK2809 on Liver Disease in DIO-NASH Mice,", Hepatology, Oct. 2017, vol. 66, No. Suppl. 1, Sp. Iss. SI, p. 1038A.
Liddle, C., et al., "Separate and Interactive Regulation of Cytochrome P450 3A4 by Triiodothyronine, Dexamethasone, and Growth Hormone in Cultured Hepatocytes," J. Clin. Endocrinol. Metab. 83:2411-2416, The Endocrine Society (1998).
Lin, C.-C., et al., Pharmacokinetics of Pradefovir and PMEA in Healthy Volunteers After Oral Dosing of Pradefovir,11 J Clin. Pharmacol. 45:1250-1258, Sage Science Press (Nov. 2005).
Linsel-Nitschke, P. and Tall, Ar., "Hdl as a Target in the Treatment of Atherosclerotic Cardiovascular Disease," Nature Reviews, Drug Discovery 4:193- 205, Nature Publishing Group (Mar. 2005).
Liotta, D., et al., "A Simple, Inexpensive Procedure for the Large-Scale Production of Alkyl Quinones," J Org. Chern. 48:2932-2933, American Chemical Society (1983).
Lombardi, A., et al., "Characterization of the binding of 3, 3'-diiodo-L-thyronine to rate liver mitochondria," J Endocrinol. 154:119-124, Society for Endocrinology (1997).
Lombardi, A., et al., "Effect of 3,5-di-iodo-L-thyronine on the mitochondrial energy-transduction apparatus," Biochem. J 330:521-526, Portland Press (1998).
Lonsdale, et al., "Normalization of Hepatic Phosphorylase Kinase Activity and Glycogen Concentration in Glycogen Storage Diseas Type IX During Treatment with Sodium D Thyroxine," American Journal of Human Genetics; Annual Meeting of the American Society of Human Genetics, vol. 29, No. 6, Nov. 1, 1977.
Lukashev, N.V., et al., "Palladium-Catalyzed Cross-Coupling Reactions of Organocopper Derivatives of Methylphosphonic Esters and Amides with Aryl and Hetaryl Iodides," Russian J. Gen. Chern. 71:172-178, Kluwer Academic Publishers (2001).
Mackenzie, P.I., et al., "Regulation of UDP Glucuronosyltransferase Genes," Curr. Drug Metab. 4:249-257, Bentham Science Publishers (Jun. 2003).
Madrigal-Matute, et al., "Regulation of Liver Metabolism by Autophagy," Reviews in Basic and Clinical Gastroenterology and Hepatology, Gastroenterology 2016 150:328-339.
Mains, R.E. and Eipper, B.A., "Tissue Culture of Primary Rat Anterior Pituitary Cells" in Regulatory Peptides: From Molecular Biology to Function, Costa, E., Trabucchi, M., eds., Raven Press, New York City, NY, pp. 1-8 (1982).
Makinen, M.W. and Lee, C.-P., "Biochemical Studies of Skeletal Muscle Mitochondria: I. Microanalysis of Cytochrome Content, Oxidative and Phosphorylative Activities of Mammalian Skeletal Muscle Mitochondria," Arch. Biochem. Biophys. 126:75-82, Academic Press (1968).
Malevannaya, R.A., et al., "(Dialkoxyphosphinyl) Acetic Acids and Some of Their Analogs," Zhurnal Obshchei Khimii 41:1426-1434, Rossiiskaya Akademiya Nauk (1971).

(56) References Cited

OTHER PUBLICATIONS

Marcune, B.F., et al., "Selective displacement of aryl fluorides with hydroquinone: synthesis of 4-phenoxyphenols" Tetrahedron Lett. 46:7823-7826, Elsevier Science Ltd (Nov. 2005).

Marimuthu, A., et al., "TR Surfaces and Conformations Required to Bind Nuclear Receptor Corepressor" Mal. Endocrinol. 16:271-286, The Endocrine Society (Feb. 2002).

Matsui, T., et al., "Discovery of Novel Phosphonic Acid Derivatives as New Chemical Leads for Inhibitors of TNF-a Production," Bioorg. Med. Chern. 10:3807-3815, Elsevier Science Ltd (Aug. 2002).

McClain, R.M., "Mechanistic considerations for the relevance of animal data on thyroid neoplasia to human risk assessment," Mutation Res. 333:131-142, Elsevier Science Ltd. (1995).

Merlins, K., et al., "Transition-Metal-Catalyzed Benzylation of Arenes and Heteroarenes," Angew. Chern. Int. Ed. 44:238-242, Wiley-VCR Verlag GmbH & Co. (Dec. 2004).

Middleton, W.J., "New Fluorinating Reagents. Dialkylaminosulfur Fluorides," J. Org. Chem. 40:574-578, American Chemical Society (1975).

Miyahara, E.H., et al., "Thyroid hormone receptor-P-selective agonist GC-24 spares skeletal muscle type 1 to II fiber shift," Cell Tissue Res. 321:233-241, Springer-Verlag (Aug. 2005).

Mocchegiani, E., et al., "Neuroendocrine-thymus interactions. I. In vitro modulation of thymic factor secretion by thyroid hormones," J. Endocrinol. Invest. 13:139-147, Italian Society of Endocrinology (1990).

Moreno, M., et al., "How the thyroid controls metabolism in the rat: different roles for triiodothyronine and diiodothyronines," J. Physiol. 505:529-538, Cambridge Univ. Press (1997).

Morkin, E., et al., "Pilot Studies on the Use of 3, 5-Diiodothyropropionic Acid, a Thyroid Hormone Analog, in the Treatment of Congestive Heart Failure," Cardiology 97:218-225, S. Karger AG, Basel (Jul. 2002).

Moscioni, AD. and Gartner, L.M., "Thyroid Hormone and Hepatic UDP- Glucuronosyl Transferase Activity: Contrary Effects in Rat and Mouse," Res. Commun. Chern. Pathol. Pharmacol. 39:445-462, Pjd Publications Ltd (1983).

Murphy-Jolly, M.B., et al., "The synthesis of tris(perfluoroalkyl)phosphines," Chern. Commun. 4479-4480, Royal Society of Chemistry (Aug. 2005).

Nabeshima, T., et al., "Rate-accelerating Metal Ion Effects on Decarboxylation of a-Keto Acids by a Thiazolium Ion bearing a Metal Binding Site," J. Chern. Soc. Chern. Commun. 373-374, Royal Society of Chemistry (1991).

Ness, G.C., et al., "Effects of L-Triiodothyronine and the Thyromimetic L-94901 on Serum Lipoprotein Levels and Hepatic Low-Density Lipoprotein Receptor, 3- Hydroxy-3-methylglutaryl Coenzyme A Reductase, and Apo A-l Gene Expression," Biochem. Pharmacol. 56:121-129, Elsevier Science Ltd (1998).

Nguyen, N.-H., et al., "Hammett Analysis of Selective Thyroid Hormone Receptor Modulators Reveals Structural and Electronic Requirements for Homone Antagonists," J. Am. Chern. Soc. 127:4599-4608, American Chemical Society (Mar. 2005).

Nishinaga, et al., "Model Reactions for the Biosynthesis of Thyroxine. XII. The Nature of a Thyroxine Precursor Formed in the Synthesis of Thyroxine from Diiodotyrosine and Its Keto Acid Analog," Biochemistry 7:388-397, American Chemical Society (1968).

Nurtdinov, S.Kh., et al., "Reactions of Alkylphosphonous Dichlorides with Carboxylic Acid Chlorides," Zhurnal Obshchei Khimii 41:2486-2490, Rossiiskaya Akademiya Nauk (1971).

Ocasio, Cory A, and Scanlan, T.S., "Clinical prospects for new thyroid hormone analogues" Curr. Opin. Endocrinol. Diabetes 12:363-370, Lippincott Williams & Wilkins (Oct. 2005).

Ocasio, Cory A, and Scanlan, T.S., "Design and characterization of a thyroid hermone receptor a (TRa)-Specific Agonist," ACS Chern. Biol. 1:585-593, American Chemical Society (Oct. 2006).

O'Reilly, Ian, and Murphy, M.P., "Studies on the rapid stimulation of mitochondrial respiration by thyroid hormones." Acta Endocrinol. 127:542-546, Romanian Society for Endocrinology (1992).

O'Reilly, Ian, and Murphy, M.P., "Treatment of hypothyroid rats with T2 (3,5-di- iodo-L-thyronine) rapidly stimulates respiration in subsequently isolated mitochondria," Biochem. Soc. Trans. 20:59S, Portland Press (1991).

Osuka, A, et al., "Synthesis of Arenephosphonates by Copper(l) Iodide- Promoted Arylation of Phosphite Anions," Synthesis 69-71, George Thieme Verlag- Stuttart (1983).

Pan, S.-Y., et al., "Bifendate treatment attenuates hepatic steatosis in cholesterol/bile salt- and high-fat diet-induced hypercholesterolemia in mice," Eur. J. Pharmacol. 552:170-175 Elsevier Science Ltd (Dec. 2006).

Panne, P., et al., "Cyanide initiated perfluoroorganylations with perfluoroorgano silicon comoounds" J. Fluorine Chern. 112:283-286 Elsevier Science Ltd (2001).

Petervari, E., et al., "Hyperphagia of hyperthyroidism: Is neuropeptide Y involved?" Regulatory Peptides 131:103-110, Elsevier Science Ltd (Nov. 2005).

Prashad, M., "Phosphonate vs. Phosphinate Elimination during Olefination of Aldehydes," Tetrahedron Lett. 34:1585-1588, Elsevier Science Ltd (1993).

Psarra, A.-M.G., et al., "The mitochondrion as a primary site of action of steroid and thyroid hormones: Presence and action of steroid and thyroid hormone receptors in mitochondria of animal cells." Mol. Cell. Endocrinol. 246:21-33, Elsevier Science Ltd (Feb. 2006).

Pue, M.A., et al., "The disposition of Sk&F L-94901, a selective thyromimetic in rat, dog and cynomolgus monkey," Eur. J. Drug Metab. Pharmacokinetics 14:209-219, Edition Medecine Et Hygiene (1989).

Radominska-Pandya, A., et al., "A Historical Overview of the Heterologous Expression of Mammalian UDP-Glucuronosyltransferase Isoforms Over the Past Twenty Years," Curr. Drug Metab. 6:141-160, Bentham Science Publishers Ltd. (Apr. 2005).

Rai, R., and Katzenellenbogen, J.A., "Effect of Conformational Mobility and Hydrogen-Bonding Interactions on the Selectivity of Some Guanidinoaryl-Substituted Mechanism-Based Inhibitors of Trypsin-like Serine Proteases," J. Med. Chern. 35:4297-4305, American Chemical Society (1992).

Raparti et al., "Selective thyroid hormone receptor modulators," Indian J. Endocrinol. Metab. Mar. 2013-Apr. 17(2): 211-218.

Rashid, S., et al., "Effect of Atorvastatin on High-Density Lipoprotein Apolipoprotein A-l Production and Clearance in the New Zealand White Rabbit," Circulation 106:2955-2960, Lippincott Wiliams & Wlkins (Dec. 2002).

Razumov, A.I. and Gazizov, M.B., "Reactivity of Organophosphorus Carbonyl- Containing Compounds IV. Synthesis, Properties, and Structure of Acylphosphinic Esters," Zhurnal Obshchei Khimii 37:2738-2742, Rossiiskaya Akademiya Nauk (1967).

Reiter et al. {Phosphinic acid-based MMP-13 inhibitors that spare MMP-1 and MMP-3, Bioorganic & Medicinal Chemistry Letters (2003), 13(14), 2331-2336.

Ren, S.G., et al., "Dose-Response Relationship Between Thyroid Hormone and Growth Velocity in Cynomolgus Monkeys," J. Clin. Endocrinol. Metab. 66:1010-1013, The Endocrine Society (1988).

REUTERS Market News, "BRIEF-Viking Therapeutics says statistically significant reductions in fibrosis, liver collage, after 8 weeks of VK2809 treatment," [retrieved from Internet on Jul. 28, 2018] <URL: https://www.reuters.com/article/brief-viking-therapeutics-says-statistic/brief-viking-therapeutics-says-statistically-significant-reductions-in-fibrosis-liver-collagen-after-8-weeks-of-vk2809-treatment-idUSFWNI J308Y> Published online Jun. 6, 2017.

Ribeiro, R.C.J., et al., "X-ray Crystallographic and Functional Studies of Thyroid Hormone Receptor," J. Steroid Biochem. Molec. Biol. 65:133-141, Pergamon Press (1998).

Rooda, S.J.E., et al., "Metabolism of Triiodothyronine in Rat Hepatocytes," Endocrinology 125:2187-2197, The Endocrine Society (1989).

Ross, J. and Xiao, J., "Friedel-Crafts acylation reactions using metal tritiates in ionic liquid," Green Chern. 4:129-133, Royal Society of Chemistry (Feb. 2002).

(56) References Cited

OTHER PUBLICATIONS

Ruhlandt-Senge, K. and Englich, U., "Synthesis and characterization of the first discrete potassium thiolates displaying three different coordination spheres at potassium in one molecule," Chern. Commun. 147-148, Royal Society of Chemistry (1996).
Ryono et al. CAS: 141:395288.
Ryono et al., 2004, CAS: 927006.
Saitoh, H. and Aungst, B.J., "Improvement of the Intestinal Absorption of a Peptidomimetic, Boronic Acid Thrombin Inhibitor Possibly Utilizing the Oligopeptide Transporter," Pharm. Res. 16:1786-1789, Plenum Publishing Corporation (1999).
Sakamoto, T., et al., "Cross-Coupling of N-Heteroaryl Halides with Active Methylene Compounds in the Presence of Tetrakis(triphenylphosphine)palladium," Chern. Pharm. Bull. 36:1664-1668, Pharmaceutical Society of Japan (1988).
Sakamoto, T., et al., "Palladium-Catalyzed Condensation of Aryl Halides with Phenylsulfonylacetonitrile and Diethyl Cyanomethylphosphonate," Chern. Pharm. Bull. 38:1513-1517, Pharmaceutical Society of Japan (1990).
Samuels, H.H., et al., "Depletion of L-3,5,3'-Triiodothyronine and L-Thyroxine in Euthyroid Calf Serum for Use in Cell Culture Studies of the Action of Thyroid Hormone," Endocrinol of!V 105:80-85, The Endocrine Society (1979).
Sano, M. and Yamatera, H., "Potential Energy Surface of [Cu(H2o)6]2+ and [Zn(H20)6] 2+ Derived From Ab Initio MO Calculations," Chern. Lett. 1495-1496, The Chemical Society of Japan (1980).
Sass, D.A., et al., "Nonalcoholic Fatty Liver Disease: A Clinical Review," Dig. Dis. Sci. 50:171-180, Springer Science Business Media, Inc. (Jan. 2005).
Saulnier, M.G., et al., "Microwave-assisted synthesis of primary amine HX salts from halides and 7M ammonia in methanol," Tetrahedron Lett. 45:397-399, Elsevier Science Ltd. (Jan. 2004).
Schlosser, M. and Geneste, H., "The Organometallic Route to Benzylamine Type Monoamine Oxidase Inhibitors," Tetrahedron 54:10119-10124, Pergamon Press (1998).
Schmitt, L, et al., "Synthesis of Arylalkylmonofluorophosphonates as Myo- Inositol monophosphatase Ligands," Tetrahedron Lett. 39:4009-4012, Elsevier Science Ltd. (1998).
Schroder-van der Elst, J.P., et al., "Effects of 5,5'-diphenylhydantoin on the thyroid status in rats," Eur. J. Endocrinol. 134:221-224, BioScientifica Ltd (1996).
Selenkow, H.A. and Asper, Jr., S.P., "Biological Activity of Compounds Structurally Related to Thyroxine," Physiol. Rev. 35:426-474, American Physiological Society (1955).
Shi, Y., et al., "Mutant-Selective Thyromimetics for the Chemical Rescue of Thyroid Hormone Receptor Mutants Associated with Resistance to Thyroid Hormone," Biochemistry 44:4612-4626, American Chemical Society (Mar. 2005).
Smith, C.L. and O'Malley, B.W., "Coregulator Function: A Key to Understanding Tissue Specificity of Selective Receptor Modulators," Endocrine Rev. 25:45-71, The Endocrine Society (Feb. 2004).
Soldin, SJ., et al., "The measurement of free thyroxine by isotope dilution tandem mass spectrometry," Clinica Chimica Acta 358:113-118, Elsevier Science Ltd (Aug. 2005).
Song, K., et al., "Induction of angiotensin converting enzyme and angiotensin II receptors in the atherosclerotic aorta of high-cholesterol fed Cynomolgus monkeys," Atherosclerosis 138:171-182, Elsevier Science Ltd (1998).
Stanton, J.L., et al., "Synthesis and Biological Activity of Phenoxyphenyl Oxamic Acid Derivatives Related to L-Thyronine," Bioorg. Med. Chern. Lett. 10:1661-1663, Elsevier Science Ltd (2000).
Sterling, K. and Brenner, M.A., "Thyroid Hormone Action: Effect of Triiodothyronine on Mitochondrial Adenine Nucleotide Translocase In Vivo and In Vitro," Metabolism 44:193-199, W.B. Saunders (1995).
Tacke, et al., "An update on the recent advances in antifibrotic therapy," Expert Review of Gastroenterology & Hepatology (2018) vol. 12(11), pp. 1143-1152. Epub Oct. 3, 2018.
Tai, S.S.-C., et al., "Candidate Reference Method for Total Thyroxine in Human Serum: Use of Isotope-Dilution Liquid Chromatography-Mass Spectrometry with Electrospray Ionizaton," Clin. Chern. 48:637-642, American Association For Clinical Chemistry (Jan. 2002).
Takayama, S., et al., "Antithyroid Effects of Propylthiouracil and Sulfamonomethoxine in Rats and Monkeys," Toxicol. Applied Pharmacol. 82:191-199, Academic Press (1986).
Tai, D.M. and Karlish, S.J.D., "Synthesis of a Novel Series of ArylmethylisothiouroniumDerivatives," Tetrahedron 51:3823-3830, Pergamon Press (1995).
Taylor, A.H., et al., "Beneficial Effects of a Novel Thyromimetic on Lipoprotein Metabolism," Mol. Pharmacol. 52:542-547, American Society for Pharmacology and Experimental Therapeutics (1997).
Taylor, S.D., et al., "Synthesis of Aryl(DifluoromethylenePhosphonates) via Electrophilic Fluorination of a-Carbanions of Benzylic Phosphonates with N-Fluorobenzenesulfonimide," Tetrahedron 54:1691-1714, Pergamon Press (1998).
Thienpont, L.M., et al., "Isotope Dilution-Gas Chromatography/Mass Spectrometry and Liquid Chromatography/Electrospray Ionization-Tandem Mass Spectrometry for the Determination of Triiodo-L-Thyronine in Serum," Rapid Commun. Mass Spectrometry 13:1924-1931, John Wiley & Sons, Ltd (1999).
Thornber, C.W., "Isosterism and Molecular Modification in Drug Design," Chern. Soc. Rev. 8:563-580, Chemical Society (1979).
Togashi, M., et al., "Conformational adaptation of nuclear receptor ligand binding domains to agonists: Potential for novel approaches to ligand design," J. Steroid Biochem. Mol. Biol. 93:127-137, Elsevier Science Ltd (Feb. 2005).
Tomilov, AP., et al., "Electrochemical synthesis of diethyl fluoromethanephosphonate," J. Fluorine Chern. 82:39-41, Elsevier Science Ltd. (1997).
Toussaint, 0., et al., "The Copper(l)-Catalyzed Decarboxylation of Malonic Acids: A New Mild and Quantitative Method," Synthesis 1029-1031, Georg Thieme Verlag (1986).
Trost, S.U., et al., "The Thyroid Hormone Receptor-13-Selective Agonist GC-1 Differentially Afflects Plasma Lipids and Cardiac Activity," Endocrinology 141:3057-3064, The Endocrine Society (2000).
Tsuchimoto, T., et al., "Scandium(lll) Triflate Catalyzed Friedel-Crafts Alkylation Reactions," J. Org. Chern. 62:6997-7005, American Chemical Society (1997).
Tyree, E.B., et al., "Effect of L-Triiodothyronine on Radiation-Induced Pulmonary Fibrosis in Dogs", Radiation Research (1966) vol. 28, pp. 30-36.
Underwood, A. H., et al., "A thyromimetic that decreases plasma cholesterol levels without increasing cardiac activity," Nature 324:425-429, Nature Publishing Group (1986).
Van Rompaey, K., et al., "A versatile synthesis of 2-substituted 4-amino-1,2,4,5-tetrahydro-2-benzazepine-3-ones," Tetrahedron 59:4421-4432, Pergamon Press (Apr. 2003).
Vaughan, M.K., et al., "Chronic Exposure to Short Photoperiod Inhibits Free Thyroxine Index and Plasma Levels of Tsh, T4, Triiodothyronine (T3) and Cholesterol in Female Syrian Hamsters," Comp. Biochem. Physiol. 7JA:615-618, Pergamon Press Ltd (1982).
Veer, G.V.D.S., et al., "Temperature Effects on Free-Thyroxine Measurements: Analytical and Clinical Consequences," Clin. Chern. 38:1327-1331, American Association For Clinical Chemistry (1992).
Verd, J.C., et al., "Different effect of simvastatin and atorvastatin on key enzymes involved in VLDL synthesis and catabolism in high fat/cholestrol fed rabbits," Br. J. Pharmacol. 127:1479-1485, Nature Publishing Group (1999).
Villicev, C.M., et al., "Thyroid hormone receptor -specific agonist GC-1 increases energy expenditure and prevents fat-mass accumulation in rats," J. Endocrinol. 193:21-29, Society for Endocrinology (Jan. 2007).
Visser, T.J., et al., "Deiodination of Thyroid Hormone by Human Liver," J. Clin. Endocrinol. Metab. 67:17-24, The Endocrine Society (1988).
Walker, D.M., et al., "Design and Synthesis of y-Oxygenated Phosphinothricins as Inhibitors of Gluamine Synthetase," J. Chern. Soc. Perkin Trans. 1 659-666, Royal Society of Chemistry (1990).
Wang, B., et al., "Effects of triiodo-thyronine on angiotensin-induced cardiomyocyte hypertrophy: reversal of increased -myosin

(56) References Cited

OTHER PUBLICATIONS heavy chain gene expression," Can. J. Physiol. Pharmacol. 84:935-941, NRC Research Press (Aug. 2006).
Wang, R., et al., "Salsalate Administration - A Potential Pharmacological Model of the Sick Euthyroid Syndrome," J. Clin. Endocrinol. Metab. 83:3095-3099, Endocrine Society (1998).
Waschbiisch, R., et al., "A high yield:ing synthesis of diethyl-l-fluoromethylphosphonate in pure form," C. R Acad. Sci. Paris, t. 1, Serie II c 1:49-52, Elsevier Science Ltd (1998).
Wasserscheid, P. and Keim, W., "Ionic Liquids-New "Solutions" for Transition Metal Catalysis," Angew Chern. Int. Ed. 39:3772-3789, Wiley-VCR Verlag GmbH (2000).
Webb, P., et al., "Design of thyroid hormone receptor antagonists from first principles," J. Steroid Biochem. Mol. Biol. 83:59-73, Elsevier Science Ltd (Dec. 2002).
Wechter, W.J., et al., "Hypocholesterolemic Agents. Thyroalkanols," J. Med. Chern. 8:474-478, American Chemical Society (1965).
Wells, P.G., et al., "Effect ofthyrotoxicosis on liver blood flow andpropranolol disposition after long-term dosing," Clin. Pharmacol. Ther. 33:603-608, Nature Publishing Group (1983).
Welton, T., "Room-Temperature Ionic Liquids. Solvents for Synthesis and Catalysis," Chern. Rev. 99:2071-2083, American Chemical Society (1999).
Wibom, R., et al., "A sensitive method for measuring ATP-formation in rat muscle mitochondria," Scand. J Clin. Lab. Invest. 50:143-152, Taylor & Francis Health Sciences (1990).
Wienand, A, et al., "Design, Synthesis and Biological Evaluation of Selective Boron-containing Thrombin Inhibitors," Bioorg. Med. Chern. 7:1295-1307, Elsevier Science Ltd. (1999).
Willnow, T.E. and Herz, J., "Animal models for disorders of hepatic lipoprotein metabolism," J Mal. Med. 73:213-220, Springer-Verlag (1995).
Winder, W.W., et al., "Effects of thyroid hormone administration on skeletal muscle mitochondria," Am. J Physiol. 228:1341-1345, American Physiological Society (1975).
Wondisford, F.E., "Unlikely partners in weight loss?," Cell Metab. 3:81-82, Cell Press (Feb. 2006).
Wu, K.-M. and Farrelly, J.G., "Preclinical Development of New Drugs that Enhance Thyroid Hormone Metabolism and Clearance: Inadequacy of Using Rats as an Animal Model for Predicting Human Risks in an IND and NPA," Am. J Therap. 13:141-144, Lippincott Williams & Wilkins (March/Apr. 2006).
Wu, Y., et al., "Removal of Thiazolidinethione Auxiliaries with Benzyl Alcohol Mediated by Dmap," J Org. Chern. 69:6141-6144, American Chemical Society (May 2004).
Xu, L., et al., "Heck Reaction in Ionic Liquids and the in Situ Identification of N-Heterocyclic Carbene Complexes of Palladium," Organometallics 19:1123-1127, American Chemical Society (2000).
Yang, W., et al., "Boronic Acid Compounds as Potential Pharmaceutical Agents," Med. Res. Rev. 23:346-368, Wiley Periodicals, Inc. (May 2003).
Yang, C. and Pittman, Jr., C.U., "Reductions of Organic Functional Groups Using NaBHi or NaBH,JLiCI in Diglyme at 125 to 162 °C," Synth. Commun. 28:2027-2041, Georg Thieme Verlag (1998).
Yao, et al., "Regulation of fatty acid composition and lipid storage by thyroid hormone in mouse liver," Cell & Bioscience, Biomed Central Ltd. Vo. 4, No. 1 Jul. 30, 2014.

Ye, L., et al., "Thyroid Receptor Ligands. 1. Agonist Ligands Selective for the Thyroid Receptor pl," J Med. Chern. 46:1580-1588, American Chemical Society (Mar. 2003).
Yen, P.M., "Physiological and Molecular Basis of Thyroid Hormone Action," Physiol. Rev. 81:1097-1142, American Physiological Society (2001).
Yoshihara, H.A.1., et al., "Structural Determinants of Selective Thyromimetics" J. Med. Chern. 46:3152-3161, American Chemical Society (Jul. 2003).
Yoshioka, R., et al., "The Optical Resolution and Asymmetric Transformation of DL-p-Hydroxyphenylglycine with (+)-1-Phenylethanesulfonic Acid," Bull. Chern. Soc. Jpn. 60:649-652, The Chemical Society of Japan (1987).
Yu, K.-L., et al., "Concerning the Phosphorylation of Vicinal Dials," Synth. Commun. 18:465-468, Taylor & Francis, Inc. (1988).
Yu, G., et al., "Thyroid hormone inhibits lung fibrosis in mice by improving epithelial mitochondrial function", Nature Medicine (2018) vol. 24(1), pp. 39-49. Epub Dec. 4, 2017.
Viking Therapeutics, Press releases, "Viking Therapeutics Announces Presentation of Data from In Vivo Proof-of-Concept Study of VK2809 in Glycogen Storage Disease la (GSD la) at the 13th International Congress of Inborn Errors of Metabolism (ICIEM)", [retrieved from internet on Jun. 8, 2018] <URL: http://ir.vikingtherapeutics.com/2017-09-07-Viking-Therapeutics-Announces-Presentation-of-Data-from-ln-Vivo-Proof-of-Concept-Study-of-VK2809-in-Glycogen-Storage-Disease-la-GSD-la-at-the-13th-lnternational-Congress-of-lnborn-Errors-of-Metabolism-ICIEM> published on Sep. 7, 2017.
Viking Therapeutics—News & Events, "Viking Therapeutics Presents Results from In Vivo Study of VK2809 in Biopsy-Confirmed Non-Alcoholic Steatohepatitis (NASH) at the Annual Meeting of the American Association for the Study of Liver Diseases (AASLD)", Oct. 24, 2017, San Diego <URL: http://ir.vikingtherapeutics.com/2017-10-24-Viking-Therapeutics-Presents-Results-from-ln-Vivo-Study-of-VK2809-in-Biopsy-Confirmed-Non-Alcoholic-Steatohepatitis-NASH-at-the-Annual-Meeting-of-the-American-Association-for-the-Study-of-Liver-Diseases-AASLD> [retrieved from Internet on Feb. 9, 2020].
Viking Therapeutics—News & Events, "Viking Therapeutics Announces Results of Gene Expression Analysis from In Vivo Study of VK2809 in Non-Alcoholic Steatohepatitis (NASH)", Sep. 11, 2017, San Diego <URL: http://ir.vikingtherapeutics.com/2017-09-11-Viking-Therapeutics-Announces-Results-of-Gene-Expression-Analysis-from-ln-Vivo-Study-of-VK2809-in-Non-Alcoholic-Steatohepatitis-NASH> [retrieved from Internet on Feb. 9, 2020].
Zalkow, L.H., et al., "Studies in the Synthesis of Camptothecin. An Efficient Synthesis of 2,3-Dihydro-1H-pyrrolo[3,4-b]quinoline," J. Chern. Soc. 3551-3554, Royal Society of Chemistry (1971).
Zenker, N. and Jorgensen, E.C., "Thyroxine Analogs. I. Synthesis of 3,5-Diiodo- 4-(2'-alkylphenoxy)-DL-phenylalanines," J. Am. Chern. Soc. 81:4643-4647, American Chemical Society (1959).
Zhang, N. and Casida, J.E., "Novel Irreversible Butyrylcholinesterase Inhibitors: 2-Chloro-1-(substituted-phenyl)ethylphosphonic Acids," Bioorg. Med. Chern. 10:1281-1290, Elsevier Science Ltd (Nov. 2002).
Zhang, J. and Lazar, M.A., "The Mechanism of Action of Thyroid Hormones," Annu. Rev. Physiol. 62:439-466, Annual Reviews (2000).

\* cited by examiner

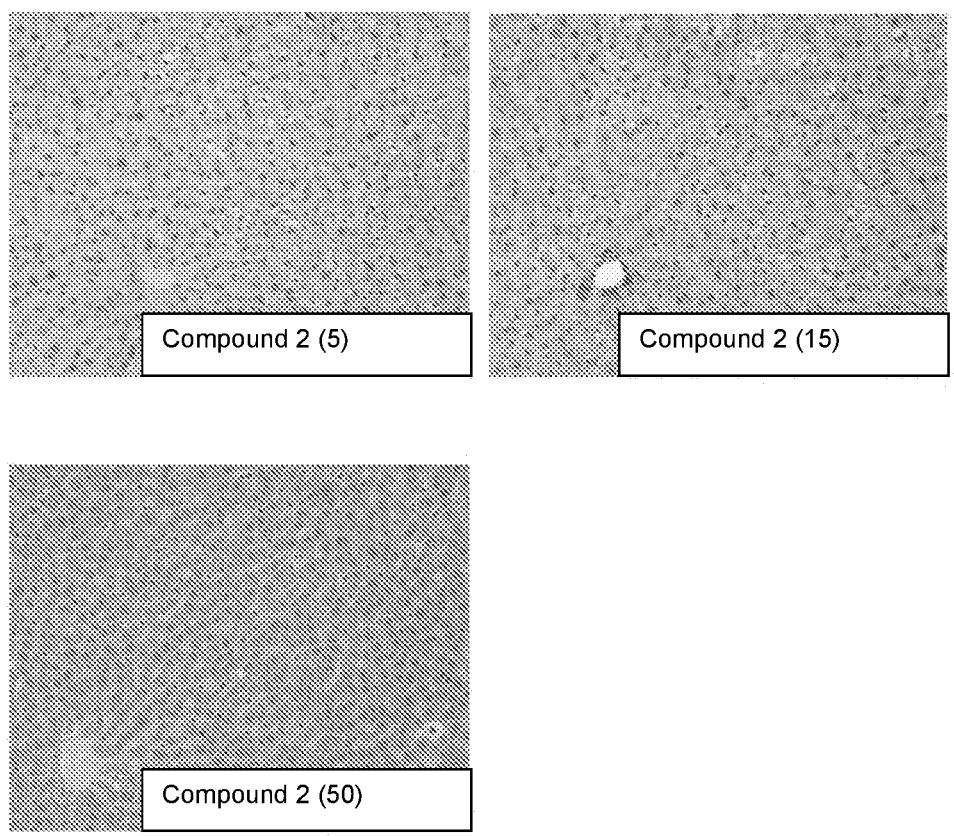
Figure 9, Continued

METHOD OF TREATING GLYCOGEN STORAGE DISEASE

CROSS REFERENCE TO RELATED APPLICATIONS

This application is U.S. National Phase under 35 U.S.C. § 371 of International Application No. PCT/US2017/062393, filed Nov. 17, 2017, designating the U.S. and published in English as International Pub. No. WO 2018/094265, which claims the benefit of U.S. Provisional Application No. 62/425,007, filed Nov. 21, 2016, and U.S. Provisional Application No. 62/456,610, filed Feb. 8, 2017, all of which are incorporated herein by reference in their entirety.

FIELD OF THE INVENTION

The present disclosure relates to the field of treatments for glycogen storage diseases and their symptoms. The treatments of the present disclosure may include thyroid hormone receptor agonists and/or modulators of thyroid hormone signaling.

DESCRIPTION OF THE RELATED ART

Glycogen storage diseases (GSD) comprise a group of disorders marked by dysfunction in the metabolism of glycogen, generally due to the loss of a necessary enzyme activity. Causes of glycogen storage disease include defects in glucose-6-phosphatase, debranching enzyme, glycogen synthase, glucose-6-phosphatase translocase, phosphatase translocase, alpha-1-4-glucosidase, amylo-1-6-glucosidase, amylo-1,4-to-1,6-transglucosidase, glycogen phosphorylase, phosphofructokinase, cyclic-3',5' AMP-dependent kinase, glucose transporter 2, and aldolase A, among others. Broadly, these defects occur in the synthesis, transport, or utilization of glycogen. Several of these defects lead to a buildup of glycogen in the liver, heart, and/or skeletal muscle as well as a concomitant defect in energy storage and energy metabolism throughout the body. Symptoms of glycogen storage diseases include elevated or reduced blood sugar, insulin insensitivity, myopathies, as well as hepatic symptoms such as steatosis, hyperlipidemia, hypercholesterolemia, cardiomegaly, hepatomegaly, fibrosis, cirrhosis, hepatocellular adenoma, and hepatocellular carcinoma. The symptoms and sequelae of glycogen storage diseases range in severity, from manageable metabolic dysfunction or exercise intolerance, to premature death, and presently available treatments cover a similar range, from dietary interventions to symptomatic treatment such as administration of statins and/or fibrates to manage cholesterol and lipid accumulation, and in some instances, liver, kidney, and/or bone marrow transplantation. There is need for improved therapies for the treatment of these disorders.

In particular, GSD Ia is characterized by an inability to metabolize glucose precursors, resulting in hypoglycemia and increased lipogenesis. The disease is caused by mutations in the gene for glucose-6-phosphatase (G6PC), a critical enzyme involved in the production of glucose from either glycogen or gluconeogenesis. Impaired G6PC function leads to dramatically elevated liver triglyceride levels in human patients and in animal models of the disease. In patients, this may contribute to serious long-term complications, such as severe hepatomegaly, hepatic adenomas, and hepatocellular carcinoma. Manifestations of the disease begin to appear shortly after birth and continue through adolescence into adulthood. There is currently no approved therapy for GSD Ia, and accordingly there is a need for new treatments for this condition in particular.

SUMMARY OF THE DISCLOSURE

The present disclosure relates to a method of treating a glycogen storage disease or symptom thereof, comprising administering to a subject in need thereof at least one compound of Formula I:

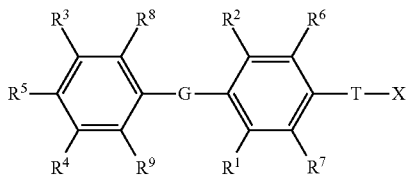

or a pharmaceutically acceptable salt thereof, wherein:

G is selected from the group consisting of —O—, —S—, —S(=O)—, —S(=O)$_2$—, —Se—, —CH$_2$—, —CF$_2$—, —CHF—, —C(O)—, —CH(OH)—, —CH(C$_1$-C$_4$ alkyl)-, —CH(C$_1$-C$_4$ alkoxy)-, —C(=CH$_2$)—, —NH—, and —N(C$_1$-C$_4$ alkyl)-;

T is selected from the group consisting of —(CR$^a_2$)$_k$—, —CR$^b$=CR$^b$—(CR$^a_2$)$_n$—, —(CR$^a_2$)$_n$—CR$^b$=CR$^b$—, —(CR$^a_2$)—CR$^b$=CR$^b$—(CR$^a_2$)—, —O(CR$^b_2$)(CR$^a_2$)$_n$—, —S(CR$^b_2$)(CR$^a_2$)$_n$—, N(R$^c$)(CR$^b_2$)(CR$^a_2$)$_n$—, N(R$^b$)C(O)(CR$^a_2$)$_n$—, —C(O)(CR$^a_2$)$_n$—, —(CR$^a_2$)$_m$C(O)—, —(CR$^a_2$)C(O)(CR$^a_2$)$_n$, —(CR$^a_2$)$_n$C(O)(CR$^a_2$)—, and —C(O)NH(CR$^b_2$)(CR$^a_2$)$_p$—;

k is an integer from 1-4;
m is an integer from 0-3;
n is an integer from 0-2;
p is an integer from 0-1;

each R$^a$ is independently selected from the group consisting of hydrogen, optionally substituted —C$_1$-C$_4$ alkyl, halogen, —OH, optionally substituted —O—C$_1$-C$_4$ alkyl, —OCF$_3$, optionally substituted —S—C$_1$-C$_4$ alkyl, —NR$^b$R$^c$, optionally substituted —C$_2$-C$_4$ alkenyl, and optionally substituted —C$_2$-C$_4$ alkynyl; with the proviso that when one R$^a$ is attached to C through an O, S, or N atom, then the other R$^a$ attached to the same C is a hydrogen, or attached via a carbon atom;

each R$^b$ is independently selected from the group consisting of hydrogen and optionally substituted —C$_1$-C$_4$ alkyl;

each R$^c$ is independently selected from the group consisting of hydrogen and optionally substituted —C$_1$-C$_4$ alkyl, optionally substituted —C(O)—C$_1$-C$_4$ alkyl, and —C(O)H;

R$^1$, and R$^2$ are each independently selected from the group consisting of halogen, optionally substituted —C$_1$-C$_4$ alkyl, optionally substituted —S—C$_1$-C$_3$ alkyl, optionally substituted —C$_2$-C$_4$ alkenyl, optionally substituted —C$_2$-C$_4$ alkynyl, —CF$_3$, —OCF$_3$, optionally substituted —O—C$_1$-C$_3$ alkyl, and cyano;

R$^6$, R$^7$, R$^8$, and R$^9$ are each independently selected from the group consisting of are each independently selected from the group consisting of hydrogen, halogen, optionally substituted —C C$_1$-C$_4$ alkyl, optionally substituted —S—C$_1$-C$_3$ alkyl, optionally substituted —C$_2$-C$_4$ alkenyl, optionally substituted —C$_2$-C$_4$ alkynyl, —CF$_3$, —OCF$_3$, optionally substituted —O—C$_1$-C$_3$ alkyl, and cyano; or R$^6$ and T are taken together along with the carbons they are attached to form a ring of 5 to 6 atoms including 0 to 2 heteroatoms independently selected from —NR$^i$—, —O—, and —S—, with the proviso that when there are 2 heteroatoms in the ring and both heteroatoms are different than nitrogen then both heteroatoms have to be separated by at least one carbon atom; and X is attached to this ring by a direct bond to a ring carbon, or by —(CR$^a{}_2$)— or —C(O)— bonded to a ring carbon or a ring nitrogen;

R$^i$ is selected from the group consisting of hydrogen, —C(O)C$_1$-C$_4$ alkyl, —C$_1$-C$_4$ alkyl, and —C$_1$-C$_4$-aryl;

R$^3$ and R$^4$ are independently selected from the group consisting of hydrogen, halogen, —CF$_3$, —OCF$_3$, cyano, optionally substituted —C$_1$-C$_{12}$ alkyl, optionally substituted —C$_2$-C$_{12}$ alkenyl, optionally substituted —C$_2$-C$_{12}$ alkynyl, —SR$^d$, —S(=O)R$^e$, —S(=O)$_2$R$^e$, —S(=O)$_2$NR$^f$R$^g$, —C(O)OR$^h$, —C(O)R$^e$, —N(R$^b$)C(O)NR$^f$R$^g$, —N(R$^b$)S(=O)$_2$R$^e$, —N(R$^b$)S(=O)$_2$NR$^f$R$^g$, and —NR$^f$R$^g$;

each R$^d$ is selected from the group consisting of optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^b{}_2$)$_n$ aryl, optionally substituted —(CR$^b{}_2$)$_n$ cycloalkyl, optionally substituted —(CR$^b{}_2$)$_n$ heterocycloalkyl, and —C(O)NR$^f$R$^g$;

each R$^e$ is selected from the group consisting of optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^a{}_2$)$_n$ aryl, optionally substituted —(CR$^a{}_2$)$_n$ cycloalkyl, and optionally substituted —(CR$^a{}_2$)$_n$ heterocycloalkyl;

R$^f$ and R$^g$ are each independently selected from the group consisting of hydrogen, optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^b{}_2$)$_n$ aryl, optionally substituted —(CR$^b{}_2$)$_n$ cycloalkyl, and optionally substituted —(CR$^b{}_2$)$_n$ heterocycloalkyl, or R$^f$ and R$^g$ may together form an optionally substituted heterocyclic ring, which may contain a second heterogroup selected from the group consisting of O, NR$^c$, and S, wherein said optionally substituted heterocyclic ring may be substituted with 0-4 substituents selected from the group consisting of optionally substituted —C$_1$-C$_4$ alkyl, —OR$^b$, oxo, cyano, —CF$_3$, optionally substituted phenyl, and —C(O)OR$^h$;

each R$^h$ is selected from the group consisting of optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^b{}_2$)$_n$ aryl, optionally substituted —(CR$^b{}_2$)$_n$ cycloalkyl, and optionally substituted —(CR$^b{}_2$)$_n$ heterocycloalkyl;

R$^5$ is selected from the group consisting of —OH, optionally substituted —OC$_1$-C$_6$ alkyl, OC(O)R$^e$, —OC(O)OR$^h$, —F, —NHC(O)R$^e$, —NHS(=O)R$^e$, —NHS(=O)$_2$R$^e$, —NHC(=S)NH(R$^h$), and —NHC(O)NH(R$^h$);

X is P(O)YR$^{11}$Y'R$^{11}$;

Y and Y' are each independently selected from the group consisting of —O—, and —NR$^v$—; when Y and Y' are —O—, R$^{11}$ attached to —O— is independently selected from the group consisting of —H, alkyl, optionally substituted aryl, optionally substituted heterocycloalkyl, optionally substituted CH$_2$-heterocycloalkyl wherein the cyclic moiety contains a carbonate or thiocarbonate, optionally substituted-alkylaryl, —C(R$^z$)$_2$OC(O)NR$^z{}_2$, —NR$^z$—C(O)—R$^y$, —C(R$^z$)$_2$—OC(O)R$^y$, —C(R$^z$)$_2$—O—C(O)OR$^y$, —C(R$^z$)$_2$OC(O)SR$^y$, -alkyl-S—C(O)R$^y$, -alkyl-S—S-alkylhydroxy, and -alkyl-S—S—S-alkylhydroxy;

when Y and Y' are —NR$^v$—, then R$^{11}$ attached to —NR$^v$— is independently selected from the group consisting of —H, —[C(R$^z$)$_2$]$_q$—COOR$^y$, —C(R$^x$)$_2$COOR$^Y$, —[C(R$^z$)$_2$]$_q$—C(O)SR$^y$, and -cycloalkylene-COOR$^y$;

when Y is —O— and Y' is NR$^v$, then R$^{11}$ attached to —O— is independently selected from the group consisting of —H, alkyl, optionally substituted aryl, optionally substituted heterocycloalkyl, optionally substituted CH$_2$-heterocycloakyl wherein the cyclic moiety contains a carbonate or thiocarbonate, optionally substituted-alkylaryl, —C(R$^z$)$_2$OC(O)NR$^z{}_2$, —NR$^z$—C(O)R$^y$, —C(R$^z$)$_2$—OC(O)R$^y$, —C(R$^z$)$_2$—O—C(O)OR$^y$, —C(R$^z$)$_2$OC(O)SR$^y$, -alkyl-S—C(O)R$^y$, -alkyl-S—S-alkylhydroxy, and -alkyl-S—S—S-alkylhydroxy; and R$^{11}$ attached to —NR$^v$— is independently selected from the group consisting of H, —[C(R$^z$)$_2$]$_q$—COOR$^y$, —C(R$^x$)$_2$COOR$^y$, —[C(R$^z$)$_2$]$_q$—C(O)SR$^y$, and -cycloalkylene-COOR$^y$;

or when Y and Y' are independently selected from —O— and NR$^v$, then together R$^{11}$ and R$^{11}$ are-alkyl-S—S-alkyl- to form a cyclic group, or together R$^{11}$ and R$^{11}$ are the group:

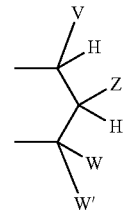

wherein:
V, W, and W' are independently selected from the group consisting of hydrogen, optionally substituted alkyl, optionally substituted aralkyl, heterocycloalkyl, aryl, substituted aryl, heteroaryl, substituted heteroaryl, optionally substituted 1-alkenyl, and optionally substituted 1-alkynyl;

or together V and Z are connected via an additional 3-5 atoms to form a cyclic group containing 5-7 atoms, wherein 0-1 atoms are heteroatoms and the remaining atoms are carbon, substituted with hydroxy, acyloxy, alkylthiocarbonyloxy, alkoxycarbonyloxy, or aryloxycarbonyloxy attached to a carbon atom that is three atoms from both Y groups attached to the phosphorus;

or together V and Z are connected via an additional 3-5 atoms to form a cyclic group, wherein 0-1 atoms are heteroatoms and the remaining atoms are carbon, that is fused to an aryl group at the beta and gamma position to the Y attached to the phosphorus;

or together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus;

or together Z and W are connected via an additional 3-5 atoms to form a cyclic group, wherein 0-1 atoms are heteroatoms and the remaining atoms are carbon, and V must be aryl, substituted aryl, heteroaryl, or substituted heteroaryl;

or together W and W' are connected via an additional 2-5 atoms to form a cyclic group, wherein 0-2 atoms are heteroatoms and the remaining atoms are carbon, and V must be aryl, substituted aryl, heteroaryl, or substituted heteroaryl;

Z is selected from the group consisting of —CHR$^z$OH, —CHR$^z$OC(O)R$^y$, —CHR$^z$OC(S)R$^y$, —CHR$^z$OC(S)OR$^y$, —CHR$^z$OC(O)SR$^y$, —CHR$^z$OCO$_2$R$^y$, —OR$^z$—, —SR$^z$, —CHR$^z$N$_3$, —CH$_2$-aryl, —CH(aryl)OH, —CH(CH=CR$^z_2$)OH, —CH(C≡CR$^z$)OH, —R$^z$, —NR$^z_2$, —OCOR$^y$, —OCO$_2$R$^y$, —SCOR$^y$, —SCO$_2$R$^y$, —NHCOR$^z$, —NHCO$_2$R$^z$, —CH$_2$NH-aryl, —(CH$_2$)q-OR$^z$, and —(CH$_2$)q-SR$^z$;

q is an integer 2 or 3;

each R$^z$ is selected from the group consisting of R$^y$ and —H;

each R$^y$ is selected from the group consisting of alkyl, aryl, heterocycloalkyl, and aralkyl;

each R$^x$ is independently selected from the group consisting of —H, and alkyl, or together R$^x$ and R$^x$ form a cyclic alkyl group; and each R$^v$ is selected from the group consisting of —H, lower alkyl, acyloxyalkyl, alkoxycarbonyloxyalkyl, and lower acyl.

In some embodiments, the compound to be administered comprises one or more of the compounds having a structures selected from the group consisting of:

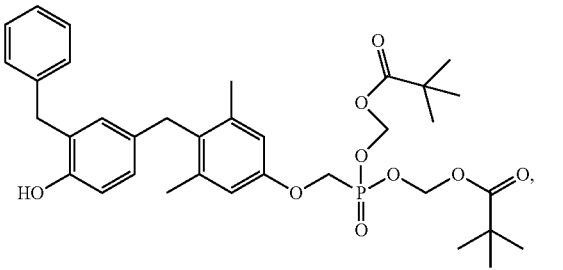

(Compound 1)

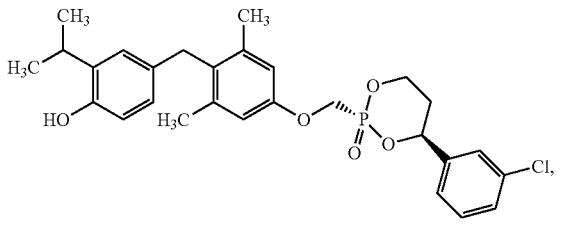

(Compound 2)

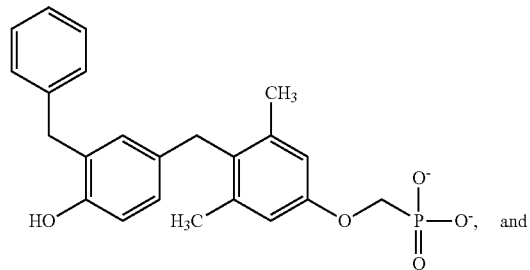

(Compound 3)

and

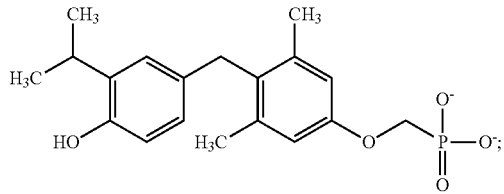

(Compound 4)

or pharmaceutically acceptable salts thereof.

In some embodiments, the glycogen storage disease comprises one or more of Glycogen storage disease types 1, 2, 3, 4, 5, 6, 7, 8, 9, 10, 11, or 12, including those diseases known as aglycogenosis, von Gierke disease, Pompe disease, Cori disease, Forbes disease, limit dextrinosis, debranching enzyme disease, Andersen disease, glycogen phosphorylase deficiency, brancher deficiency, amylopectinosis, glycogen branching enzyme deficiency, McArdle disease, Hers disease, Tarui disease, autosomal liver and muscle phosphorylase kinase deficiency, autosomal liver phosphorylase kinase deficiency, X-linked liver phosphorylase kinase deficiency, GSD X, Fanconi-Bickel syndrome, or aldolase A deficiency. In some embodiments, the glycogen storage disease may comprise any disorder marked by inability to store or metabolize glycogen in the tissues of the body, or by the abnormal accumulation of glycogen, lipids, fatty acids, or triglycerides within the tissues of the body. In some embodiments, administration of the compounds according to the present disclosure provides an amelioration of a glycogen storage defect. In some embodiments, administration of the compounds according to the present disclosure provides an amelioration of a symptom of a glycogen storage disease, such as elevated serum or tissue lipids.

In some embodiments, administration of the compounds of the present disclosure leads to a reduction in serum lipid, serum triglyceride, serum fatty acid, or serum cholesterol levels in a patient having a glycogen storage defect or suffering from a glycogen storage disease. In some further embodiments, administration of the compounds as described herein leads to the amelioration of hepatic steatosis, hypercholesterolemia, or hepatic inflammation associated with a glycogen storage disease. In some embodiments, administration of the compounds as described herein leads to the amelioration of cardiomegaly, hepatomegaly, liver steatosis, hyperlipidemia, hypercholesterolemia, increased ALT, increased AST, increased serum triglycerides, liver fibrosis, cirrhosis, hepatocellular adenoma, or hepatocellular carcinoma associated with a glycogen storage disease.

In some embodiments, the methods according to the present disclosure comprise administration of a second therapeutic agent. In some further embodiments, said second therapeutic agent may comprise one or more of a starch, a sugar, an amino acid, a peptide, an enzyme, a gene therapy, or any combination thereof. In some further embodiments, said second therapeutic agent may comprise one or more of corn starch, potato starch, wheat starch, vegetable starch, or cassava, or any combination thereof. In some further embodiments, said second therapeutic agent may comprise one or more of glucose, galactose, fructose, sucrose, maltose, lactose, arabinose, or other sugars, or any combination thereof. In some further embodiments, said second therapeutic agent may also comprise one or more of alglucosidase alfa, a glucose-6-phosphatase, a debranching enzyme, a glycogen synthase, a glucose-6-phosphatase translocase, a phosphatase translocase, an alpha-1-4-glucosidase, an amylo-1-6-glucosidase, an amylo-1,4-to-1,6-transglucosidase, a glycogen phosphorylase, a phosphofructokinase, a cyclic-3',5' AMP-dependent kinase, a type 2 glucose transporter, an aldolase A, or any combination thereof. In some further embodiments, said second therapeutic agent may comprise one or more of an insulin, an insulin-like peptide, a glucagon, a glucagon-like peptide, or any combination thereof. In some further embodiments, said compound may be administered in association with a liver, kidney, or bone marrow transplant. In some embodiments, the compounds of the present disclosure may be coadministered with or administered in association with any one of the aforementioned treatments or second therapeutic agents, or any combination thereof.

DETAILED DESCRIPTION

Figure 1:
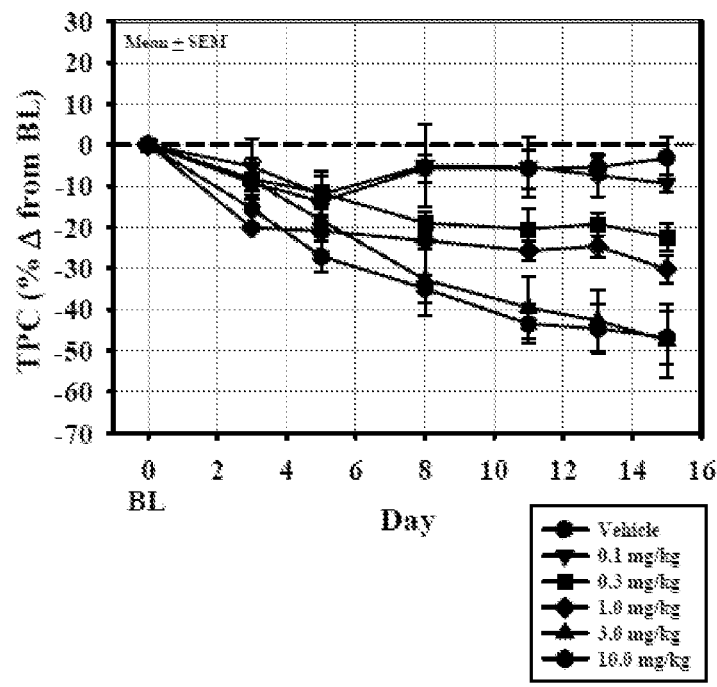
FIG. 1 shows the effect of once-daily oral administration of Compound 2 on total plasma cholesterol (TPC) levels in beagle dogs (n=4 per group) over 14 days.

The present disclosure provides compounds and methods for treating glycogen storage diseases by administering thyroid hormone receptor-β (TRβ) agonists. In some embodiments, such diseases further comprise the symptoms of hepatic steatosis, hyperlipidemia, dyslipidemia, hypertriglyceridemia, fibrosis, cirrhosis, hepatocellular adenoma, hepatocellular carcinoma, and other hepatic and non-hepatic symptoms which may be affected by interventions within the TRβ pathway.

Definitions

The term "mammal" is used in its usual biological sense. Thus, it specifically includes humans and non-human mammals such as dogs, cats, horses, donkeys, mules, cows, domestic buffaloes, camels, llamas, alpacas, bison, yaks, goats, sheep, pigs, elk, deer, domestic antelopes, and non-human primates as well as many other species.

"Subject" as used herein, means a human or a non-human mammal including but not limited to a dog, cat, horse, donkey, mule, cow, domestic buffalo, camel, llama, alpaca, bison, yak, goat, sheep, pig, elk, deer, domestic antelope, or a non-human primate selected for treatment or therapy.

"Subject suspected of having" means a subject exhibiting one or more clinical indicators of a disease or condition. In certain embodiments, the disease or condition is a glycogen storage disease. In certain embodiments, the disease or condition is hyperlipidemia. In certain embodiments, the disease or condition is hypercholesterolemia. In certain embodiments, the disease or condition is diabetes. In certain embodiments, the disease or condition is non-alcoholic fatty liver disease. In certain embodiments, the disease or condition is non-alcoholic steatohepatitis. In certain embodiments, the disease or condition is atherosclerosis. In certain embodiments, the disease or condition is cardiovascular disease.

"Glycogen storage disease" means any one or more of a group of disorders marked by dysfunction in the synthesis, transport, or utilization of glycogen, generally due to the loss of a necessary enzyme activity. Glycogen storage diseases are generally classified by type according to their symptoms and etiologies. Known types include GSD type 0 (aglycogenesis, glycogen synthase deficiency); GSD type 1 (von Gierke disease, glucose-6-phosphatase translocase/transporter deficiency); GSD type 2 (Pompe disease, alpha-1-4-glucosidase deficiency); GSD type 3 (Cori disease, Forbes disease, limit dextrinosis, debranching enzyme disease; amylo-1,6-glucosidase deficiency due to loss of glucosidase, and/or transferase activity); GSD type 4 (Andersen disease, glycogen phosphorylase deficiency, brancher deficiency, amylopectinosis, glycogen branching enzyme deficiency; amylo-1,4 to 1,6 transglucosidase deficiency); GSD type 5 (McArdle disease; glycogen phosphorylase (muscle type) deficiency); GSD type 6 (Hers disease; glycogen phosphorylase E (liver type) deficiency); GSD type 7 (Tarui disease; phosphofructokinase deficiency); GSD type 8, 9 (GSD with phosphorylase activation system defects; phosphorylase kinase (liver or muscle isoforms) deficiency); GSD type 10 (cyclic AMP-dependent kinase deficiency); GSD type 11 (Fanconi-Bickel syndrome; glucose transporter type 2 (GLUT2) deficiency); and GSD type 12 (aldolase A deficiency). Subtypes of glycogen storage diseases are also known, in particular GSD 1a, which results from mutations in the gene for glucose-6-phosphatase (G6PC) and leads to, among other symptoms, the excess accumulation of glycogen and lipids in liver tissue, hepatomegaly, hepatic adenomas, and hepatocellular carcinoma.

Symptoms of glycogen storage diseases may include elevated or reduced blood sugar, insulin insensitivity, myopathies, as well as hepatic symptoms such as steatosis, hyperlipidemia, hypercholesterolemia, cardiomegaly, hepatomegaly, fibrosis, cirrhosis, hepatocellular adenoma, and hepatocellular carcinoma. Symptoms may also include insulin insensitivity, elevated or reduced blood glucose, and renal dysfunction.

"Subject in need thereof" means a subject identified as in need of a therapy or treatment.

A therapeutic effect relieves, to some extent, one or more of the symptoms of a disease or disorder, and includes curing the disease or disorder. "Curing" means that the symptoms of active disease are eliminated. However, certain long-term or permanent effects of the disease may exist even after a cure is obtained (such as extensive tissue damage).

"Treat," "treatment," or "treating," as used herein refers to administering a pharmaceutical composition for prophylactic and/or therapeutic purposes. The term "prophylactic treatment" refers to treating a patient who does not yet have the relevant disease or disorder, but who is susceptible to, or otherwise at risk of, a particular disease or disorder, whereby the treatment reduces the likelihood that the patient will develop the disease or disorder. The term "therapeutic treatment" refers to administering treatment to a patient already having a disease or disorder.

"Preventing" or "prevention" refers to delaying or forestalling the onset, development or progression of a condition or disease for a period of time, including weeks, months, or years.

"Amelioration" means a lessening of severity of at least one indicator of a condition or disease. In certain embodiments, amelioration includes a delay or slowing in the progression of one or more indicators of a condition or disease. The severity of indicators may be determined by subjective or objective measures which are known to those skilled in the art.

"Modulation" means a perturbation of function or activity. In certain embodiments, modulation means an increase in gene expression. In certain embodiments, modulation means a decrease in gene expression. In certain embodiments, modulation means an increase or decrease in total serum levels of a specific protein. In certain embodiments, modulation means an increase or decrease in free serum levels of a specific protein. In certain embodiments, modulation means an increase or decrease in total serum levels of a specific non-protein factor. In certain embodiments, modulation means an increase or decrease in free serum levels of a specific non-protein factor. In certain embodiments, modulation means an increase or decrease in total bioavailability of a specific protein. In certain embodiments, modulation means an increase or decrease in total bioavailability of a specific non-protein factor.

"Administering" means providing a pharmaceutical agent or composition to a subject, and includes, but is not limited to, administering by a medical professional and self-administering.

Administration of the compounds disclosed herein or the pharmaceutically acceptable salts thereof can be via any of the accepted modes of administration for agents that serve similar utilities including, but not limited to, orally, subcutaneously, intravenously, intranasally, topically, transdermally, intraperitoneally, intramuscularly, intrapulmonarilly, vaginally, rectally, or intraocularly. Oral and parenteral administrations are customary in treating the indications that are the subject of the preferred embodiments.

"Parenteral administration," means administration through injection or infusion. Parenteral administration includes, but is not limited to, subcutaneous administration, intravenous administration, intramuscular administration, intraarterial administration, and intracranial administration.

"Subcutaneous administration" means administration just below the skin.

"Intravenous administration" means administration into a vein.

"Intraarterial administration" means administration into an artery.

The term "agent" includes any substance, molecule, element, compound, entity, or a combination thereof. It includes, but is not limited to, e.g., protein, polypeptide, peptide or mimetic, small organic molecule, polysaccharide, polynucleotide, and the like. It can be a natural product, a synthetic compound, or a chemical compound, or a combination of two or more substances.

"Pharmaceutical agent" means a substance that provides a therapeutic effect when administered to a subject.

"Pharmaceutical composition" means a mixture of substances suitable for administering to an individual that includes a pharmaceutical agent. For example, a pharmaceutical composition may comprise a modified oligonucleotide and a sterile aqueous solution.

"Active pharmaceutical ingredient" means the substance in a pharmaceutical composition that provides a desired effect.

The term "pharmaceutically acceptable salt" refers to salts that retain the biological effectiveness and properties of the compounds with which they are associated and, which are not biologically or otherwise undesirable. In many cases, the compounds herein are capable of forming acid and/or base salts by virtue of the presence of phenol and/or phosphonate groups or groups similar thereto. One of ordinary skill in the art will be aware that the protonation state of any or all of these compounds may vary with pH and ionic character of the surrounding solution, and thus the present disclosure contemplates multiple charge states of each compound. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297, Johnston et al., published Sep. 11, 1987 (incorporated by reference herein in its entirety).

"Solvate" refers to the compound formed by the interaction of a solvent and an EPI, a metabolite, or salt thereof. Suitable solvates are pharmaceutically acceptable solvates including hydrates.

Compounds

In some embodiments, the TRβ agonists for use as described herein include compounds according to Formula I:

Formula I:

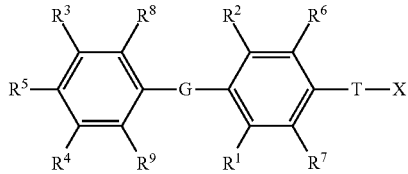

wherein:
G is selected from the group consisting of —O—, —S—, —S(=O)—, —S(=O)$_2$—, —Se—, —CH$_2$—, —CF$_2$—, —CHF—, —C(O)—, —CH(OH)—, —CH(C$_1$-C$_4$ alkyl)-, —CH(C$_1$-C$_4$ alkoxy)-, —C(=CH$_2$)—, —NH—, and —N(C$_1$-C$_4$ alkyl)-;
T is selected from the group consisting of —(CR$^a_2$)$_k$-, —CR$^b$=CR$^b$—(CR$^a_2$)$_n$—, —(CR$^a_2$)$_n$—CR$^b$=CR$^b$—, —(CR$^a_2$)—CR$^b$=CR$^b$—(CR$^a_2$)—, —O(CR$^b_2$)(CR$^a_2$)$_n$—, —S(CR$^b_2$)(CR$^a_2$)$_n$—, N(R$^c$)(CR$^b_2$)(CR$^a_2$)$_n$—, N(R$^b$)C(O)(CR$^a_2$)$_n$—, —C(O)(CR$^a_2$)$_m$—, —(CR$^a_2$)$_m$C(O)—, —(CR$^a_2$)C(O)(CR$^a_2$)$_n$, —(CR$^b_2$)$_n$C(O)(CR$^a_2$)—, and —C(O)NH(CR$^b_2$)(CR$^a_2$)$_p$—;
k is an integer from 1-4;
m is an integer from 0-3;
n is an integer from 0-2;
p is an integer from 0-1;
each R$^a$ is independently selected from the group consisting of hydrogen, optionally substituted —C$_1$-C$_4$ alkyl, halogen, —OH, optionally substituted —O—C$_1$-C$_4$ alkyl, —OCF$_3$, optionally substituted —S—C$_1$-C$_4$ alkyl, —NR$^b$R$^c$, optionally substituted —C$_2$-C$_4$ alkenyl, and optionally substituted —C$_2$-C$_4$ alkynyl; with the proviso that when one R$^a$ is attached to C through an O, S, or N atom, then the other R$^a$ attached to the same C is a hydrogen, or attached via a carbon atom;
each R$^b$ is independently selected from the group consisting of hydrogen and optionally substituted —C$_1$-C$_4$ alkyl;
each R$^c$ is independently selected from the group consisting of hydrogen and optionally substituted —C$_1$-C$_4$ alkyl, optionally substituted —C(O)—C$_1$-C$_4$ alkyl, and —C(O)H;
R$^1$, and R$^2$ are each independently selected from the group consisting of halogen, optionally substituted —C$_1$-C$_4$ alkyl, optionally substituted —S—C$_1$-C$_3$ alkyl, optionally substituted —C$_2$-C$_4$ alkenyl, optionally substituted —C$_2$-C$_4$ alkynyl, —CF$_3$, —OCF$_3$, optionally substituted —O—C$_1$-C$_3$ alkyl, and cyano;
R$^6$, R$^7$, R$^8$, and R$^9$ are each independently selected from the group consisting of are each independently selected from the group consisting of hydrogen, halogen, optionally substituted —C C$_1$-C$_4$ alkyl, optionally substituted —S—C$_1$-C$_3$ alkyl, optionally substituted —C$_2$-C$_4$ alkenyl, optionally substituted —C$_2$-C$_4$ alkynyl, —CF$_3$, —OCF$_3$, optionally substituted-O—C$_1$-C$_3$ alkyl, and cyano; or R$^6$ and T are taken together along with the carbons they are attached to form a ring of 5 to 6 atoms including 0 to 2 heteroatoms independently selected from —NR$^i$—, —O—, and —S—, with the proviso that when there are 2 heteroatoms in the ring and both heteroatoms are different than nitrogen then both heteroatoms have to be separated by at least one carbon atom; and X is attached to this ring by a direct bond to a ring carbon, or by —(CR$^a_2$)— or —C(O)— bonded to a ring carbon or a ring nitrogen;
R$^i$ is selected from the group consisting of hydrogen, —C(O)C$_1$-C$_4$ alkyl, —C$_1$-C$_4$ alkyl, and —C$_1$-C$_4$— aryl;
R$^3$ and R$^4$ are independently selected from the group consisting of hydrogen, halogen, —CF$_3$, —OCF$_3$, cyano, optionally substituted —C$_1$-C$_{12}$ alkyl, optionally substituted —C$_2$-C$_{12}$ alkenyl, optionally substituted —C$_2$-C$_{12}$ alkynyl, —SR$^d$, —S(=O)R$^e$, —S(=O)$_2$R$^e$, —S(=O)$_2$NR$^f$R$^g$, —C(O)OR$^h$, —C(O)R$^e$, —N(R$^b$)C(O)NR$^f$R$^g$, —N(R$^b$)S(=O)$_2$R$^e$, —N(R$^b$)S(=O)$_2$NR$^f$R$^g$, and —NR$^f$R$^g$;
each R$^d$ is selected from the group consisting of optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^b_2$)$_n$ aryl, optionally substituted —(CR$^b_2$)$_n$ cycloalkyl, optionally substituted —(CR$^b_2$)$_n$ heterocycloalkyl, and —C(O)NR$^f$R$^g$;
each R$^e$ is selected from the group consisting of optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^a_2$)$_n$ aryl, optionally substituted —(CR$^a_2$) cycloalkyl, and optionally substituted —(CR$^a_2$)$_n$ heterocycloalkyl;
R$^f$ and R$^g$ are each independently selected from the group consisting of hydrogen, optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^b_2$)$_n$ aryl, optionally substituted —(CR$^b_2$)$_n$ cycloalkyl, and optionally substituted —(CR$^b_2$)$_n$ heterocycloalkyl, or R$^f$ and R$^g$ may together form an optionally substituted heterocyclic ring, which may contain a second heterogroup selected from the group consisting of O, NR$^C$, and S, wherein said optionally substituted heterocyclic ring may be substituted with 0-4 substituents selected from the group consisting of optionally substituted —C$_1$-C$_4$ alkyl, —OR$^b$, oxo, cyano, —CF$_3$, optionally substituted phenyl, and —C(O)OR$^h$;
each R$^h$ is selected from the group consisting of optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^b_2$)$_n$ aryl, optionally substituted —(CR$^b_2$)$_n$ cycloalkyl, and optionally substituted —(CR$^b_2$)$_n$ heterocycloalkyl;
R$^5$ is selected from the group consisting of —OH, optionally substituted —OC$_1$-C$_6$ alkyl, OC(O)R$^e$, —OC(O)OR$^h$, —F, —NHC(O)R$^e$, —NHS(=O)R$^e$, —NHS(=O)$_2$R$^e$, —NHC(=S)NH(R$^h$), and —NHC(O)NH(R$^h$);
X is P(O)YR$^{11}$Y'R$^{11}$;
Y and Y' are each independently selected from the group consisting of —O—, and —NR$^v$—; when Y and Y' are —O—, R$^{11}$ attached to —O— is independently selected from the group consisting of —H, alkyl, optionally substituted aryl, optionally substituted heterocycloalkyl, optionally substituted CH$_2$-heterocycloakyl wherein the cyclic moiety contains a carbonate or thiocarbonate, optionally substituted-alkylaryl, —C(R$^z$)$_2$OC(O)NR$^z_2$, —NR$^z$—C(O)—R$^y$, —C(R$^z$)$_2$—OC(O)R$^y$, —C(R$^z$)$_2$—O—C(O)OR$^y$, —C(R$^z$)$_2$OC(O)SR$^y$, -alkyl-S—C(O)R$^y$, -alkyl-S—S-alkylhydroxy, and -alkyl-S—S—S-alkylhydroxy;

when Y and Y' are —NR$^v$—, then R$^{11}$ attached to —NR$^v$— is independently selected from the group consisting of —H, —[C(R$^z$)$_2$]$_q$—COOR$^y$, —C(R$^x$)$_2$COOR$^Y$, —[C(R$^z$)$_2$]$_q$—C(O)SR$^y$, and -cycloalkylene-COOR$^y$;

when Y is —O— and Y' is NR$^v$, then R$^{11}$ attached to —O— is independently selected from the group consisting of —H, alkyl, optionally substituted aryl, optionally substituted heterocycloalkyl, optionally substituted CH$_2$-heterocycloakyl wherein the cyclic moiety contains a carbonate or thiocarbonate, optionally substituted-alkylaryl, —C(R$^z$)$_2$OC(O)NR$^z$$_2$, —NR$^z$—C(O)—R$^y$, —C(R$^z$)$_2$—OC(O)R$^y$, —C(R$^z$)$_2$—O—C(O)OR$^y$, —C(R$^z$)$_2$OC(O)SR$^y$, -alkyl-S—C(O)R$^y$, -alkyl-S—S-alkylhydroxy, and -alkyl-S—S—S-alkylhydroxy; and R$^{11}$ attached to —NR$^v$— is independently selected from the group consisting of H, —[C(R$^z$)$_2$]$_q$—COOR$^y$, —C(R$^x$)$_2$COOR$^y$, —[C(R$^z$)$_2$]$_q$—C(O)SR$^y$, and -cycloalkylene-COOR$^y$;

or when Y and Y' are independently selected from —O— and NR$^v$, then together R$^{11}$ and R$^{11}$ are-alkyl-S—S-alkyl- to form a cyclic group, or together R$^{11}$ and R$^{11}$ are the group:

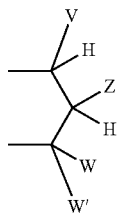

wherein:
V, W, and W' are independently selected from the group consisting of hydrogen, optionally substituted alkyl, optionally substituted aralkyl, heterocycloalkyl, aryl, substituted aryl, heteroaryl, substituted heteroaryl, optionally substituted 1-alkenyl, and optionally substituted 1-alkynyl;

or together V and Z are connected via an additional 3-5 atoms to form a cyclic group containing 5-7 atoms, wherein 0-1 atoms are heteroatoms and the remaining atoms are carbon, substituted with hydroxy, acyloxy, alkylthiocarbonyloxy, alkoxycarbonyloxy, or aryloxycarbonyloxy attached to a carbon atom that is three atoms from both Y groups attached to the phosphorus;

or together V and Z are connected via an additional 3-5 atoms to form a cyclic group, wherein 0-1 atoms are heteroatoms and the remaining atoms are carbon, that is fused to an aryl group at the beta and gamma position to the Y attached to the phosphorus;

or together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus;

or together Z and W are connected via an additional 3-5 atoms to form a cyclic group, wherein 0-1 atoms are heteroatoms and the remaining atoms are carbon, and V must be aryl, substituted aryl, heteroaryl, or substituted heteroaryl;

or together W and W' are connected via an additional 2-5 atoms to form a cyclic group, wherein 0-2 atoms are heteroatoms and the remaining atoms are carbon, and V must be aryl, substituted aryl, heteroaryl, or substituted heteroaryl;

Z is selected from the group consisting of —CHR$^z$OH, —CHR$^z$OC(O)R$^y$, —CHR$^z$OC(S)R$^y$, —CHR$^z$OC(S)OR$^y$, —CHR$^z$OC(O)SR$^y$, —CHR$^z$OCO$_2$R$^y$, —OR$^z$, —SR$^z$, —CHR$^z$N$_3$, —CH$_2$-aryl, —CH(aryl)OH, —CH(CH=CR$^z$$_2$)OH, —CH(C≡CR$^z$)OH, —R$^z$, —NR$^z$$_2$, —OCOR$^y$, —OCO$_2$R$^y$, —SCOR$^y$, —SCO$_2$R$^y$, —NHCOR$^z$, —NHCO$_2$R$^y$, —CH$_2$NH-aryl, (CH$_2$)q-OR$^z$, and —(CH$_2$)q-SR$^z$;

q is an integer 2 or 3;
each R$^z$ is selected from the group consisting of R$^y$ and —H;
each R$^y$ is selected from the group consisting of alkyl, aryl, heterocycloalkyl, and aralkyl;
each R$^x$ is independently selected from the group consisting of —H, and alkyl, or together R$^x$ and R$^x$ form a cyclic alkyl group;
each R$^v$ is selected from the group consisting of —H, lower alkyl, acyloxyalkyl, alkoxycarbonyloxyalkyl, and lower acyl;

and pharmaceutically acceptable salts thereof.

In some embodiments, the compound of Formula I has the following provisos:
a) when G is —O—, T is —CH$_2$—, R$^1$ and R$^2$ are each bromo, R$^3$ is iso-propyl, R$^4$ is hydrogen, and R$^5$ is —OH, then X is not P(O)(OH)$_2$ or P(O)(OCH$_2$CH$_3$)$_2$;
b) V, Z, W, W' are not all —H; and
c) when Z is —R$^z$, then at least one of V, W, and W' is not —H, alkyl, aralkyl, or heterocycloalkyl;
d) when G is —O—, T is (CH$_2$)$_{1-4}$—, R$^1$ and R$^2$ are independently halogen, alkyl, and cycloalkyl, R$^3$ is alkyl, R$^4$ is hydrogen, and R$^5$ is —OH, then X is not —P(O)(OH)$_2$ or —P(O)(O-lower alkyl)$_2$; and
e) when G is —O—, R$^5$ is —NHC(O)R$^e$, —NHS(=O)$_{1-2}$R$^e$, —NHC(S)NH(R$^b$), or —NHC(O)NH(R$^h$), T is —(CH$_2$)$^m$—, —CH=CH—, —O(CH$_2$)$_{1-2}$, or —NH(CH$_2$)$_{1-2}$—, then X is not —P(O)(OH)$_2$ or —P(O)(OH)NH$_2$;

In some embodiments, the compound is selected from one or more of the following:

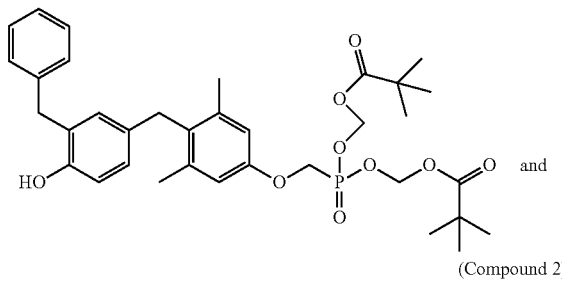

(Compound 1)

and

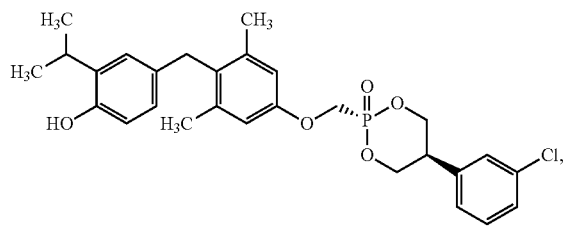

(Compound 2)

(Compound 3)
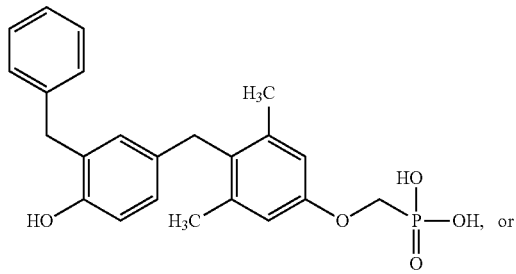
or
(Compound 4)
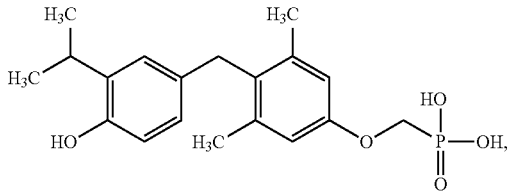
or pharmaceutically acceptable salts thereof.
In other embodiments, the compound is selected from:
| Structure | Compound Number |
|---|---|
| 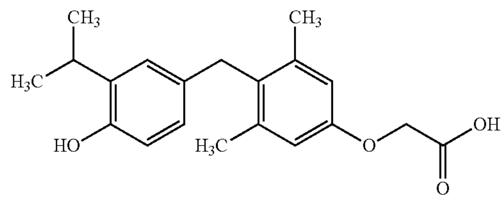 [SMILES: Cc1cc(OCC(=O)O)cc(C)c1Cc1ccc(O)c(C(C)C)c1] | 17 |
| 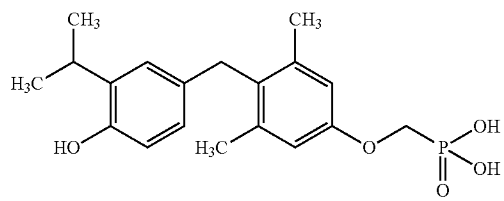 [SMILES: Cc1cc(OCP(=O)(O)O)cc(C)c1Cc1ccc(O)c(C(C)C)c1] | 7 |
| 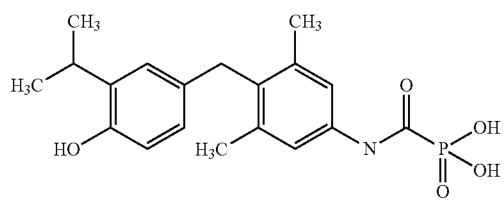 [SMILES: Cc1cc(NC(=O)P(=O)(O)O)cc(C)c1Cc1ccc(O)c(C(C)C)c1] | 1a |
| 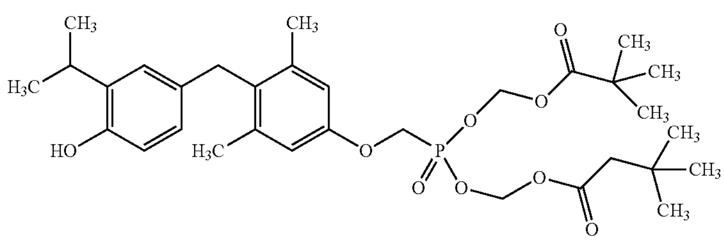 [SMILES: Cc1cc(OCP(=O)(OCOC(=O)CC(C)(C)C)OCOC(=O)C(C)(C)C)cc(C)c1Cc1ccc(O)c(C(C)C)c1] | 12-1 |
| 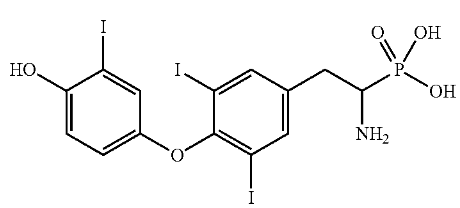 [SMILES: NC(Cc1cc(I)c(Oc2ccc(O)c(I)c2)c(I)c1)P(=O)(O)O] | 2a |
| 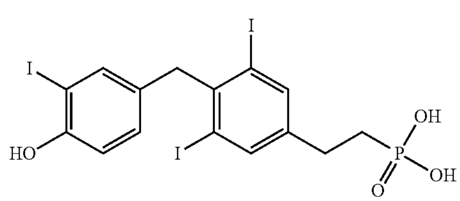 [SMILES: O=P(O)(O)CCc1cc(I)c(Cc2ccc(O)c(I)c2)c(I)c1] | 3a |

-continued

| Structure | Compound Number |
|---|---|
| (structure) | 4a |
| (structure) | 5 |
| (structure) | 6 |
| (structure) | 8 |
| (structure) | 9 |
| (structure) | 11 |
| (structure) | 10 |

| Structure | Compound Number |
|---|---|
| | cis-13-1 |
| | trans-13-1 Chiral |
| | cis-13-6 Chiral |
| | cis-13-2 Chiral |
| | trans-13-2 Chiral |

| Structure | Compound Number |
|---|---|
| | cis-13-3 Chiral |
| | trans-13-3 Chiral |
| 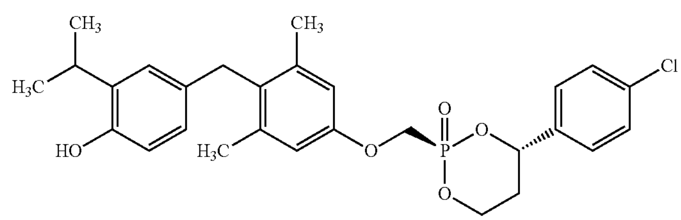 [SMILES: Cc1cc(OC[P@]2(=O)OCC[C@@H](c3ccc(Cl)cc3)O2)cc(C)c1Cc1ccc(O)c(C(C)C)c1] | trans-13-6 |
| 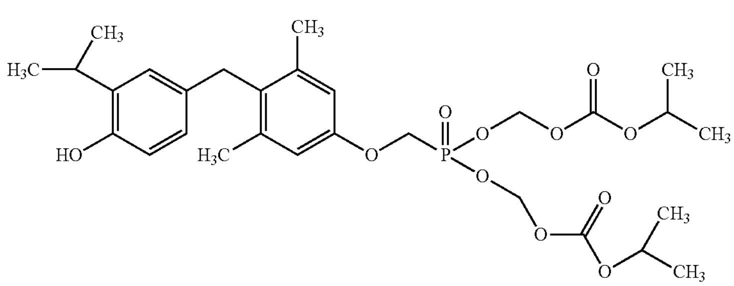 [SMILES: Cc1cc(OCP(=O)(OCOC(=O)OC(C)C)OCOC(=O)OC(C)C)cc(C)c1Cc1ccc(O)c(C(C)C)c1] | 12-3 |
| 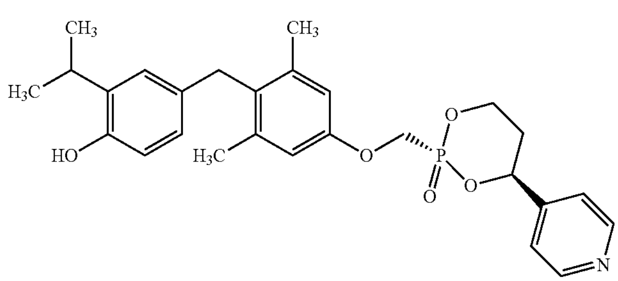 [SMILES: Cc1cc(OC[P@]2(=O)OCC[C@@H](c3ccncc3)O2)cc(C)c1Cc1ccc(O)c(C(C)C)c1] | trans-13-5 |

-continued

| Structure | Compound Number |
|---|---|
| | cis-13-5 Chiral |
| | trans-13-7 Chiral |
| | trans-13-4 Chiral |
| | cis-13-4 Chiral |
| | 12-2 Chiral |

-continued

| Structure | Compound Number |
|---|---|
| 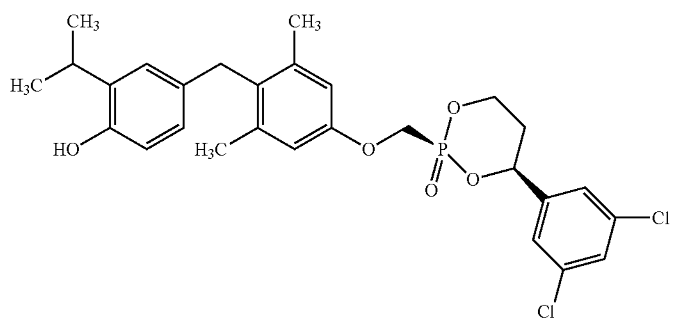 [SMILES: Cc1cc(OC[P@@]2(=O)OCC[C@@H](c3cc(Cl)cc(Cl)c3)O2)cc(C)c1Cc1ccc(O)c(C(C)C)c1] | cis-13-7 |
| 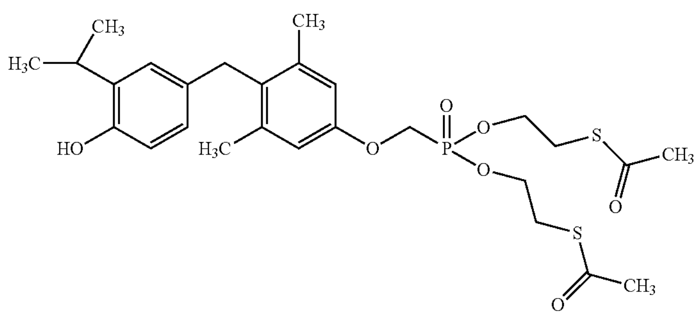 [SMILES: CC(=O)SCCOP(=O)(COc1cc(C)c(Cc2ccc(O)c(C(C)C)c2)c(C)c1)OCCSC(C)=O] | 14 |
| 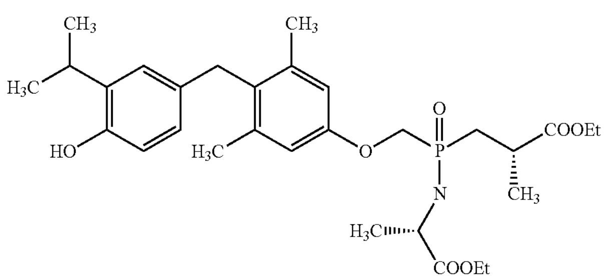 [SMILES: CCOC(=O)[C@H](C)CP(=O)(COc1cc(C)c(Cc2ccc(O)c(C(C)C)c2)c(C)c1)N[C@@H](C)C(=O)OCC] | 15-1 |
| 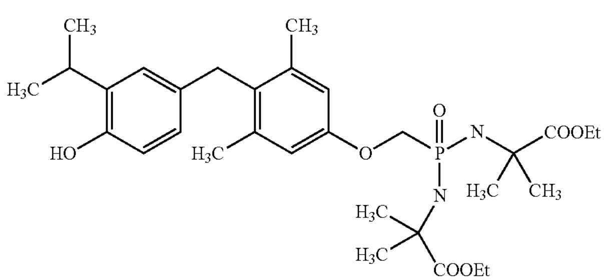 [SMILES: CCOC(=O)C(C)(C)NP(=O)(COc1cc(C)c(Cc2ccc(O)c(C(C)C)c2)c(C)c1)NC(C)(C)C(=O)OCC] | 15-2 |
| 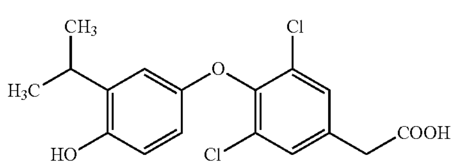 [SMILES: CC(C)c1cc(Oc2c(Cl)cc(CC(=O)O)cc2Cl)ccc1O] | 18 |
| 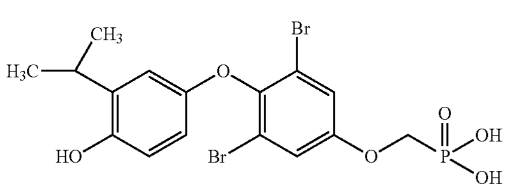 [SMILES: CC(C)c1cc(Oc2c(Br)cc(OCP(=O)(O)O)cc2Br)ccc1O] | 8-1 |

-continued

| Structure | Compound Number |
|---|---|
| 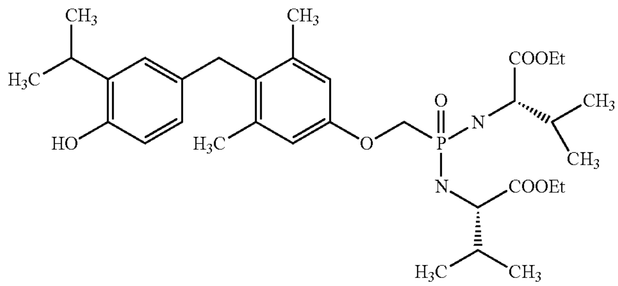 [SMILES: CCOC(=O)[C@@H](NP(=O)(COc1cc(C)c(Cc2ccc(O)c(C(C)C)c2)c(C)c1)N[C@H](C(=O)OCC)C(C)C)C(C)C] | 15-3 |
| 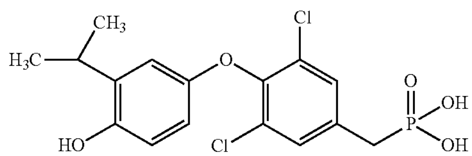 | 19 |
| 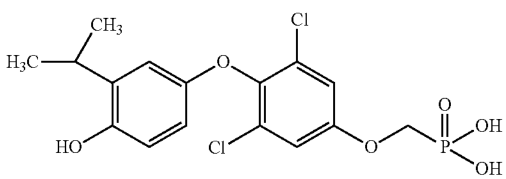 | 8-2 |
| 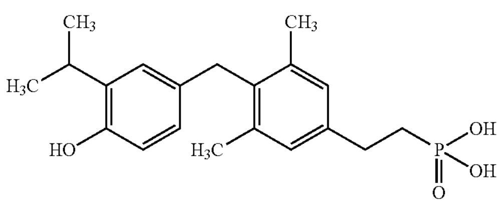 [SMILES: Cc1cc(CCP(=O)(O)O)cc(C)c1Cc1ccc(O)c(C(C)C)c1] | 24-1 |
| 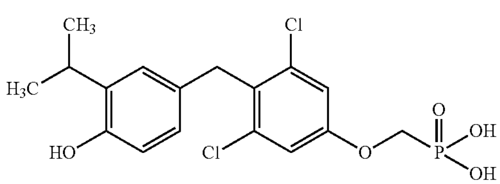 [SMILES: CC(C)c1cc(Cc2c(Cl)cc(OCP(=O)(O)O)cc2Cl)ccc1O] | 7-5 |
| 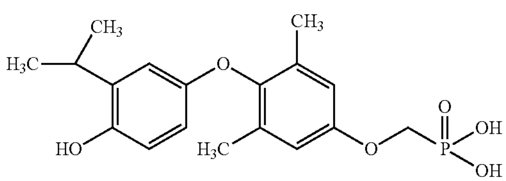 [SMILES: Cc1cc(OCP(=O)(O)O)cc(C)c1Oc1ccc(O)c(C(C)C)c1] | 25 |
| 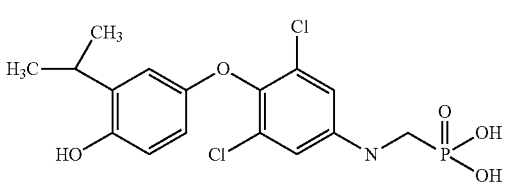 | 22 |
| 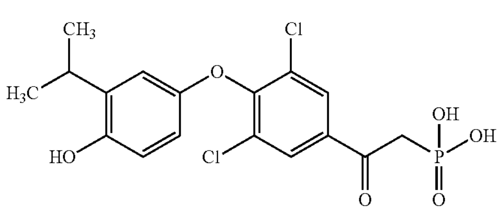 [SMILES: CC(C)c1cc(Oc2c(Cl)cc(C(=O)CP(=O)(O)O)cc2Cl)ccc1O] | 21 |

-continued

| Structure | Compound Number |
|---|---|
| 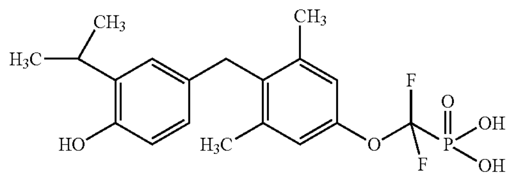 [SMILES: Cc1cc(OC(F)(F)P(=O)(O)O)cc(C)c1Cc1ccc(O)c(C(C)C)c1] | 7-6 |
| 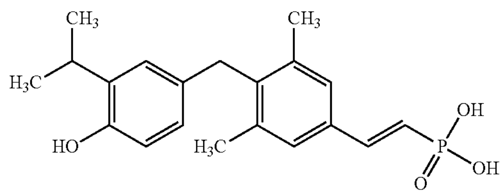 [SMILES: Cc1cc(/C=C/P(=O)(O)O)cc(C)c1Cc1ccc(O)c(C(C)C)c1] | 24-2 |
| 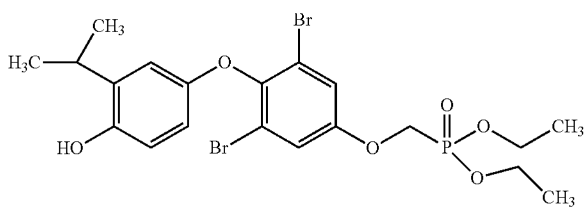 [SMILES: CCOP(=O)(COc1cc(Br)c(Oc2ccc(O)c(C(C)C)c2)c(Br)c1)OCC] | 19-1 |
| 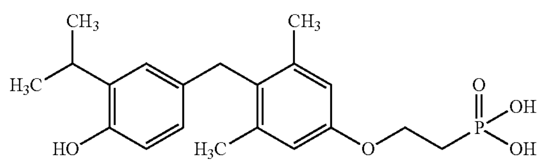 [SMILES: Cc1cc(OCCP(=O)(O)O)cc(C)c1Cc1ccc(O)c(C(C)C)c1] | 26 |
| 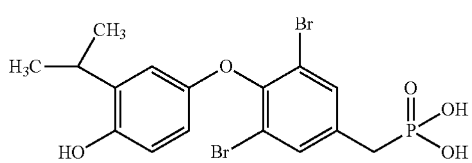 [SMILES: CC(C)c1cc(Oc2c(Br)cc(CP(=O)(O)O)cc2Br)ccc1O] | 19-2 |
| 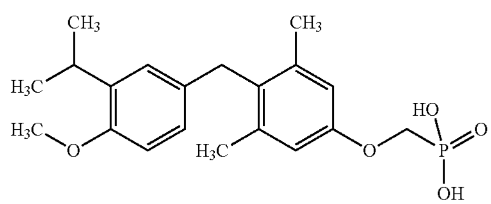 [SMILES: COc1ccc(Cc2c(C)cc(OCP(=O)(O)O)cc2C)cc1C(C)C] | 7-4 |
| 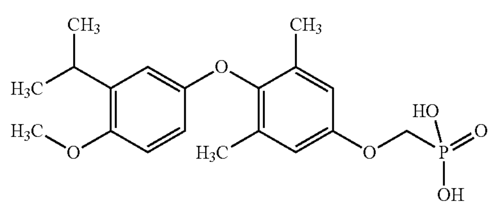 [SMILES: COc1ccc(Oc2c(C)cc(OCP(=O)(O)O)cc2C)cc1C(C)C] | 30 |
| 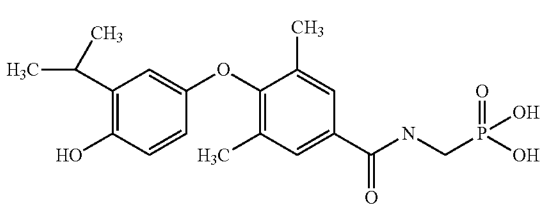 [SMILES: Cc1cc(C(=O)NCP(=O)(O)O)cc(C)c1Oc1ccc(O)c(C(C)C)c1] | 23 |

-continued

| Structure | Compound Number |
|---|---|
| 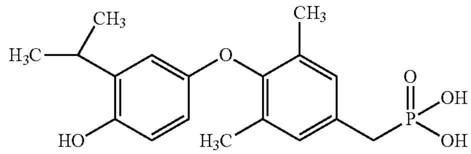 [SMILES: Cc1cc(CP(=O)(O)O)cc(C)c1Oc1ccc(O)c(C(C)C)c1] | 19-3 |
| 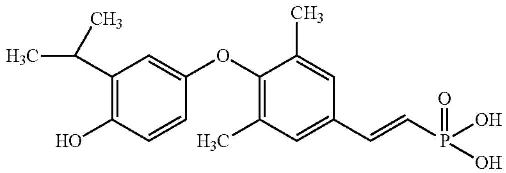 [SMILES: Cc1cc(/C=C/P(=O)(O)O)cc(C)c1Oc1ccc(O)c(C(C)C)c1] | 28 |
| 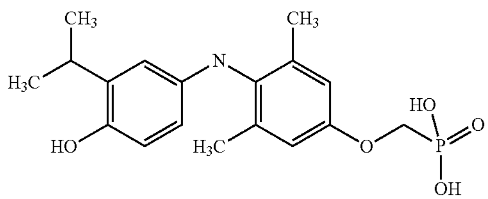 [SMILES: Cc1cc(OCP(=O)(O)O)cc(C)c1Nc1ccc(O)c(C(C)C)c1] | 20 |
| 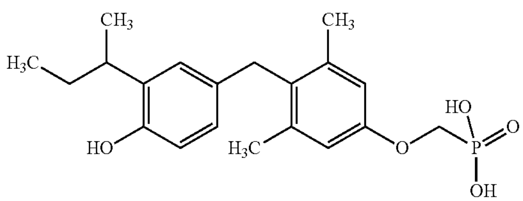 [SMILES: CCC(C)c1cc(Cc2c(C)cc(OCP(=O)(O)O)cc2C)ccc1O] | 7-3 |
| 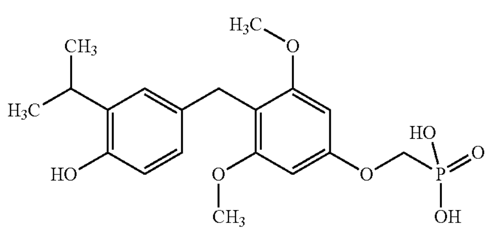 [SMILES: COc1cc(OCP(=O)(O)O)cc(OC)c1Cc1ccc(O)c(C(C)C)c1] | 7-2 |
| 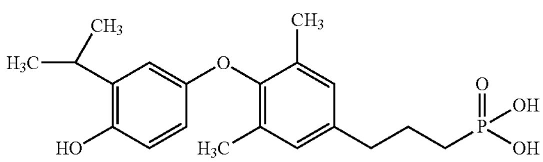 [SMILES: Cc1cc(CCCP(=O)(O)O)cc(C)c1Oc1ccc(O)c(C(C)C)c1] | 29 |
| 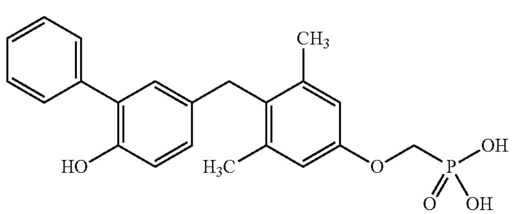 [SMILES: Cc1cc(OCP(=O)(O)O)cc(C)c1Cc1ccc(O)c(-c2ccccc2)c1] | 7-1 |
| 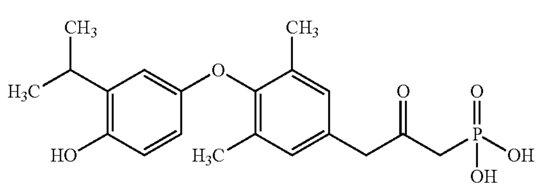 [SMILES: Cc1cc(CC(=O)CP(=O)(O)O)cc(C)c1Oc1ccc(O)c(C(C)C)c1] | 32 |

| Structure | Compound Number |
|---|---|
| 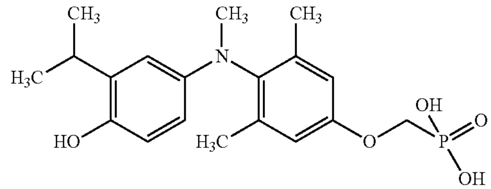 [SMILES: Cc1cc(OCP(=O)(O)O)cc(C)c1N(C)c1ccc(O)c(C(C)C)c1] | 20-1 |
| 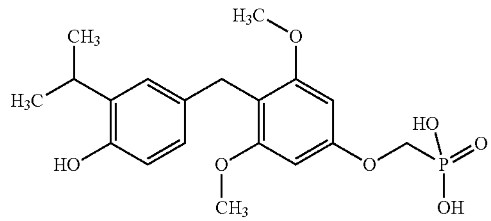 [SMILES: COc1cc(OCP(=O)(O)O)cc(OC)c1Cc1ccc(O)c(C(C)C)c1] | 24 |
| 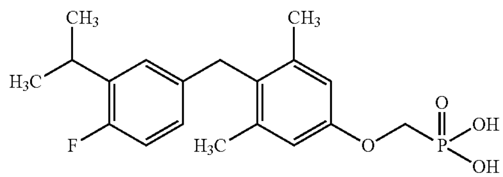 [SMILES: Cc1cc(OCP(=O)(O)O)cc(C)c1Cc1ccc(F)c(C(C)C)c1] | 27 |
| 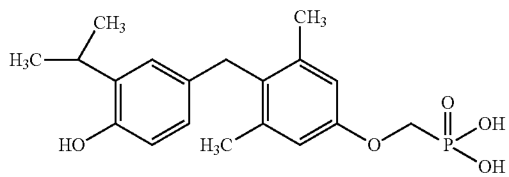 [SMILES: Cc1cc(OCP(=O)(O)O)cc(C)c1Cc1ccc(O)c(C(C)C)c1] | 31 |
| 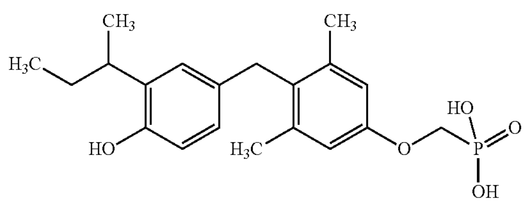 [SMILES: CCC(C)c1cc(Cc2c(C)cc(OCP(=O)(O)O)cc2C)ccc1O] | 24-3 |
| 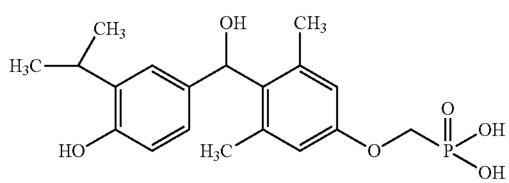 [SMILES: Cc1cc(OCP(=O)(O)O)cc(C)c1C(O)c1ccc(O)c(C(C)C)c1] | 33 |
| 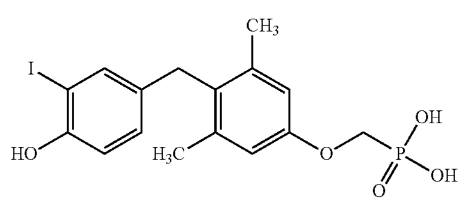 [SMILES: Cc1cc(OCP(=O)(O)O)cc(C)c1Cc1ccc(O)c(I)c1] | 34 |
| 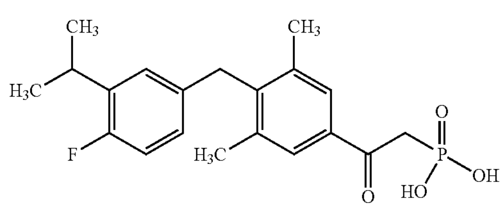 [SMILES: Cc1cc(C(=O)CP(=O)(O)O)cc(C)c1Cc1ccc(F)c(C(C)C)c1] | 41-2 |

-continued

| Structure | Compound Number |
|---|---|
| 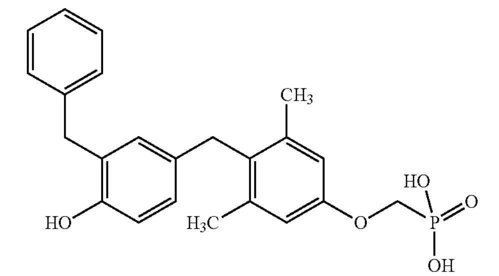 [SMILES: Cc1cc(OCP(=O)(O)O)cc(C)c1Cc1ccc(O)c(Cc2ccccc2)c1] | 38 |
| 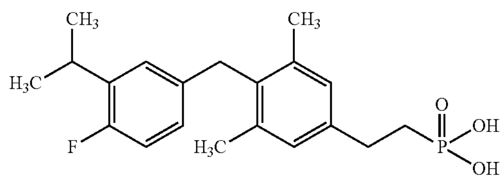 [SMILES: Cc1cc(CCP(=O)(O)O)cc(C)c1Cc1ccc(F)c(C(C)C)c1] | 42-2 |
| 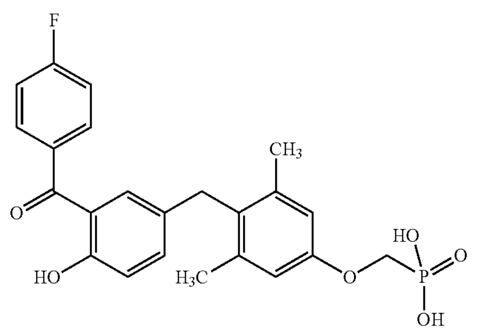 [SMILES: Cc1cc(OCP(=O)(O)O)cc(C)c1Cc1ccc(O)c(C(=O)c2ccc(F)cc2)c1] | 39 |
| 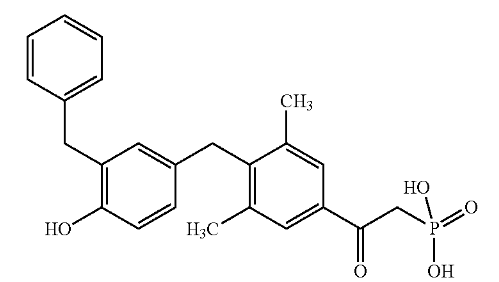 [SMILES: Cc1cc(C(=O)CP(=O)(O)O)cc(C)c1Cc1ccc(O)c(Cc2ccccc2)c1] | 41 |
| 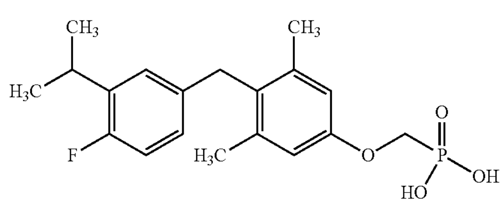 [SMILES: Cc1cc(OCP(=O)(O)O)cc(C)c1Cc1ccc(F)c(C(C)C)c1] | 27-2 |
| 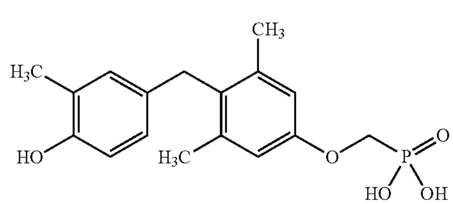 [SMILES: Cc1cc(Cc2c(C)cc(OCP(=O)(O)O)cc2C)ccc1O] | 7-7 |

| Structure | Compound Number |
|---|---|
| 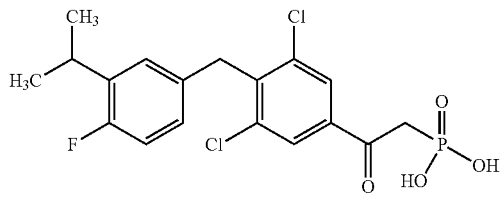 [SMILES: CC(C)c1cc(Cc2c(Cl)cc(C(=O)CP(=O)(O)O)cc2Cl)ccc1F] | 41-3 |
| 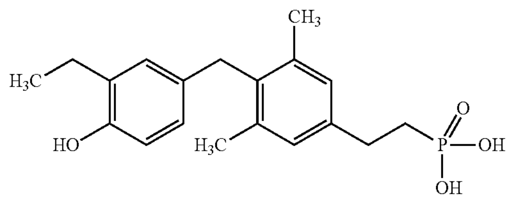 [SMILES: CCc1cc(Cc2c(C)cc(CCP(=O)(O)O)cc2C)ccc1O] | 24-4 |
| 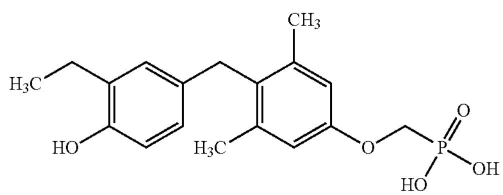 [SMILES: CCc1cc(Cc2c(C)cc(OCP(=O)(O)O)cc2C)ccc1O] | 7-8 |
| 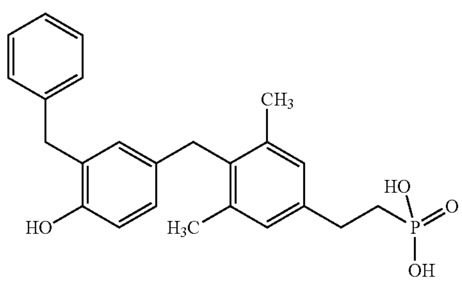 [SMILES: Cc1cc(CCP(=O)(O)O)cc(C)c1Cc1ccc(O)c(Cc2ccccc2)c1] | 42 |
| 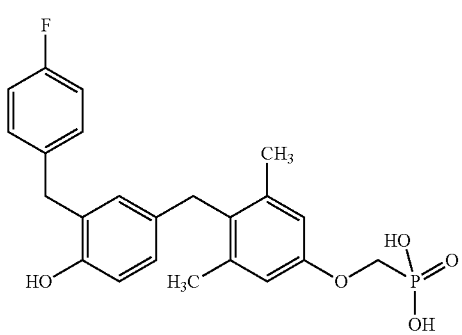 [SMILES: Cc1cc(OCP(=O)(O)O)cc(C)c1Cc1ccc(O)c(Cc2ccc(F)cc2)c1] | 40 |
| 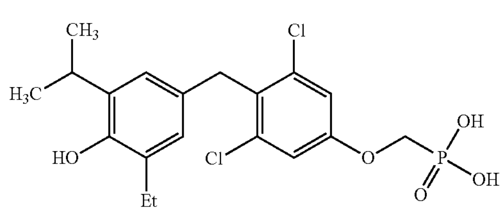 [SMILES: CCc1cc(Cc2c(Cl)cc(OCP(=O)(O)O)cc2Cl)cc(C(C)C)c1O] | 7-14 |

-continued

| Structure | Compound Number |
|---|---|
| (structure) | 7-9 |
| (structure) | 35 |
| (structure) | 37 |
| (structure) | 36 |
| (structure) | 7-12 |
| (structure) | 7-11 |
| (structure) | 7-13 |

-continued

| Structure | Compound Number |
|---|---|
| 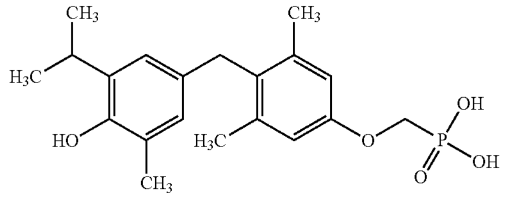 [SMILES: Cc1cc(Cc2c(C)cc(OCP(=O)(O)O)cc2C)cc(C(C)C)c1O] | 7-10 |
| 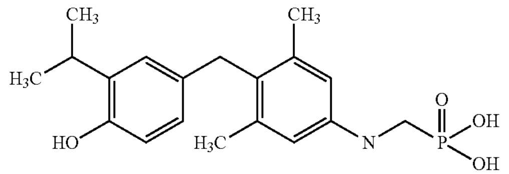 [SMILES: Cc1cc(NCP(=O)(O)O)cc(C)c1Cc1ccc(O)c(C(C)C)c1] | 47 |
| 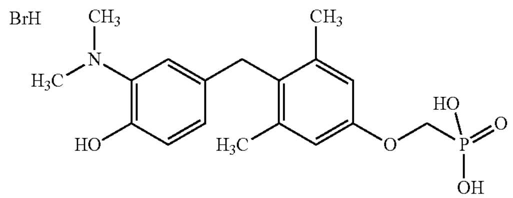 [SMILES: Br ; Cc1cc(OCP(=O)(O)O)cc(C)c1Cc1ccc(O)c(N(C)C)c1] | 49 |
| 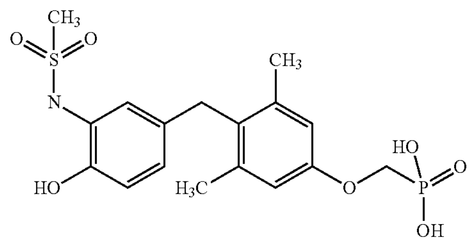 [SMILES: Cc1cc(OCP(=O)(O)O)cc(C)c1Cc1ccc(O)c(NS(C)(=O)=O)c1] | 51-1 |
| 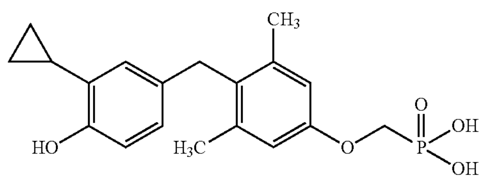 [SMILES: Cc1cc(OCP(=O)(O)O)cc(C)c1Cc1ccc(O)c(C2CC2)c1] | 48 |
| 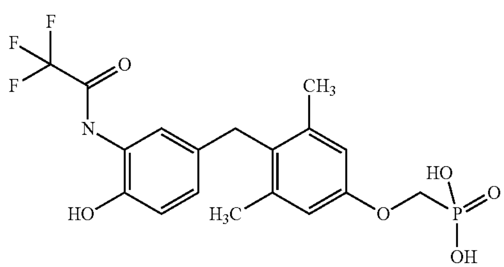 [SMILES: Cc1cc(OCP(=O)(O)O)cc(C)c1Cc1ccc(O)c(NC(=O)C(F)(F)F)c1] | 51-2 |
| 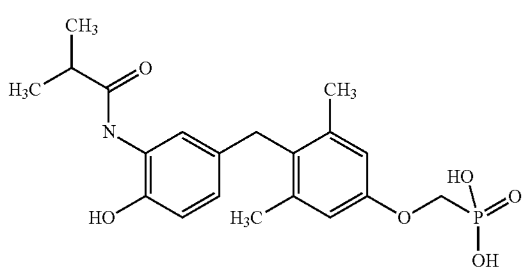 [SMILES: Cc1cc(OCP(=O)(O)O)cc(C)c1Cc1ccc(O)c(NC(=O)C(C)C)c1] | 51-3 |

-continued

| Structure | Compound Number |
|---|---|
| 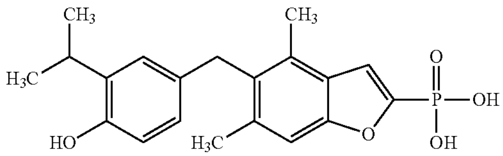 [SMILES: Cc1cc2oc(P(=O)(O)O)cc2c(C)c1Cc1ccc(O)c(C(C)C)c1] | 45 |
| 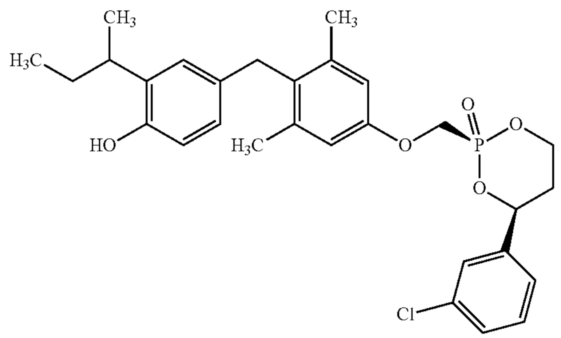 [SMILES: CCC(C)c1cc(Cc2c(C)cc(OC[P@@]3(=O)OCC[C@@H](c4cccc(Cl)c4)O3)cc2C)ccc1O] | 13-8 |
| 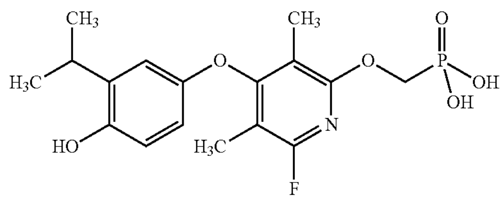 [SMILES: Cc1c(F)nc(OCP(=O)(O)O)c(C)c1Oc1ccc(O)c(C(C)C)c1] | 57 |
| 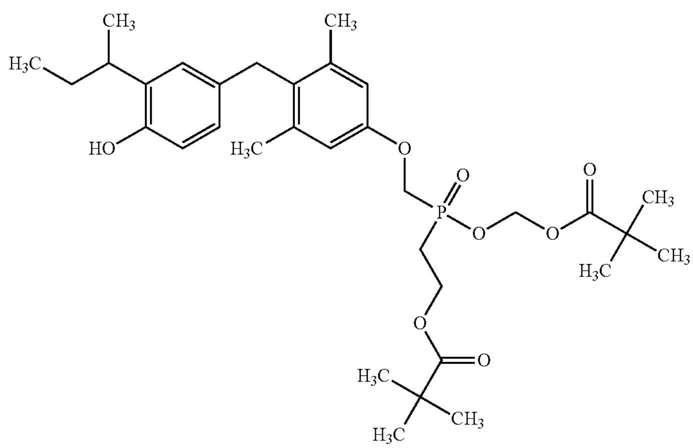 [SMILES: CCC(C)c1cc(Cc2c(C)cc(OCP(=O)(CCOC(=O)C(C)(C)C)OCOC(=O)C(C)(C)C)cc2C)ccc1O] | 12-4 |
| 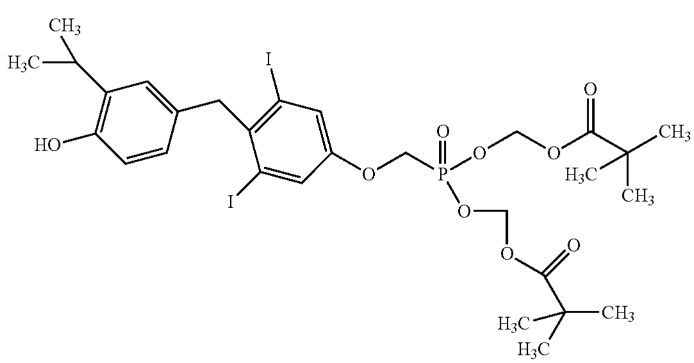 [SMILES: CC(C)c1cc(Cc2c(I)cc(OCP(=O)(OCOC(=O)C(C)(C)C)OCOC(=O)C(C)(C)C)cc2I)ccc1O] | 12-7 |

-continued
| Structure | Compound Number |
|---|---|
| 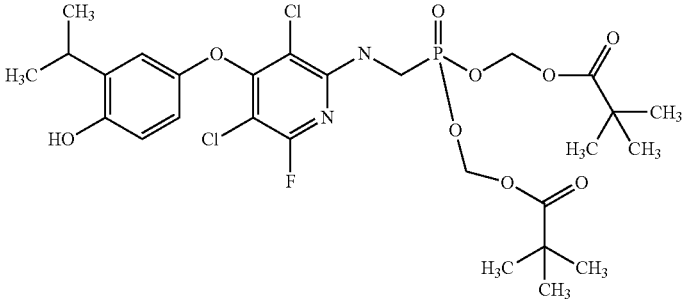 [SMILES: CC(C)c1cc(Oc2c(Cl)c(F)nc(NCP(=O)(OCOC(=O)C(C)(C)C)OCOC(=O)C(C)(C)C)c2Cl)ccc1O] | 12-9 |
| 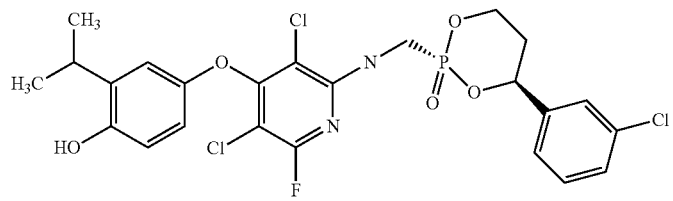 [SMILES: CC(C)c1cc(Oc2c(Cl)c(F)nc(NC[P@]3(=O)OCC[C@@H](c4cccc(Cl)c4)O3)c2Cl)ccc1O] | 13-12-trans |
| 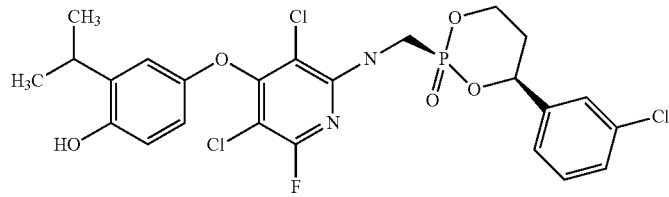 [SMILES: CC(C)c1cc(Oc2c(Cl)c(F)nc(NC[P@@]3(=O)OCC[C@@H](c4cccc(Cl)c4)O3)c2Cl)ccc1O] | 13-12-cis |
| 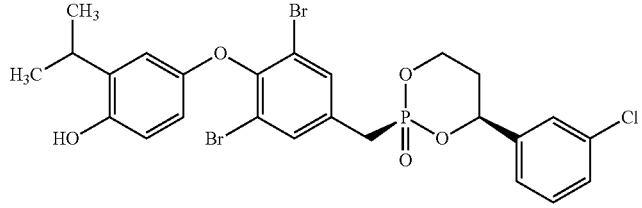 [SMILES: CC(C)c1cc(Oc2c(Br)cc(C[P@@]3(=O)OCC[C@@H](c4cccc(Cl)c4)O3)cc2Br)ccc1O] | 13-9 |
| 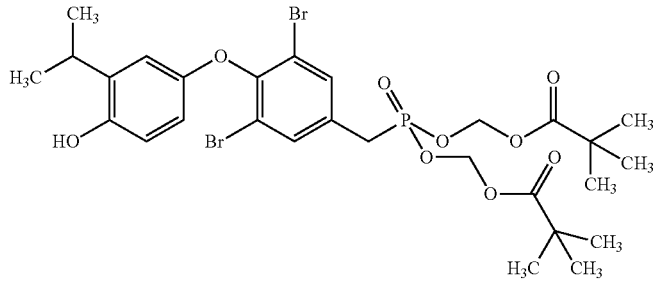 [SMILES: CC(C)c1cc(Oc2c(Br)cc(CP(=O)(OCOC(=O)C(C)(C)C)OCOC(=O)C(C)(C)C)cc2Br)ccc1O] | 12-5 |
| 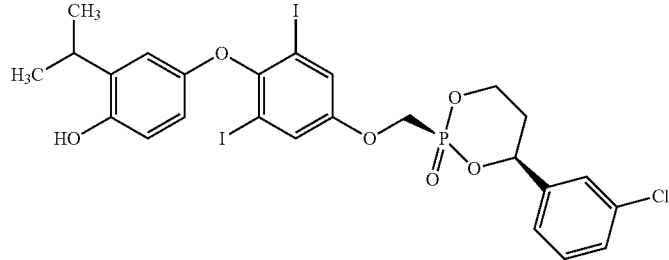 [SMILES: CC(C)c1cc(Oc2c(I)cc(OC[P@@]3(=O)OCC[C@@H](c4cccc(Cl)c4)O3)cc2I)ccc1O] | 13-10 |

-continued

| Structure | Compound Number |
|---|---|
| 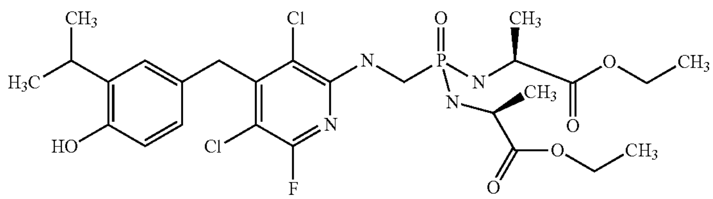 [SMILES: CCOC(=O)[C@H](C)NP(=O)(CNc1nc(F)c(Cl)c(Cc2ccc(O)c(C(C)C)c2)c1Cl)N[C@@H](C)C(=O)OCC] | 15-6 |
| 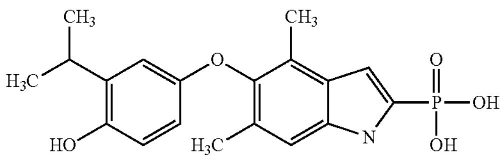 [SMILES: Cc1cc2[nH]c(P(=O)(O)O)cc2c(C)c1Oc1ccc(O)c(C(C)C)c1] | 66 |
| 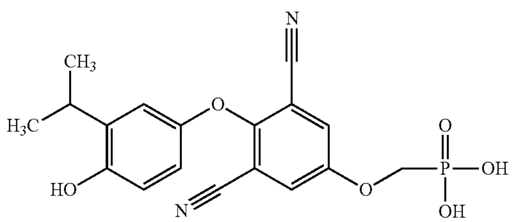 [SMILES: CC(C)c1cc(Oc2c(C#N)cc(OCP(=O)(O)O)cc2C#N)ccc1O] | 56 |
| 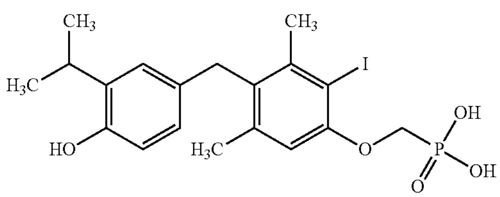 [SMILES: Cc1cc(OCP(=O)(O)O)c(I)c(C)c1Cc1ccc(O)c(C(C)C)c1] | 46 |
| 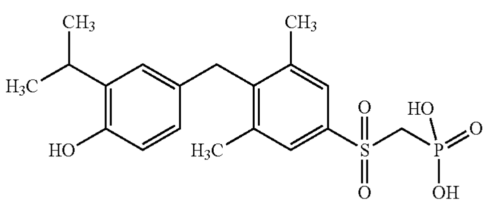 [SMILES: Cc1cc(S(=O)(=O)CP(=O)(O)O)cc(C)c1Cc1ccc(O)c(C(C)C)c1] | 52 |
| 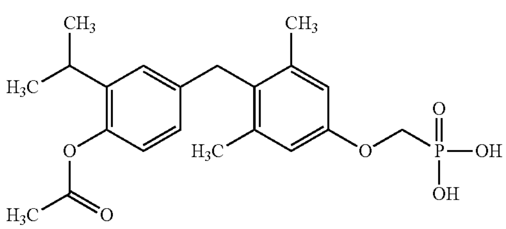 [SMILES: CC(=O)Oc1ccc(Cc2c(C)cc(OCP(=O)(O)O)cc2C)cc1C(C)C] | 58 |
| 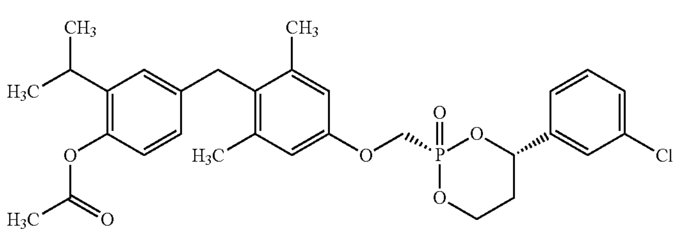 [SMILES: CC(=O)Oc1ccc(Cc2c(C)cc(OC[P@@]3(=O)OCC[C@@H](c4cccc(Cl)c4)O3)cc2C)cc1C(C)C] | 59 |

-continued
| Structure | Compound Number |
|---|---|
| 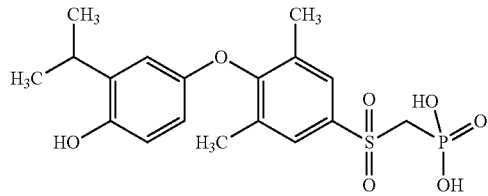 | 53 |
| 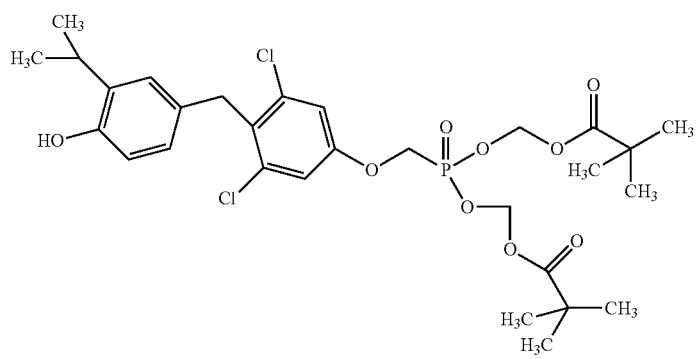 [SMILES: CC(C)c1cc(Cc2c(Cl)cc(OCP(=O)(OCOC(=O)C(C)(C)C)OCOC(=O)C(C)(C)C)cc2Cl)ccc1O] | 12-8 |
| 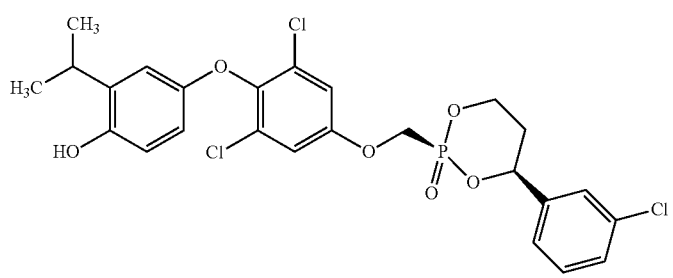 | 13-11 |
| 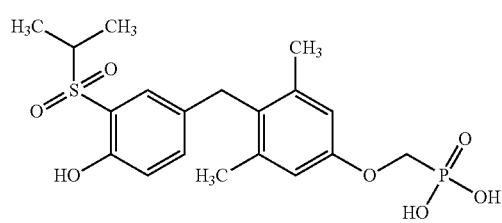 [SMILES: Cc1cc(OCP(=O)(O)O)cc(C)c1Cc1ccc(O)c(S(=O)(=O)C(C)C)c1] | 44 |
| 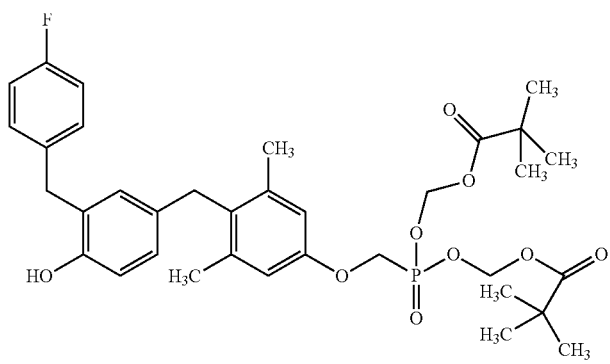 [SMILES: Cc1cc(OCP(=O)(OCOC(=O)C(C)(C)C)OCOC(=O)C(C)(C)C)cc(C)c1Cc1ccc(O)c(Cc2ccc(F)cc2)c1] | 12-6 |

-continued

| Structure | Compound Number |
|---|---|
| (structure) | 15-5 |
| (structure) | 15-4 |
| (structure) | 15-7 |
| (structure) | 65-1 |
| (structure) | 54 |

-continued

| Structure | Compound Number |
|---|---|
| 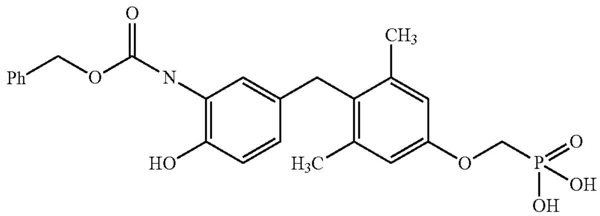 [SMILES: Cc1cc(OCP(=O)(O)O)cc(C)c1Cc1ccc(O)c(NC(=O)OCc2ccccc2)c1] | 50 |
| 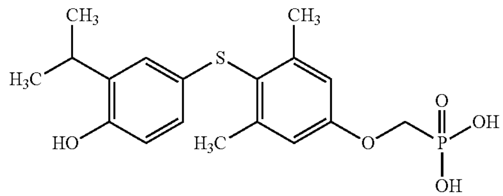 [SMILES: Cc1cc(OCP(=O)(O)O)cc(C)c1Sc1ccc(O)c(C(C)C)c1] | 43 |
| 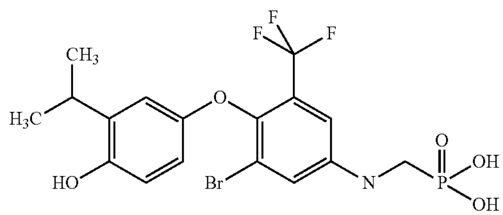 [SMILES: CC(C)c1cc(Oc2c(Br)cc(NCP(=O)(O)O)cc2C(F)(F)F)ccc1O] | 63 |
| 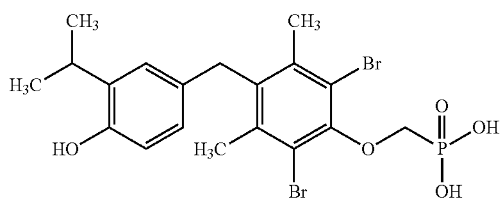 [SMILES: Cc1c(Br)c(OCP(=O)(O)O)c(Br)c(C)c1Cc1ccc(O)c(C(C)C)c1] | 65-2 |
| 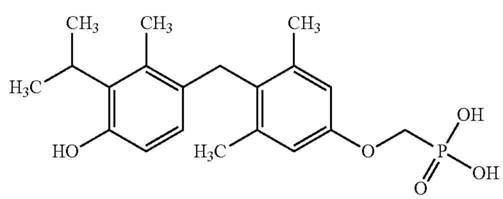 [SMILES: Cc1cc(OCP(=O)(O)O)cc(C)c1Cc1ccc(O)c(C(C)C)c1C] | 7-16 |
| 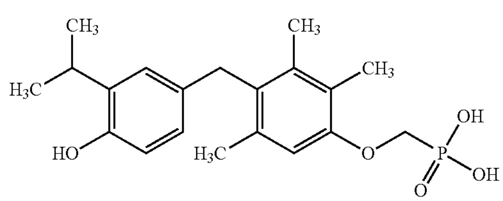 [SMILES: Cc1cc(OCP(=O)(O)O)c(C)c(C)c1Cc1ccc(O)c(C(C)C)c1] | 61 |
| 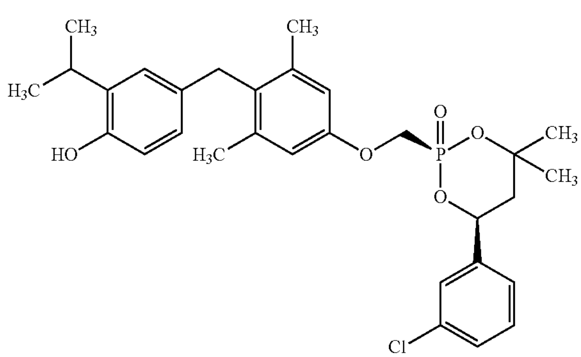 [SMILES: Cc1cc(OC[P@]2(=O)O[C@H](c3cccc(Cl)c3)CC(C)(C)O2)cc(C)c1Cc1ccc(O)c(C(C)C)c1] | 13-13-cis |

| Structure | Compound Number |
|---|---|
| 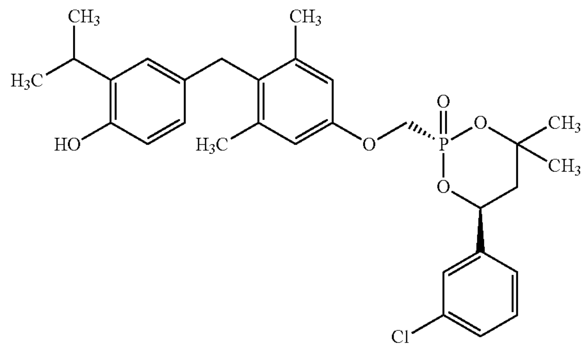 [SMILES: Cc1cc(OC[P@@]2(=O)O[C@H](c3cccc(Cl)c3)CC(C)(C)O2)cc(C)c1Cc1ccc(O)c(C(C)C)c1] | 13-13-trans |
| 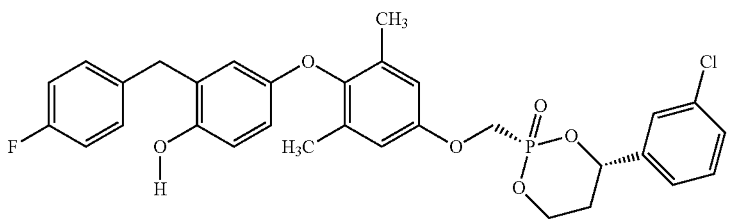 [SMILES: Cc1cc(OC[P@@]2(=O)OCC[C@@H](c3cccc(Cl)c3)O2)cc(C)c1Oc1ccc(O)c(Cc2ccc(F)cc2)c1] | 13-14-cis |
| 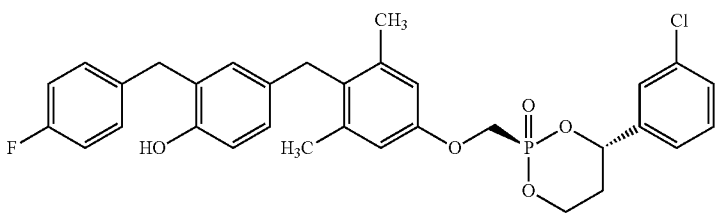 [SMILES: Cc1cc(OC[P@]2(=O)OCC[C@@H](c3cccc(Cl)c3)O2)cc(C)c1Cc1ccc(O)c(Cc2ccc(F)cc2)c1] | 13-14-trans |
| 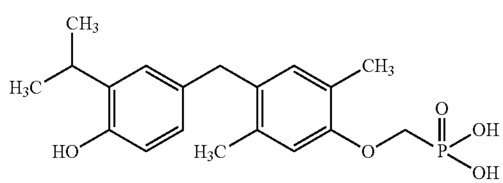 [SMILES: Cc1cc(OCP(=O)(O)O)c(C)cc1Cc1ccc(O)c(C(C)C)c1] | 7-17 |
| 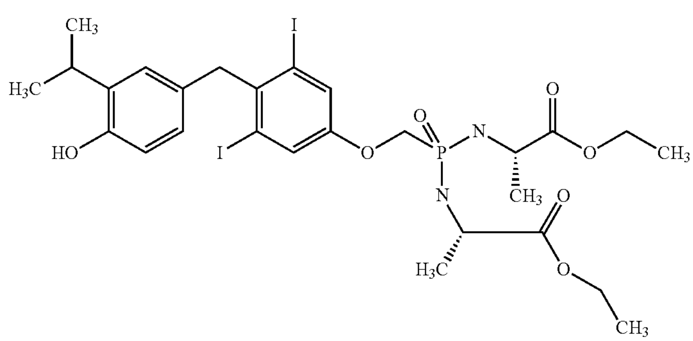 | 15-8 |
| 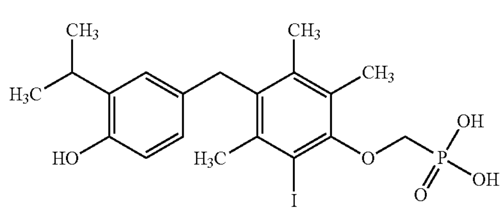 [SMILES: Cc1c(C)c(OCP(=O)(O)O)c(I)c(C)c1Cc1ccc(O)c(C(C)C)c1] | 62 |

| Structure | Compound Number |
|---|---|
| (structure) | 55 |
| (structure) | 7-15 | or pharmaceutically acceptable salts thereof.

The compounds described above may be prepared according to known methods, including those described in U.S. Pat. No. 7,829,552, which is incorporated herein by reference in its entirety. Additional TRβ agonists are described in U.S. Pat. No. 7,514,419; U.S. Application Publication No. 2009/002895; U.S. Application Publication No. 2010/0081634; U.S. Application Publication No. 2012/0046364; and PCT Application Publication No. WO 2011/038207, all of which are incorporated herein by reference in their entirety.

Pharmaceutical Compositions

The compounds useful as described above can be formulated into pharmaceutical compositions for use in treatment of the conditions described herein. Standard pharmaceutical formulation techniques are used, such as those disclosed in Remington's The Science and Practice of Pharmacy, 21st Ed., Lippincott Williams & Wilkins (2005), incorporated herein by reference in its entirety. Accordingly, some embodiments include pharmaceutical compositions comprising: (a) a safe and therapeutically effective amount of a compound described herein, or pharmaceutically acceptable salts thereof; and (b) a pharmaceutically acceptable carrier, diluent, excipient or combination thereof.

The term "pharmaceutically acceptable carrier" or "pharmaceutically acceptable excipient" includes any and all solvents, diluents, emulsifiers, binders, buffers, dispersion media, coatings, antibacterial and antifungal agents, isotonic and absorption delaying agents and the like, or any other such compound as is known by those of skill in the art to be useful in preparing pharmaceutical formulations. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions. In addition, various adjuvants such as are commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the TWEENS; wetting agents, such as sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is determined by the way the compound is to be administered.

The compositions described herein are preferably provided in unit dosage form. As used herein, a "unit dosage form" is a composition containing an amount of a compound that is suitable for administration to a subject, in a single dose, according to good medical practice. The preparation of a single or unit dosage form however, does not imply that the dosage form is administered once per day or once per course of therapy. A unit dosage form may comprise a single daily dose or a fractional sub-dose wherein several unit dosage forms are to be administered over the course of a day in order to complete a daily dose. According to the present disclosure, a unit dosage form may be given more or less often that once daily, and may be administered more than once during a course of therapy. Such dosage forms may be administered in any manner consistent with their formulation, including orally, parenterally, and may be administered as an infusion over a period of time (e.g., from about 30 minutes to about 2-6 hours). While single administrations are specifically contemplated, the compositions administered according to the methods described herein may also be administered as a continuous infusion or via an implantable infusion pump.

The methods as described herein may utilize any of a variety of suitable forms for a variety of routes for administration, for example, for oral, nasal, rectal, topical (including transdermal), ocular, intracerebral, intracranial, intrathecal, intra-arterial, intravenous, intramuscular, or other parental routes of administration. The skilled artisan will appreciate that oral and nasal compositions include compositions that are administered by inhalation, and made using available methodologies. Depending upon the particular route of administration desired, a variety of pharmaceutically-acceptable carriers well-known in the art may be used. Pharmaceutically-acceptable carriers include, for example, solid or liquid fillers, diluents, hydrotropes, surface-active agents, and encapsulating substances. Optional pharmaceutically-active materials may be included, which do not substantially interfere with the activity of the compound. The amount of carrier employed in conjunction with the compound is sufficient to provide a practical quantity of material for administration per unit dose of the compound. Techniques and compositions for making dosage forms useful in the methods described herein are described in the following references, all incorporated by reference herein: Modern Pharmaceutics, 4th Ed., Chapters 9 and 10 (Banker & Rhodes, editors, 2002); Lieberman et al., Pharmaceutical Dosage Forms: Tablets (1989); and Ansel, Introduction to Pharmaceutical Dosage Forms 8th Edition (2004).

Various oral dosage forms can be used, including such solid forms as tablets, capsules, granules and bulk powders. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carriers suitable for the preparation of unit dosage forms for peroral administration is well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid, microcrystalline cellulose, carboxymethyl cellulose, and talc. Tablets may also comprise solubilizers or emulsifiers, such as poloxamers, cremophor/Kolliphor®/Lutrol®, methylcellulose, hydroxypropylmethylcellulose, or others as are known in the art. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which can be readily made by a person skilled in the art.

Peroral (PO) compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Compositions described herein may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

A liquid composition, which is formulated for topical ophthalmic use, is formulated such that it can be administered topically to the eye. The comfort may be maximized as much as possible, although sometimes formulation considerations (e.g. drug stability) may necessitate less than optimal comfort. In the case that comfort cannot be maximized, the liquid may be formulated such that the liquid is tolerable to the patient for topical ophthalmic use. Additionally, an ophthalmically acceptable liquid may either be packaged for single use, or contain a preservative to prevent contamination over multiple uses.

For ophthalmic application, solutions or medicaments are often prepared using a physiological saline solution as a major vehicle. Ophthalmic solutions may preferably be maintained at a comfortable pH with an appropriate buffer system. The formulations may also contain conventional, pharmaceutically acceptable preservatives, stabilizers and surfactants.

Preservatives that may be used in the pharmaceutical compositions disclosed herein include, but are not limited to, benzalkonium chloride, PHMB, chlorobutanol, thimerosal, phenylmercuric, acetate and phenylmercuric nitrate. A useful surfactant is, for example, Tween 80. Likewise, various useful vehicles may be used in the ophthalmic preparations disclosed herein. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. For many compositions, the pH will be between 4 and 9. Accordingly, buffers include acetate buffers, citrate buffers, phosphate buffers and borate buffers. Acids or bases may be used to adjust the pH of these formulations as needed.

Ophthalmically acceptable antioxidants include, but are not limited to, sodium metabisulfite, sodium thiosulfate, acetylcysteine, butylated hydroxyanisole and butylated hydroxytoluene.

Other excipient components, which may be included in the ophthalmic preparations, are chelating agents. A useful chelating agent is edetate disodium, although other chelating agents may also be used in place or in conjunction with it.

For topical use, including for transdermal administration, creams, ointments, gels, solutions or suspensions, etc., containing the compound disclosed herein are employed. Topical formulations may generally be comprised of a pharmaceutical carrier, co-solvent, emulsifier, penetration enhancer, preservative system, and emollient.

For intravenous administration, the compounds and compositions described herein may be dissolved or dispersed in a pharmaceutically acceptable diluent, such as a saline or dextrose solution. Suitable excipients may be included to achieve the desired pH, including but not limited to NaOH, sodium carbonate, sodium acetate, HCl, and citric acid. In various embodiments, the pH of the final composition ranges from 2 to 8, or preferably from 4 to 7. Antioxidant excipients may include sodium bisulfite, acetone sodium bisulfite, sodium formaldehyde, sulfoxylate, thiourea, and EDTA. Other non-limiting examples of suitable excipients found in the final intravenous composition may include sodium or potassium phosphates, citric acid, tartaric acid, gelatin, and carbohydrates such as dextrose, mannitol, and dextran. Further acceptable excipients are described in Powell, et al., Compendium of Excipients for Parenteral Formulations, PDA J Pharm Sci and Tech 1998, 52 238-311 and Nema et al., Excipients and Their Role in Approved Injectable Products: Current Usage and Future Directions, PDA J Pharm Sci and Tech 2011, 65 287-332, both of which are incorporated herein by reference in their entirety. Antimicrobial agents may also be included to achieve a bacteriostatic or fungistatic solution, including but not limited to phenylmercuric nitrate, thimerosal, benzethonium chloride, benzalkonium chloride, phenol, cresol, and chlorobutanol.

The compositions for intravenous administration may be provided to caregivers in the form of one more solids that are reconstituted with a suitable diluent such as sterile water, saline or dextrose in water shortly prior to administration. In other embodiments, the compositions are provided in solution ready to administer parenterally. In still other embodiments, the compositions are provided in a solution that is further diluted prior to administration. In embodiments that include administering a combination of a compound described herein and another agent, the combination may be provided to caregivers as a mixture, or the caregivers may mix the two agents prior to administration, or the two agents may be administered separately.

The actual unit dose of the active compounds described herein depends on the specific compound, and on the condition to be treated. In some embodiments, the dose may be from about 0.01 mg/kg to about 120 mg/kg or more of body weight, from about 0.05 mg/kg or less to about 70 mg/kg, from about 0.1 mg/kg to about 50 mg/kg of body weight, from about 1.0 mg/kg to about 10 mg/kg of body weight, from about 5.0 mg/kg to about 10 mg/kg of body weight, or from about 10.0 mg/kg to about 20.0 mg/kg of body weight. In some embodiments, the dose may be less than 100 mg/kg, 90 mg/kg, 80 mg/kg, 70 mg/kg, 60 mg/kg, 50 mg/kg, 40 mg/kg, 30 mg/kg, 25 mg/kg, 20 mg/kg, 10 mg/kg, 7.5 mg/kg, 6 mg/kg, 5 mg/kg, 4 mg/kg, 3 mg/kg, 2.5 mg/kg, 1 mg/kg, 0.5 mg/kg, 0.1 mg/kg, 0.05 mg/kg or 0.005 mg/kg of body weight. In some embodiments, the actual unit dose is 0.05, 0.07, 0.1, 0.3, 1.0, 3.0, 5.0, 10.0 or 25.0 mg/kg of body weight. Thus, for administration to a 70 kg person, the dosage range would be from about 0.1 mg to 70 mg, from about 1 mg to about 50 mg, from about 0.5 mg to about 10 mg, from about 1 mg to about 10 mg, from about 2.5 mg to about 30 mg, from about 35 mg or less to about 700 mg or more, from about 7 mg to about 600 mg, from about 10 mg to about 500 mg, or from about 20 mg to about 300 mg, or from about 200 mg to about 2000 mg. In some embodiments, the actual unit dose is 5 mg. In some embodiments the actual unit dose is 10 mg. In some embodiments, the actual unit dose is 25 mg. In some embodiments, the actual unit dose is 250 mg or less. In some embodiments, the actual unit dose is 100 mg or less. In some embodiments, the actual unit dose is 70 mg or less.

Methods of Administration

The compositions described above may be administered through any suitable route of administration, for example, by injection, such as subcutaneously, intramuscularly, intraperitoneally, intravenously, or intraarterially; topically, such as by cream, lotion, or patch; orally, such as by a pill, dissolved liquid, oral suspension, buccal film, or mouthrinse; nasally, such as by a nasal aerosol, powder, or spray; or ocularly, such as by an eye drop). In some embodiments, the composition may be administered one, twice, three times, our four times per day. In other embodiments, the composition may be administered once, twice, or three times per week. In other embodiments, the composition is administered every other day, every three days, or every four days. In other embodiments, the composition every other week, every three weeks, or every four weeks. In other embodiments, the composition is administered once per month or twice per month.

In some embodiments, an initial loading dose is administered which is higher than subsequent doses (maintenance doses). The dosage form or mode of administration of a maintenance dose may be different from that used for the loading dose. In any of the embodiments disclosed herein, a maintenance dose may comprise administration of the unit dosage form on any dosing schedule contemplated herein, including but not limited to, monthly or multiple times per month, biweekly or multiple times each two weeks, weekly or multiple times per week, daily or multiple times per day. It is contemplated within the present disclosure that dosing holidays may be incorporated into the dosing period of the maintenance dose. Such dosing holidays may occur immediately after the administration of the loading dose or at any time during the period of administration of the maintenance dose. In some embodiments, the loading dose is 300 mg or less; 250 mg or less, 200 mg or less, 150 mg or less, or 100 mg or less. In some embodiments, the maintenance dose is 300 mg or less; 200 mg or less, 100 mg or less, 50 mg or less, 25 mg or less, 10 mg or less, 5 mg or less, or 1 mg or less.

Methods of Treatment

Some embodiments relate to a method for the treatment of a glycogen storage disease or its symptoms or sequelae, comprising administering an effective amount of a compound described herein to a subject in need thereof. The glycogen storage disease may either be hepatic or non-hepatic glycogen storage disease.

In some embodiments, the disease is selected from the group consisting of glycogen storage disease type 0, 1, 2, 3, 4, 5, 6, 7, 8, 9, 10, 11, or 12. In some embodiments, the glycogen storage disease is selected from one or more of aglycogenosis, von Gierke disease, Pompe disease, Cori disease, Forbes disease, limit dextrinosis, debranching enzyme disease, Andersen disease, glycogen phosphorylase deficiency, brancher deficiency, amylopectinosis, glycogen branching enzyme deficiency, McArdle disease, Hers disease, Tarui disease, Autosomal liver and muscle phosphorylase kinase deficiency, Autosomal liver phosphorylase kinase deficiency, X-linked liver phosphorylase kinase deficiency, GSD X, Fanconi-Bickel syndrome, or aldolase A deficiency. In some embodiments, the compounds of the present disclosure are administered so as to effect the release of stored glycogen.

In some embodiments, the compounds of the present disclosure are administered as a means of treating the hepatic symptoms of glycogen storage diseases. In some embodiments, said compound is administered to a patient showing symptoms of hyperlipidemia, hypercholesterolemia, steatosis, hepatic fibrosis, increased ALT, increased AST, increased serum triglycerides, cirrhosis, hepatomegaly, hepatocellular adenoma, or hepatocellular carcinoma. In some embodiments, the compounds of the present disclosure are administered to a patient showing insulin insensitivity or elevated blood glucose. In some embodiments, the compounds of the present disclosure are administered to a patient showing persistently elevated serum lactic acid levels. In some embodiments, the compounds of the present disclosure are administered as a means of treating non-hepatic symptoms of glycogen storage diseases. In some further embodiments, non-hepatic symptoms of glycogen storage disease may comprise hypoglycemia, disturbances in blood glucose regulation, and/or cardiomegaly.

In some embodiments the compounds of the present disclosure are coadministered with another therapeutic agent. In some further embodiments, said other therapeutic agent is an enzyme replacement therapy. In some further embodiments, said other therapeutic agent is alglucosidase alfa. In some further embodiments, said other therapeutic agent is a glucose-6-phosphatase, a debranching enzyme, a glycogen synthase, a glucose-6-phosphatase translocase, a phosphatase translocase, an alpha-1-4-glucosidase, an amylo-1-6-glucosidase, an amylo-1,4-to-1,6-transglucosidase, a glycogen phosphorylase, a phosphofructokinase, a cyclic-3',5' AMP-dependent kinase, a type 2 glucose transporter, or an aldolase A. In some further embodiments, said other therapeutic agent comprises a mixture of the above enzymes. In some further embodiments, said other therapeutic agent comprises an additional enzyme.

In some embodiments the compounds of the present disclosure are administered preceding, following, or contemporaneously with a gene therapy. In some further embodiments, said gene therapy effects the replacement or repair of the gene defect causing the patient's glycogen storage disease. In some further embodiments, said gene therapy effects the insertion of a functional gene encoding a glucose-6-phosphatase, a debranching enzyme, a glycogen synthase, a glucose-6-phosphatase translocase, a phosphatase translocase, an alpha-1-4-glucosidase, an amylo-1-6-glucosidase, an amylo-1,4-to-1,6-transglucosidase, a glycogen phosphorylase, a phosphofructokinase, a cyclic-3',5' AMP-dependent kinase, a type 2 glucose transporter, or an aldolase A. In some other embodiments, said gene therapy incorporates repair or replacement of one or more native copies of the relevant gene defect. In some embodiments such repair or replacement is effected utilizing the CRISPR, and especially the CRISPR-Cas9, CRISPR-Cas3, and/or CRISPR-Cas6 system. In some embodiments said gene therapy is carried out ex vivo. In some embodiments, said gene therapy is carried out by administration of the relevant therapeutic agent directly in to the body of the patient, using, for example, an encapsulated nucleic acid, a viral vector, or other means as are known in the art. In some other embodiments, said gene therapy is supplemented with an enzyme replacement therapy.

In some embodiments, the compounds of the present disclosure are administered preceding, following, or contemporaneously with a transplant of the heart, of the liver, of pancreatic islet cells, of one or more kidneys, or of skeletal muscle tissue. In some other embodiments, said organ transplant is supplemented with enzyme replacement therapy. In some other embodiments, said organ transplant is supplemented with a gene therapy. In some embodiments, the compounds of the present disclosure are administered preceding, following, or contemporaneously with a transplant of the heart, of the liver, of pancreatic islet cells, of one or more kidneys, or of skeletal muscle tissue, as well as a gene therapy and/or an enzyme replacement therapy.

In some embodiments, the compounds of the present disclosure are coadministered with a second therapeutic agent that modulates blood lactate levels. In some further embodiments, said second therapeutic agent may comprise a cofactor of an enzyme important to lipid or carbohydrate metabolism. In some further embodiments, said second therapeutic agent may comprise one or more of thiamine, biotin, riboflavin, or any precursors to such agents and any combination thereof.

In some embodiments, the compounds of the present disclosure are coadministered with a second therapeutic agent that modulates liver enzyme levels. In some further embodiments, said second therapeutic agent may comprise an agent to reduce or prevent liver inflammation or elevation in liver function tests.

In some embodiments, the compounds of the present disclosure are coadministered with a second therapeutic agent that modulates blood sugar. In some further embodiments, said second therapeutic agent may comprise a peptide, a sugar, a polysaccharide, an amino acid, or any combination thereof. In some further embodiments, said second therapeutic agent may comprise one or more of glucose, galactose, fructose, sucrose, maltose, lactose, arabinose, or other sugars, or any combination thereof. In some further embodiments, said second therapeutic agent may comprise one or more of corn starch, potato starch, wheat starch, vegetable starch, cassava or other starches, or any combination thereof. In some embodiments, said second therapeutic agent may comprise one or more sugars and one or more starches. In some embodiments, said second therapeutic agent may comprise one or more of asparagine, tyrosine, cysteine, serine, tyrosine, glutamine, histidine, glutamic acid, arginine, lysine, aspartic acid, tryptophan, isoleucine, methionine, proline, phenylalanine, glycine, alanine, valine, leucine, or any combination thereof. In some further embodiments, said second therapeutic agent may comprise an insulin, an insulin-like peptide, a glucagon, a glucagon-like peptide, or any combination thereof. In some further embodiments, said second therapeutic agent may comprise a combination of an insulin, an insulin-like peptide, a glucagon, and/or a glucagon-like peptide with a starch or a sugar.

In some embodiments, the compounds of the present disclosure are coadministered with a statin or PCSK9 inhibitor. Representative statins include but are not limited to atorvastatin, fluvastatin, lovastatin, pravastatin, rosuvastatin, simvastatin, and pitavastatin. Representative PCSK9 inhibitors include but are not limited to, alirocumab, bococizumab, and evolocumab.

In some embodiments, administration of the compounds of the present disclosure result in a reduction in liver size or the prevention of hepatomegaly in a subject having a glycogen storage disease. In some embodiments, liver size is assessed with regard to the absolute mass or volume of the liver. In some embodiments, liver size is assessed as the relative mass of the liver compared to the overall mass of the body of the subject. In some embodiments, liver size is assessed by sonography, radiography including computed tomography, magnetic resonance imaging or by manual palpitation and/or percussion and estimation using such methods and measurements as are known in the art. In some embodiments, administration of the compounds of the present disclosure result in a reduction in body mass in a subject having a glycogen storage disease. In some embodiments, administration of the compounds of the present disclosure result in a reduction in total liver triglycerides in a subject having a glycogen storage disease. In some embodiments, administration of the compounds of the present disclosure result in a reduction in liver triglyceride concentration in a subject having a glycogen storage disease. In some embodiments, administration of the compounds of the present disclosure result in reduced serum cholesterol in a subject having a glycogen storage disease. In some embodiments, administration of the compounds of the present disclosure result in reduced blood glucose in a subject having a glycogen storage disease. In some embodiments, administration of the compounds of the present disclosure result in little or no change in liver glycogen levels in a subject having a glycogen storage disease. In some embodiments, administration of the compounds of the present disclosure result in reduced liver glycogen levels in a subject having a glycogen storage disease. In some embodiments, administration of the compounds of the present disclosure result in little or no change in muscle glycogen levels in a subject having a glycogen storage disease. In some embodiments, administration of the compounds of the present disclosure result in a reduction in serum cholesterol of more than 5%, more than 10%, more than 15%, more than 20%, more than 25%, more than 30%, more than 35%, more than 40%, more than 45%, more than 50%, more than 55%, or more than 60% in a subject having a glycogen storage disease. In some embodiments, administration of the compounds of the present disclosure result in a reduction in serum cholesterol of 5% or less, 10% or less, 15% or less, 20% or less, 25% or less, 30% or less, 35% or less, 40% or less, 45% or less, 50% or less, 55%, or 60% or less in a subject having a glycogen storage disease. In some embodiments, administration of the compounds of the present disclosure result in a reduction in blood glucose of more than 5%, more than 10%, more than 15%, more than 20%, more than 25%, more than 30%, more than 35%, more than 40%, more than 45%, more than 50%, more than 55%, or more than 60% in a subject having a glycogen storage disease. In some embodiments, administration of the compounds of the present disclosure result in a reduction in blood glucose of 5% or less, 10% or less, 15% or less, 20% or less, 25% or less, 30% or less, 35% or less, 40% or less, 45% or less, 50% or less, 55%, or 60% or less in a subject having a glycogen storage disease. In some embodiments, administration of the compounds of the present disclosure result in no change in kidney mass in a subject having a glycogen storage disease.

The methods described herein are further illustrated by the following examples.

EXAMPLE 1

Compound 2 Dosing Study in Dogs: The objective of the study was to determine the effects of oral administration of Compound 2 once-daily for 14 days followed by alternate day dosing for 14 days on plasma cholesterol levels and indicators of thyroid function in beagle dogs. Compound 2 was formulated with Lutrol F68 NF (Poloxomer 188) and carboxymethylcellulose (CMC; sodium salt/high viscosity) and was administered as a suspension in 0.5% CMC/1% Lutrol in deionized water. Twelve beagle dogs (9-15 kg) were randomized into 6 dosing groups (1 male and 1 female/group) and gavaged once-daily with a 0.5% CMC/1% Lutrol F68 suspension of Compound 2 at doses of 0.1, 0.3, 1, 3, or 10 mg/day or with vehicle for 14 days. At the end of the treatment cycle (Cycle 1), the dogs were washed out for 4 weeks and then entered into a second 14-day treatment cycle. Cycle 2 employed the same dosing paradigm as Cycle 1, but animals were randomized to Cycle 2 in such a way that the combined dosing groups from the two cycles consisted of 4 different animals (2 males, 2 females) each. At the conclusion of Cycle 2, dosing was continued on alternate days for an additional 14-day period (Cycle 2 Extension). Blood samples were collected at baseline and appropriate time intervals thereafter and analyzed for total plasma cholesterol levels, serum levels of total T4 (tT4), free T4 (fT4), total T3 (tT3), free T3 (fT3), and thyroid stimulating hormone (TSH).

Figure 2:
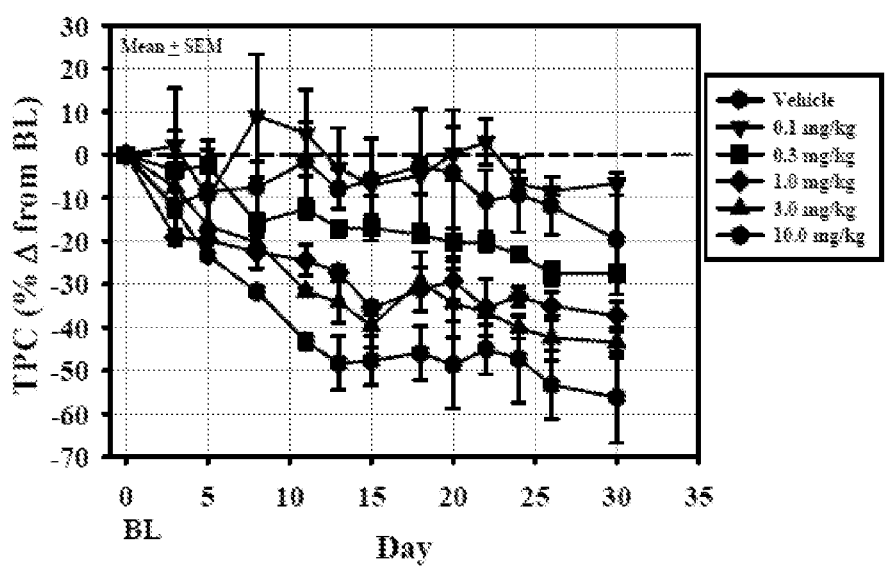
FIG. 2 shows the effect of once-daily oral administration of Compound 2 for 14 days followed by alternate day administration of Compound 2 for 14 days on total plasma cholesterol (TPC) levels in beagle dogs (n=4 per group).

Treatment with Compound 2 for 14 days resulted in progressive, dose-dependent reductions of total plasma cholesterol levels, with an average reduction on Day 15 of ~28 mg/dL or ~22% from baseline at a dose of 0.3 mg/kg/day and of ~71 mg/dL or ~47% from baseline at the highest dose evaluated (10 mg/kg/day) (See FIG. 1). The lowest dose of Compound 2 evaluated, 0.1 mg/kg/day, had minimal effects on total plasma cholesterol levels (FIG. 1). During the alternate day dosing period of Cycle 2 (Cycle 2 Extension), total plasma cholesterol levels in the Compound 2 treatment groups remained reduced relative to vehicle-treated animals to a similar or greater extent than observed after once-daily dosing (See FIG. 2).

EXAMPLE 2

The objective of this study was to evaluate the efficacy and safety of Compound 2 treatment at doses of 3, 10, and 30 mg/kg/day for 9 weeks in male ob/ob mice. 3,3',5-Triiodo-L-thyronine (T3) was used as a comparator in this study.

Methods: Seventy-eight adult male ob/ob mice were assigned to six different treatment groups (n=6-24/group). Animals were dosed daily with either vehicle [1% carboxymethylcellulose (CMC) in water, PO], T3 [(100 nmole/kg/day in aqueous solution, subcutaneous (SC)], or Compound 2 [3, 10 or 30 mg/kg/day in 1% CMC, PO]. Blood glucose and plasma cholesterol were measured weekly in all animals. Subsets of animals in the vehicle-treated and 30 mg/kg/day Compound 2-treated groups were sacrificed after 3, 6 and 9 weeks of treatment to analyze the temporal effects of Compound 2 on liver weight and liver triglyceride levels. Liver triglyceride levels, liver glycogen content, heart, liver and epididymal fat pad weights, and plasma clinical chemistry parameters were measured at sacrifice.

Figure 3:
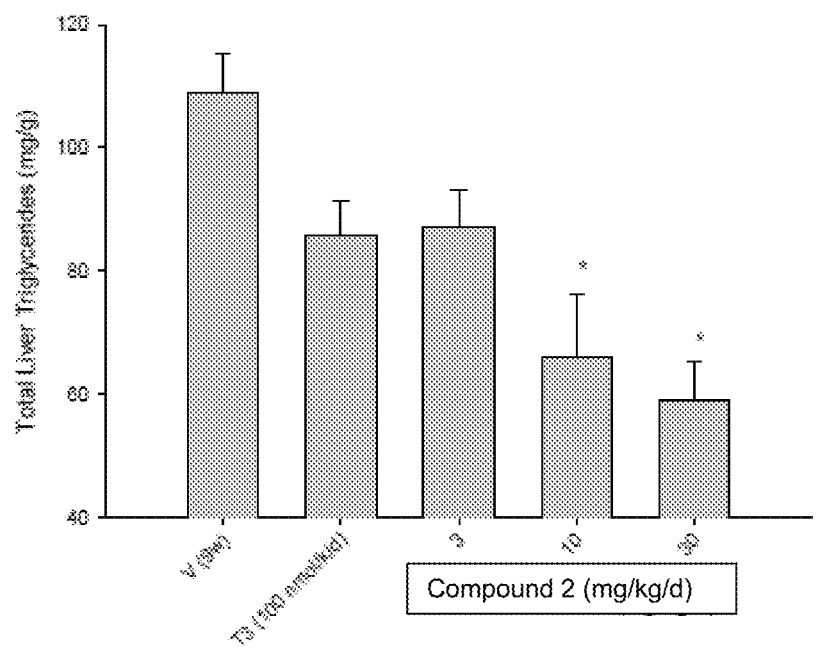
FIG. 3 shows the effects of Compound 2 and T3 on liver triglyceride content following 9 weeks of treatment. At the end of 9 weeks of treatment, the animals were sacrificed and liver triglyceride content analyzed. The liver triglyceride content of the animals from the 10 and 30 mg/kg/day Compound 2-treated group was significantly ($p<0.05$) lower than the vehicle-treated group (*).
Figure 4:
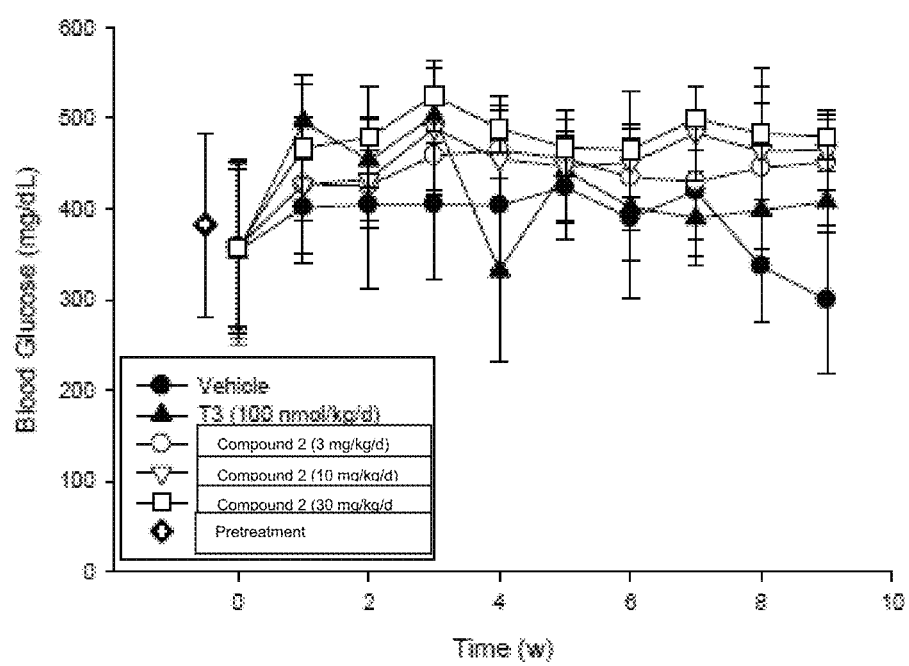
FIG. 4 shows the effects of Compound 2 and T3 on blood glucose in male ob/ob mice. Blood glucose was measured weekly from a tail nick using a OneTouch glucose meter.
Figure 5:
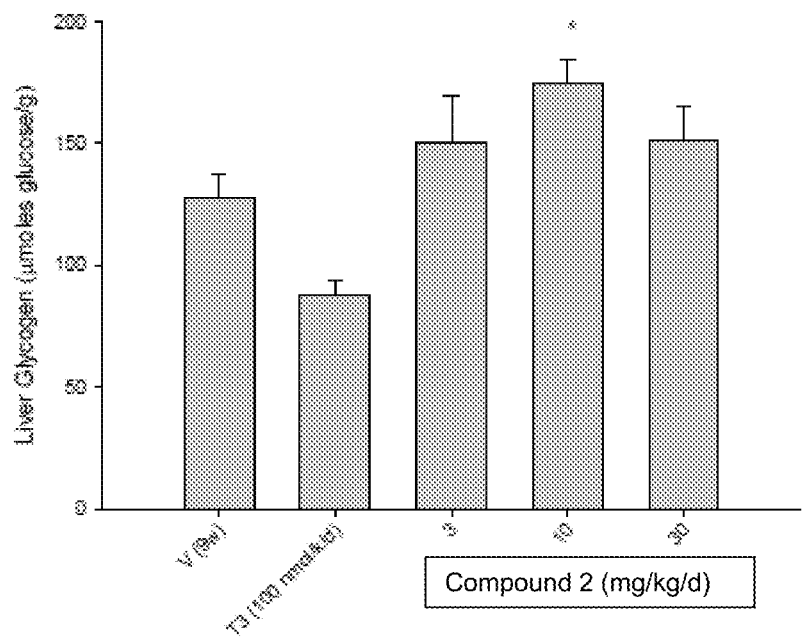
FIG. 5 shows the effects of Compound 2 and T3 on liver glycogen content following 9 weeks of treatment. At the end of 9 weeks of treatment, the animals were sacrificed and liver glycogen content measured. The liver glycogen content of the animals from the 10 mg/kg/day Compound 2-treated group was significantly ($p<0.05$) higher than the vehicle-treated group (*).
Figure 6:
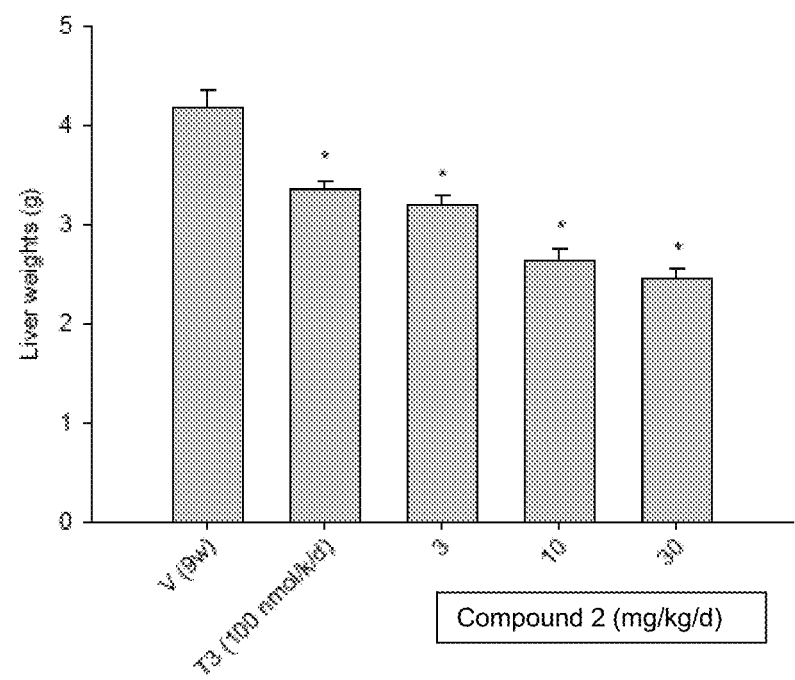
FIG. 6 shows the effects of Compound 2 and T3 on liver weight following 9 weeks of treatment. At the end of 9 weeks of treatment, the animals were sacrificed and liver weight measured. The liver weight of the animals from all treatment groups was significantly ($p<0.05$) lower than vehicle-treated group (*).

Results: Plasma cholesterol, body weight, liver weight, and liver triglyceride content increased progressively in vehicle-treated mice over the 9-week treatment period. Multiple differences in metabolic and physiological parameters were observed in drugtreated animals relative to vehicle-treated animals throughout the study. After 9 weeks of treatment, total plasma cholesterol levels were ~43%, ~42%, and ~47% lower in the 3, 10, and 30 mg/kg/day Compound 2-treated groups, respectively. Liver triglyceride levels were lower in the group treated with Compound 2 at 30 mg/kg/day from Week 3 onwards. At 9 weeks, liver triglyceride levels were ~39% and ~46% lower in the groups treated with 10 and 30 mg/kg/day of Compound 2, respectively (FIG. 3). Blood glucose levels were increased in the 30 mg/kg/day Compound 2 group at 3 weeks and in all Compound 2-treated groups at 9 weeks (FIG. 4). Terminal liver glycogen levels in the Compound 2-treated groups were modestly higher or similar to those in the vehicle-treated group (FIG. 5). All dose groups of Compound 2 had lower terminal liver weights (FIG. 6). Compound 2-treatment (10 and 30 mg/kg/day) resulted in lower total plasma protein and albumin levels. Increased total plasma bilirubin levels were observed at 10 and 30 mg/kg/day Compound 2, but these changes were not dose-related. Decreased alanine aminotransferase (ALT) levels were observed in all dose groups of Compound 2.

Total plasma cholesterol was ~66% lower in T3-treated mice at 9 weeks. Terminal liver triglyceride and liver glycogen levels were similar in the T3- and vehicle-treated groups. Blood glucose levels in the T3-treated group were similar to those in the vehicle-treated group at all time points evaluated. T3 treatment resulted in lower liver weight. T3-treatment also decreased total plasma protein, albumin, ALT, and calcium levels and increased plasma triglyceride levels (~56%).

Conclusions: Compound 2 treatment for 9 weeks largely prevented the increase in plasma cholesterol levels, liver weight, and liver triglyceride content observed in vehicle-treated mice. Blood glucose levels were increased relative to the vehicle-treated group after 3 and 9 weeks of Compound 2 treatment. Statistically significant changes in several plasma clinical chemistry parameters were observed following Compound 2 treatment: increased bilirubin and decreased total protein, and albumin. In addition, Compound 2 treatment reduced the elevated ALT levels characteristic of ob/ob mice. As seen with Compound 2, T3 treatment prevented the increase in plasma cholesterol levels and liver weight observed in vehicle-treated mice. T3 treatment did not increase blood glucose levels or decrease liver triglyceride content. Another important difference between T3 and Compound 2 was the increase in plasma triglyceride levels observed with the former but not the latter drug treatment.

EXAMPLE 3

Objectives: The objective of the study was to evaluate the efficacy and safety of Compound 2 treatment for 4 weeks in male Zucker Diabetic fatty (ZDF) rats. Total plasma cholesterol, blood glucose levels, liver and muscle glycogen levels, and a plasma clinical chemistry were evaluated. Additionally, histological and biochemical assessments of hepatic steatosis were performed post-mortem. MB07875, a known human thyroid hormone receptor ligand, was included as a comparator in these studies.

Methods: Eight-week old male ZDF rats (n=5/group) were treated orally with Compound 2 or MB07875 for 28 days. The doses of Compound 2 [in 0.5% carboxymethylcellulose (CMC)] were 0.25, 0.5, 1, 2.5, 5, 15 and 50 mg/kg/day. The dose of MB07875 (in 0.5% CMC) was 0.2 mg/kg/day. Body weight was assessed just prior to treatment and at 24 hours following the last dose. Total plasma cholesterol and blood glucose were measured on a weekly basis. While still under anesthesia, blood was collected from the inferior vena cava for analysis of clinical chemistry and insulin and free fatty acid levels, and the gastocnemius muscle was removed and freeze-clamped for analysis of glycogen content. In addition, the liver was removed and weighed, and a portion freeze-clamped for glycogen and triglyceride analysis. Another portion was placed in 10% neutral buffered formalin for hematoxalin and eosin (H & E) staining. Finally, the heart was excised and weighed.

Figure 7:
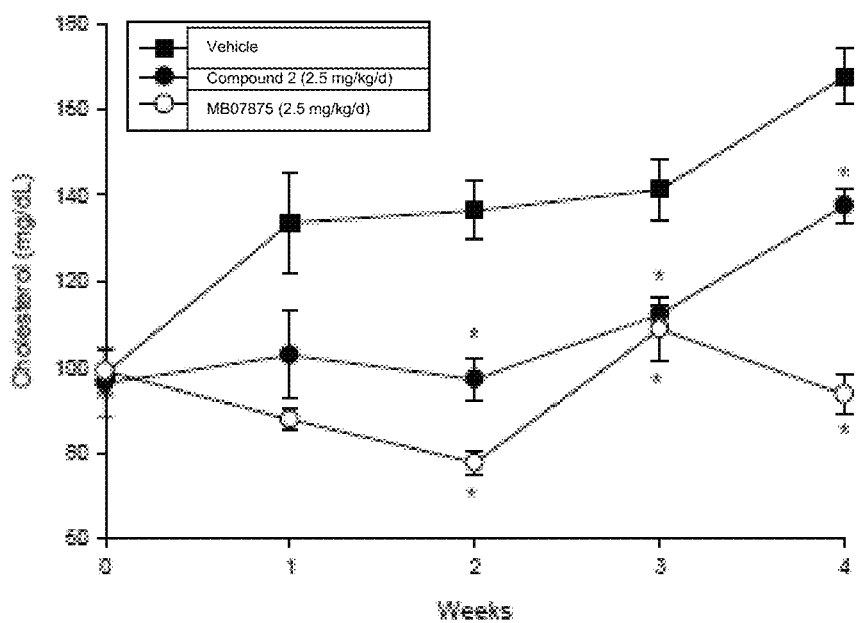
FIG. 7 shows the temporal profile of the effects of vehicle, Compound 2 (2.5 mg/kg/day) and MB07875 (0.2 mg/kg/day) on total plasma cholesterol levels throughout the 28-day treatment period. Horizontal lines represent the vehicle-treated group with the solid line representing the mean and the upper and lower dotted lines representing the upper and lower limits of the SEM. Significant differences versus the vehicle-treated group are shown (*).
Figure 8A:
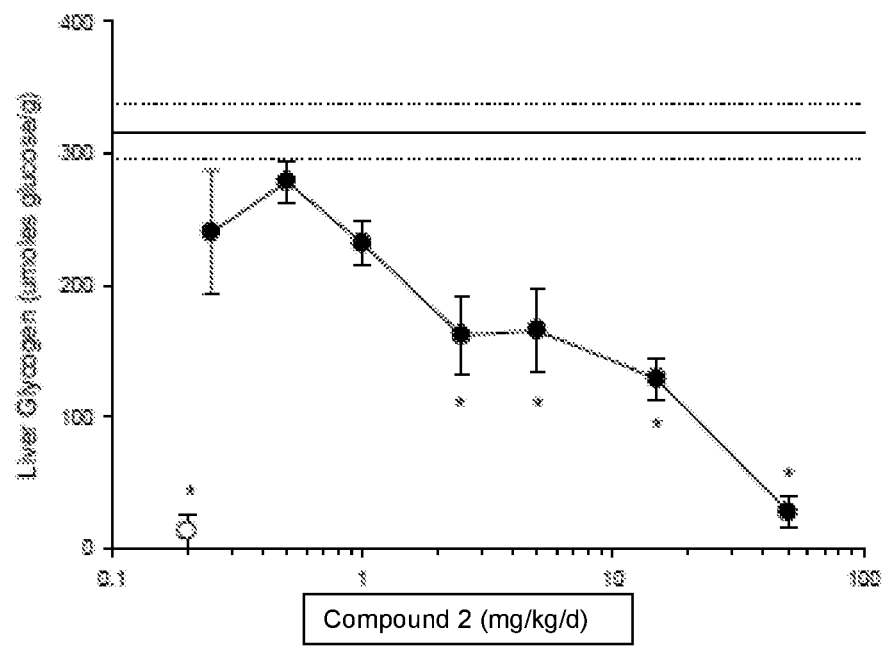
FIG. 8 shows Liver (A) and Muscle (B) glycogen content in male Zucker Diabetic fatty (ZDF) rats following 28 days of treatment with either Compound 2 (•) or MB07875 (○) at the indicated dose. Horizontal lines represent the vehicle-treated group with the solid line representing the mean and the upper and lower dotted lines representing the upper and lower limits of the SEM. Significant differences versus the vehicle-treated group are shown (*).
Figure 9:
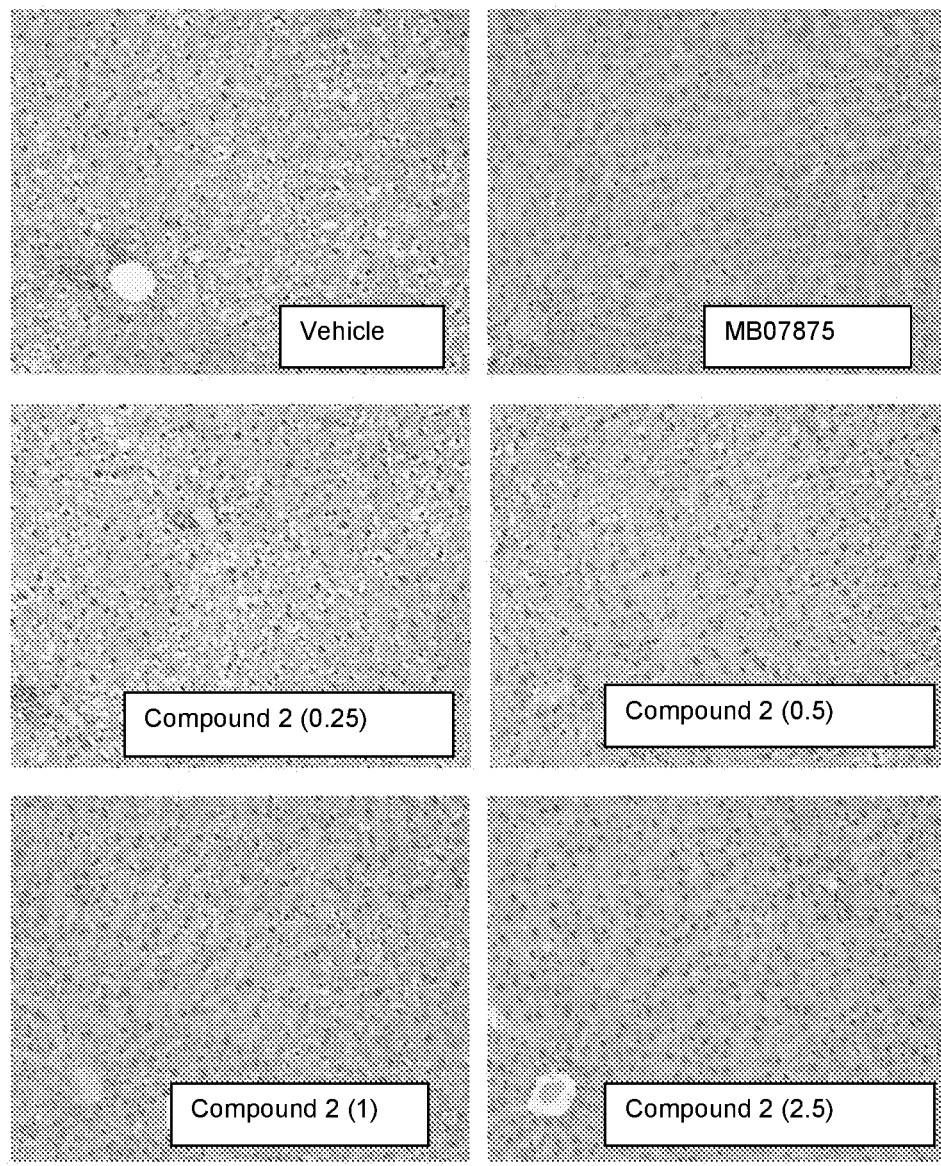
FIG. 9 shows representative hematoxylin and eosin stained liver sections from male ZDF rats following 28 days of treatment with either Compound 2 (at the indicated dose in mg/kg/day) or 0.2 mg/kg/day MB07875.

Results: All metabolic changes in drug-treated animals are described relative to vehicle-treated animals at the corresponding time points. Compound 2, at doses of 1 mg/kg/day and above, lowered total plasma cholesterol, with reductions of ~25% and ~34% at the first statistically significant dose (1 mg/kg/day) and the highest dose (50 mg/kg/day), respectively, on day 28 (FIG. 7). Blood glucose levels were not increased in the Compound 2-treated groups at any time during the study, and were significantly decreased (~47%) in the 2.5 mg/kg/day dose group on day 28. Compound 2 treatment had no significant effect on heart or body weight. Liver glycogen levels were reduced in a dose-dependent manner by Compound 2 (>90% at 50 mg/kg/day), while muscle glycogen levels were unaffected by treatment (FIG. 8A, B). Plasma insulin levels tended to be higher at doses of 1 mg/kg/day of Compound 2 and above. Free fatty acid levels were unaffected by Compound 2 treatment. Several statistically significant differences in plasma clinical chemistry parameters were observed in the Compound 2-treated groups on day 28. Blood urea nitrogen was decreased by ~21% and ~26% at doses of 15 and 50 mg/kg/day of 3 of 27 Compound 2, respectively. Total bilirubin was increased by ~86% and ~79% at doses of Compound 2 of 2.5 and 50 mg/kg/day, respectively. Alkaline phosphatase was decreased in a dose-related manner at doses of Compound 2 of 1 mg/kg/day and above, with a ~42% decrease evident at the highest dose (50 mg/kg/day). Calcium levels were decreased by ~5% and phosphorus levels increased by ~27% at 50 mg/kg/day of Compound 2. Globulin was decreased by up to ~25% at doses of Compound 2 of 5 mg/kg/day and above. The albumin-to-globulin ratio was increased by 21% and 32% at doses of Compound 2 of 15 and 50 mg/kg/day, respectively. Total protein levels were decreased by ~10% at 50 mg/kg/day of Compound 2. Although histological analysis of liver sections revealed a decrease in microvesicular steatosis in Compound 2-treated rats at doses ≥2.5 mg/kg/day (FIG. 9), there was no statistically significant decrease in liver triglyceride content.

Figure 8B:
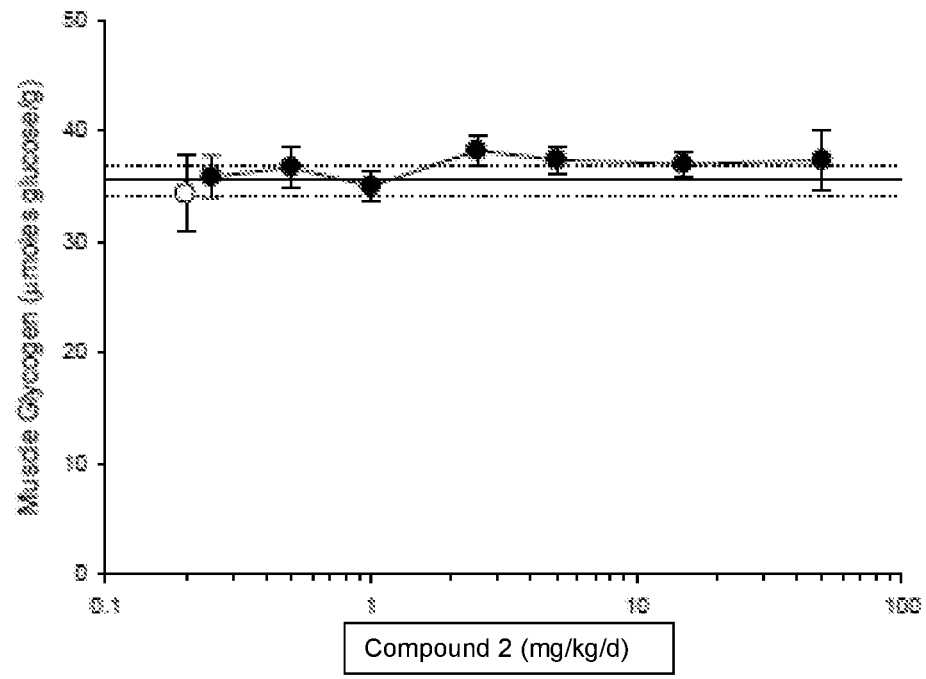

Total plasma cholesterol and blood glucose were ~43% and ~66% lower, respectively, in the MB07875-treated group on day 28, while plasma insulin levels were significantly increased (~5-fold). Heart weights, body weights, and the heart-to-body weight ratios were similar between the MB07875- and vehicle-treated groups. After 28 days of dosing, MB077811 treatment resulted in marked, dose-dependent decreases in liver glycogen levels (FIG. 8A) relative to vehicle treatment, with a ~90% decrease observed at the highest dose evaluated (50 mg/kd/day). Liver glycogen content was decreased by ~96% in the MB07875-treated group relative to the vehicle-treated group. There were no significant differences in muscle glycogen content between the vehicle-, Compound 2-, and MB07875-treated groups (FIG. 8B). Clinical chemistry analysis of plasma samples from the MB07875-treated group revealed increased chloride (~6%), decreased blood urea nitrogen (~8%), decreased alkaline phosphatase (~53%), decreased calcium (~8%), decreased globulin (~18%), and an increased albumin/globulin ratio (~26%). MB07875 treatment reduced microvesicular hepatic steatosis but did not alter liver triglyceride content.

Conclusions: Treatment of male ZDF rats with Compound 2 at doses from 1 to 50 mg/kg/day for 28 days decreased total plasma cholesterol levels by up to 34%. In addition, hepatic microvesicular steatosis was reduced at doses of Compound 2 of 2.5 mg/kg/day and above. Compound 2 treatment (up to 50 mg/kg/day) did not alter cardiovascular function as assessed by monitoring heart rate, systolic and diastolic aortic pressure, and LV dP/dt. Blood glucose levels in the Compound 2-treated groups were similar or lower than those in the vehicle group. MB07875 treatment (0.2 mg/kg/day) also was associated with reduced total plasma cholesterol, reduced blood glucose, and an improvement in microvesicular hepatic steatosis. Markedly reduced hepatic glycogen stores and changes in several plasma clinical chemistry parameters were observed in both the Compound 2- and MB07875-treated groups. In summary, oral administration of Compound 2 to male ZDF rats for 28 days decreased total plasma cholesterol levels and reduced hepatic microvesicular steatosis without causing cardiovascular side effects or exacerbation of hyperglycemia.

EXAMPLE 4

Objectives: The objectives of this study were to evaluate the effects of 2, 5 and 10 weeks of Compound 2 treatment at doses of 10 and 30 mg/kg/day on total plasma cholesterol levels, blood glucose levels, and hepatic steatosis in a mouse model of diet-induced obesity.

Methods: Male C57Bl/6 mice (4 weeks old) were fed a high-fat diet (60% fat by kcal) for 88 days to induce obesity, hyperlipidemia, and mild hyperglycemia prior to initiation of the study. For the study, 3 groups of mice (n=24-28) were dosed daily by gavage with 10 or 30 mg/kg of Compound 2 or vehicle (0.1% carboxymethylcellulose) and maintained on the same high-fat diet. During treatment, body weight, total plasma cholesterol levels, and blood glucose levels of the animals were measured weekly. Subsets of animals (n=6-12; 30 mg/kg/day) were sacrificed prior to treatment and after 2, 5 and 10 weeks of treatment for analysis of liver weights, liver triglyceride levels and liver histology.

Figure 10:
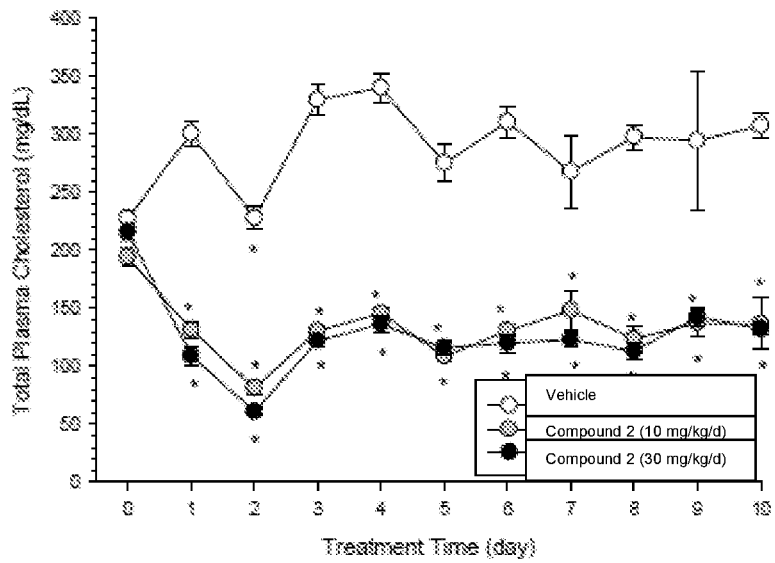
FIG. 10 shows the effects of Compound 2 on total plasma cholesterol level in male Diet-Induced Obesity (DIO) mice. A two-way ANOVA with repeated measures on the time factor demonstrated that the effect of treatment ($p<0.0001$) and the interaction between treatment and time ($p=0.0004$) were significant. Post-hoc analyses of total plasma cholesterol revealed significant differences in cholesterol between each of the Compound 2-treated groups compared with the vehicle treated group at all time points measured (*).
Figure 11:
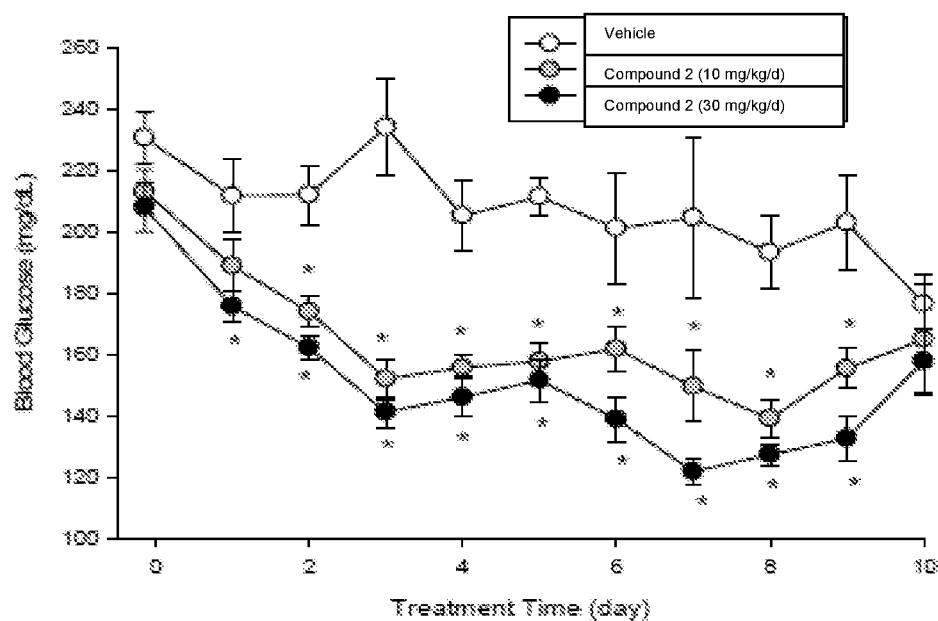
FIG. 11 shows the effects of Compound 2 on blood glucose levels in male DIO mice. A two-way ANOVA with repeated measures on the time factor demonstrated that the effect of treatment was significant ($p<0.0001$) but the interaction between treatment and time was not significant ($p=0.0735$). Post-hoc analyses of blood glucose levels revealed significant differences between the Compound 2-treated groups and vehicle-treated groups at the indicated time points (*).
Figure 12A:
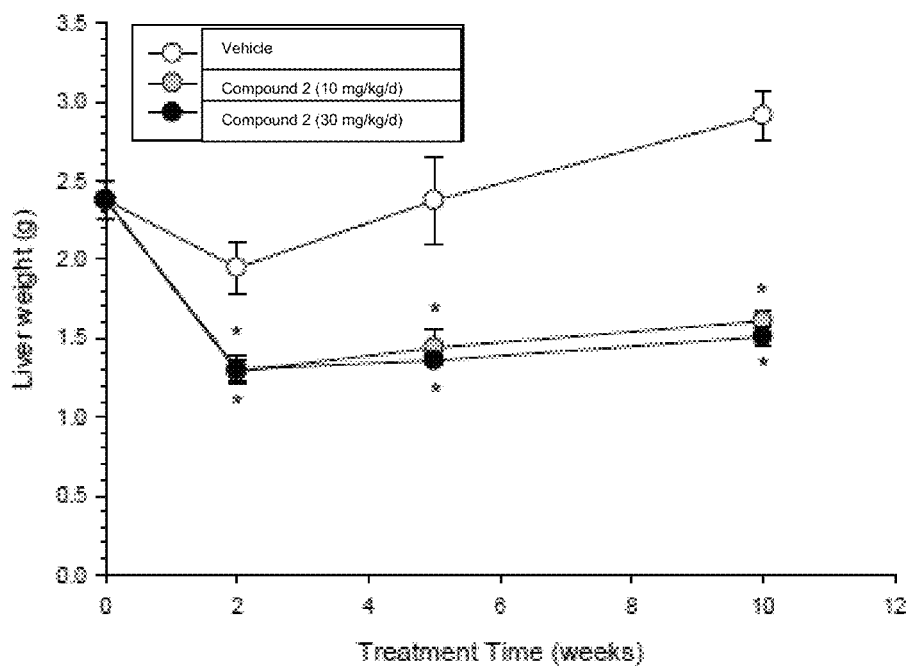
FIG. 12 shows the effects of Compound 2 on liver weight (A) and liver-to-body weight ratio (B) in male DIO mice. A two-way ANOVA demonstrated that the effect of treatment for each parameter was significant ($p<0.0001$ and $p<0.0001$, respectively). Post hoc analyses of the two parameters revealed significant differences between each of the Compound 2-treated groups compared with the vehicle-treated group at the indicated time points (*).
Figure 12B:
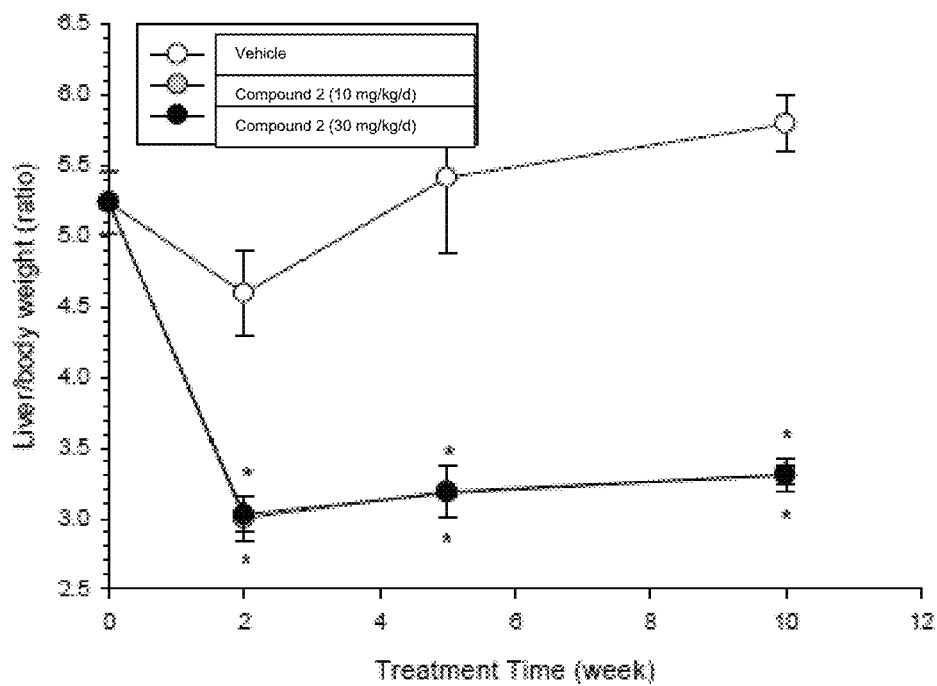
Figure 13:
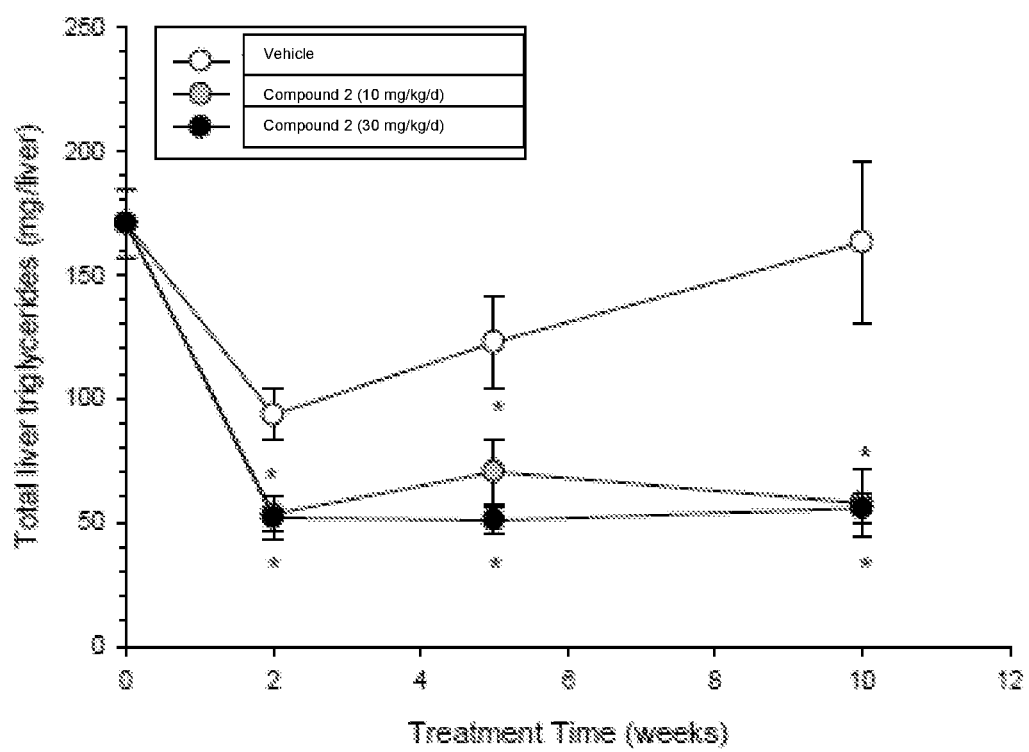
FIG. 13 shows the effects of Compound 2 on total liver triglyceride mass in male DIO mice. Analyses using a two-way ANOVA demonstrated that the effect of treatment for total liver triglycerides were significant ($p<0001$). Post hoc analyses of the total liver triglycerides revealed significant differences between each of the Compound 2-treated groups compared with the vehicle-treated group at the indicated time points for total triglyceride content (*).
Figure 14:
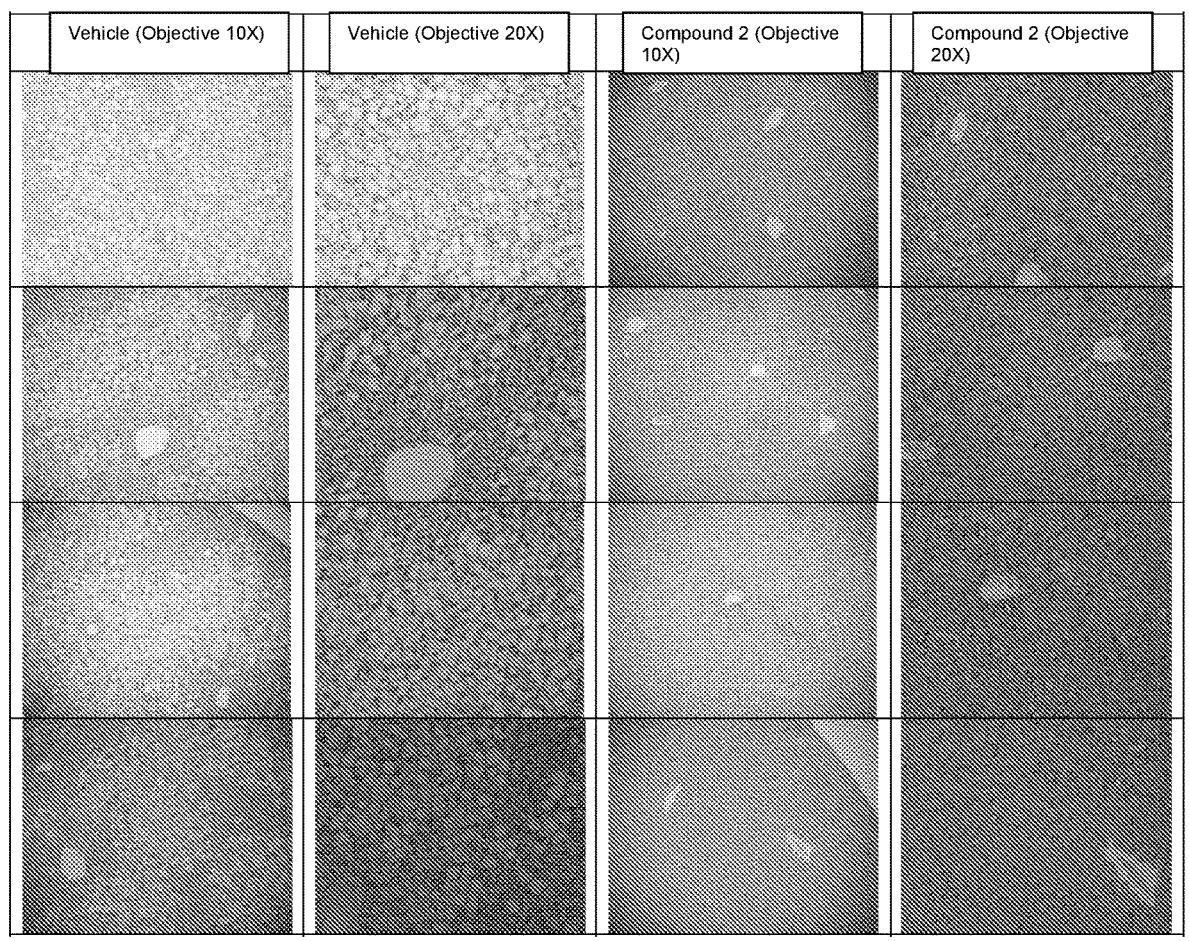
FIG. 14 shows photomicrographs of hematoxylin- and eosin-stained liver sections of vehicle-treated and 30 mg/kg/day Compound 2-treated DIO mice. Representative microphotographs from 4 animals in each of these two groups are shown below.

Results: Total plasma cholesterol levels were decreased by more than 50% in the 10 and 30 mg/kg/day Compound 2-treated groups from week 1 through the end of the study compared to the vehicle-treated group (FIG. 10). Blood glucose levels were also significantly lower (by up to 25%) in the Compound 2-treated groups compared with the vehicle-treated group at most time points examined (FIG. 11). Liver weights and liver-to-body weight ratios were ~50% and ~40% lower, respectively, for the 10 and 30 mg/kg/day Compound 2-treated groups compared with the vehicle treated group following 2, 5 and 10 weeks of treatment (FIG. 12). No significant changes in liver triglyceride concentrations (mg/g liver) were detected at any time point when either Compound 2-treated group was compared with the vehicle-treated group. However, total liver triglyceride content (mg/liver) was significantly lower (up to 60%) in the 10 and 30 mg/kg/day Compound 2-treated groups compared with the vehicle-treated group at weeks 2, 5, and 10 (FIG. 13). Macrovesicular and microvesicular steatosis were visually reduced in the 30 mg/kg/day Compound 2-treated animals compared with vehicle-treated animals after 2, 5 and 10 weeks of treatment (FIG. 14).

Conclusions: Compound 2 treatment (10 and 30 mg/kg/day) of male, diet-induced obese mice for up to 10 weeks tended to reduce body weight gain and resulted in a significant and sustained reduction in total plasma cholesterol (>50%), and an amelioration of hyperglycemia (blood glucose lowering of up to 25%). The main effects on cholesterol and glucose were observed within 2 to 3 weeks of drug treatment and were sustained throughout the remainder of the 10-week treatment period. Hepatic steatosis, as assessed by histological analysis of tissue obtained from mice treated with Compound 2 at 30 mg/kg/day for 2, 5 and 10 weeks, was visually improved at 2 weeks. A similar improvement was observed at the 5- and 10-week time points evaluated. Consistent with a reduction in steatosis, the hepatomegaly associated with high-fat feeding was significantly and similarly reduced after 2, 5 and 10 weeks of Compound 2 treatment.

EXAMPLE 5

Compounds 1, 2, 3, and 4 are administered orally, at doses ranging from 0.1 mg/kg to 10 mg/kg, to alpha-glucosidase deficient mice that manifest GSD-2-like hepatic symptoms, including hypercholesterolemia and hyperlipidemia (GAA−/−; see e.g. Raben, N. et al., Mol. Genet. Metab. Sep-Oct; 80(1-2):159-69 (2003)). Blood is drawn from each animal every two days or every 3-4 days. Animals are assessed for their plasma cholesterol levels, total plasma lipid levels, hepatic lipid content, hepatic glycogen content, free glucose levels, Aspartate transaminase (AST) and alanine transaminase (ALT) levels, and thyroid function. Total T4, Total T3, Free T4, Free T3, and Thyroid Stimulating Hormone are assessed. After 14 days, and again after 22 days, data are compiled and subjected to appropriate statistical analyses. After 22 days, animals are sacrificed and their livers are examined for signs of steatosis and fibrosis, as well as histological signs of abnormal glycogen storage. Differences in survival time, where relevant, between treated and untreated animals are assessed.

EXAMPLE 6

Compounds 1, 2, 3, and 4 are administered orally, at doses ranging from 0.1 mg/kg to 10 mg/kg, to glucose-6-phosphatase-α deficient mice that manifest GSD-1-like hepatic symptoms, including hypercholesterolemia and hyperlipidemia (G6pc−/−, G6pc3−/−, or G6pt−/− see e.g. Chou, J. Y. et al., Nat. Rev. Endocrinol. 6(12): 676-688 (2010)). Blood is drawn from each animal every two days or every 3-4 days. Animals are assessed for their plasma cholesterol levels, total plasma lipid levels, hepatic lipid content, hepatic glycogen content, free glucose levels, Aspartate transaminase (AST) and alanine transaminase (ALT) levels, and thyroid function. Total T4, Total T3, Free T4, Free T3, and Thyroid Stimulating Hormone are assessed. After 14 days, and again after 22 days, data are compiled and subjected to appropriate statistical analyses. After 22 days, animals are sacrificed and their livers are examined for signs of steatosis and fibrosis, as well as histological signs of abnormal glycogen storage. Differences in survival time, where relevant, between treated and untreated animals are assessed.

EXAMPLE 7

Compounds 1, 2, 3, and 4 are administered orally, at doses ranging from 0.1 mg/kg to 10 mg/kg, to glucose-6-phosphatase-α deficient mice that manifest GSD-3-like hepatic symptoms, including hypercholesterolemia and hyperlipidemia (Agl−/−, see e.g. Liu, K. M. et al., Mol. Genet. Metabol. 111(4):467-76 (2014)). Blood is drawn from each animal every two days or every 3-4 days. Animals are assessed for their plasma cholesterol levels, total plasma lipid levels, hepatic lipid content, hepatic glycogen content, free glucose levels, Aspartate transaminase (AST) and alanine transaminase (ALT) levels, and thyroid function. Total T4, Total T3, Free T4, Free T3, and Thyroid Stimulating Hormone are assessed. After 14 days, and again after 22 days, data are compiled and subjected to appropriate statistical analyses. After 22 days, animals are sacrificed and their livers are examined for signs of steatosis and fibrosis, as well as histological signs of abnormal glycogen storage. Differences in survival time, where relevant, between treated and untreated animals are assessed.

EXAMPLE 8

Compounds 1, 2, 3, and 4 are administered orally, at doses ranging from 0.1 mg/kg to 10 mg/kg, to liver glycogen phosphorylase deficient mice that manifest GSD-6-like hepatic symptoms, including hypercholesterolemia and hyperlipidemia (Pygl−/−, such as, for example, knockout mouse line No. TL1774 from Taconic Biosciences, Inc.). Blood is drawn from each animal every two days or every 3-4 days. Animals are assessed for their plasma cholesterol levels, total plasma lipid levels, hepatic lipid content, hepatic glycogen content, free glucose levels, Aspartate transaminase (AST) and alanine transaminase (ALT) levels, and thyroid function. Total T4, Total T3, Free T4, Free T3, and Thyroid Stimulating Hormone are assessed. After 14 days, and again after 22 days, data are compiled and subjected to appropriate statistical analyses. After 22 days, animals are sacrificed and their livers are examined for signs of steatosis and fibrosis, as well as histological signs of abnormal glycogen storage. Differences in survival time, where relevant, between treated and untreated animals are assessed.

EXAMPLE 9

Compounds 1, 2, 3, and 4 are administered orally, at doses ranging from 0.1 mg/kg to 10 mg/kg, to phosphofructokinase deficient mice that manifest GSD-7-like hepatic symptoms, including hypercholesterolemia and hyperlipidemia (Pfkm−/−, see, e.g., Garcia M. et al., PLoS Genet. 5(8): e1000615. doi:10.1371/journal.pgen.1000615 (2009)). Blood is drawn from each animal every two days or every 3-4 days. Animals are assessed for their plasma cholesterol levels, total plasma lipid levels, hepatic lipid content, hepatic glycogen content, free glucose levels, Aspartate transaminase (AST) and alanine transaminase (ALT) levels, and thyroid function. Total T4, Total T3, Free T4, Free T3, and Thyroid Stimulating Hormone are assessed. After 14 days, and again after 22 days, data are compiled and subjected to appropriate statistical analyses. After 22 days, animals are sacrificed and their livers are examined for signs of steatosis and fibrosis, as well as histological signs of abnormal glycogen storage. Differences in survival time, where relevant, between treated and untreated animals are assessed.

EXAMPLE 10

Compounds 1, 2, 3, and 4 are administered orally, at doses ranging from 0.1 mg/kg to 10 mg/kg, to phosphorylase kinase deficient mice that manifest GSD-8/9-like hepatic symptoms, including hypercholesterolemia and hyperlipidemia (PhKc−/−, see, e.g., Varsanyi, M. et al., Biochem. Genet. 18(3-4):247-61 (1980)). Blood is drawn from each animal every two days or every 3-4 days. Animals are assessed for their plasma cholesterol levels, total plasma lipid levels, hepatic lipid content, hepatic glycogen content, free glucose levels, Aspartate transaminase (AST) and alanine transaminase (ALT) levels, and thyroid function. Total T4, Total T3, Free T4, Free T3, and Thyroid Stimulating Hormone are assessed. After 14 days, and again after 22 days, data are compiled and subjected to appropriate statistical analyses. After 22 days, animals are sacrificed and their livers are examined for signs of steatosis and fibrosis, as well as histological signs of abnormal glycogen storage. Differences in survival time, where relevant, between treated and untreated animals are assessed.

EXAMPLE 11

Compounds 1, 2, 3, and 4 are administered orally, at doses ranging from 0.1 mg/kg to 10 mg/kg, to phosphorylase kinase deficient mice that manifest GSD-11-like hepatic symptoms, including hypercholesterolemia and hyperlipidemia (Glut2−/−, see, e.g., Bady, I. et al., Diabetes 55(4): 988-995 (2006)). Blood is drawn from each animal every two days or every 3-4 days. Animals are assessed for their plasma cholesterol levels, total plasma lipid levels, hepatic lipid content, hepatic glycogen content, free glucose levels, Aspartate transaminase (AST) and alanine transaminase (ALT) levels, and thyroid function. Total T4, Total T3, Free T4, Free T3, and Thyroid Stimulating Hormone are assessed. After 14 days, and again after 22 days, data are compiled and subjected to appropriate statistical analyses. After 22 days, animals are sacrificed and their livers are examined for signs of steatosis and fibrosis, as well as histological signs of abnormal glycogen storage. Differences in survival time, where relevant, between treated and untreated animals are assessed.

EXAMPLE 12

Compound 2 was tested in a G6PC−/−mouse model of GSD Ia. Daily injection of 0.1 to 0.2 mL 10% dextrose subcutaneously was initiated within 3 days of age for G6PC−/−mice. All G6PC−/−mice continued to receive daily dextrose injections during this time. Blood was collected at time of euthanasia, when tissues were collected. Two groups of 4 G6PC−/−mice (1 group treated with Compound 2, 1 group treated with vehicle) were analyzed to identify statistically significant differences between Compound 2-treated and vehicle-treated controls. We also treated 2 groups of 3 normal (wild type) mice, one with Compound 2 and one with vehicle.

Figure 15:
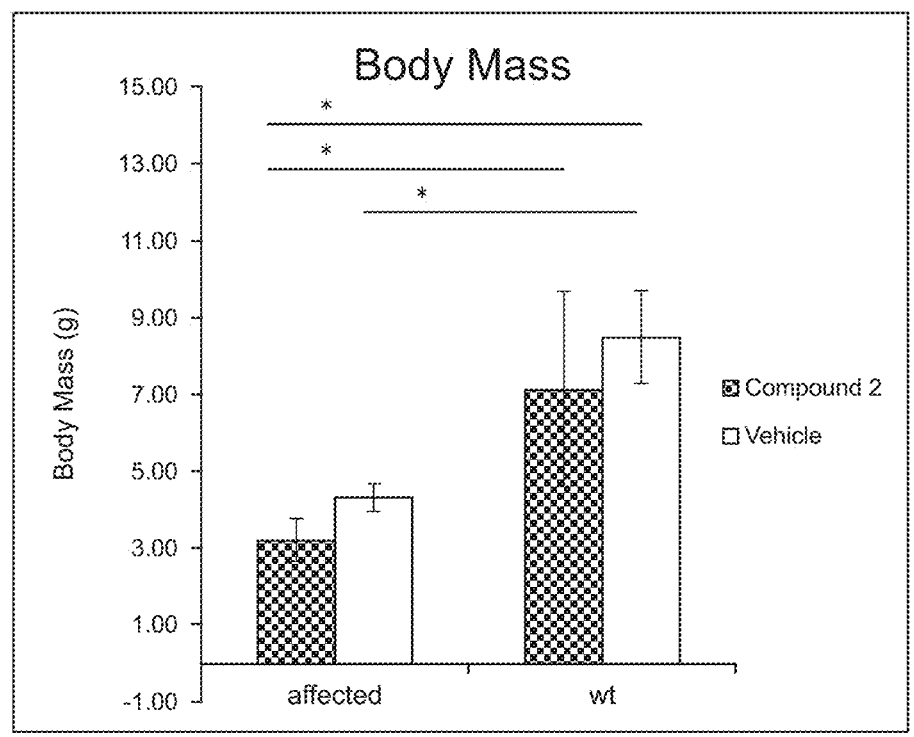
FIG. 15 shows the difference in body mass between Compound 2-treated and Vehicle-treated mice in a G6PC−/− knockout mouse model ("affected") vs wild type mice ("wt").
Figure 16:
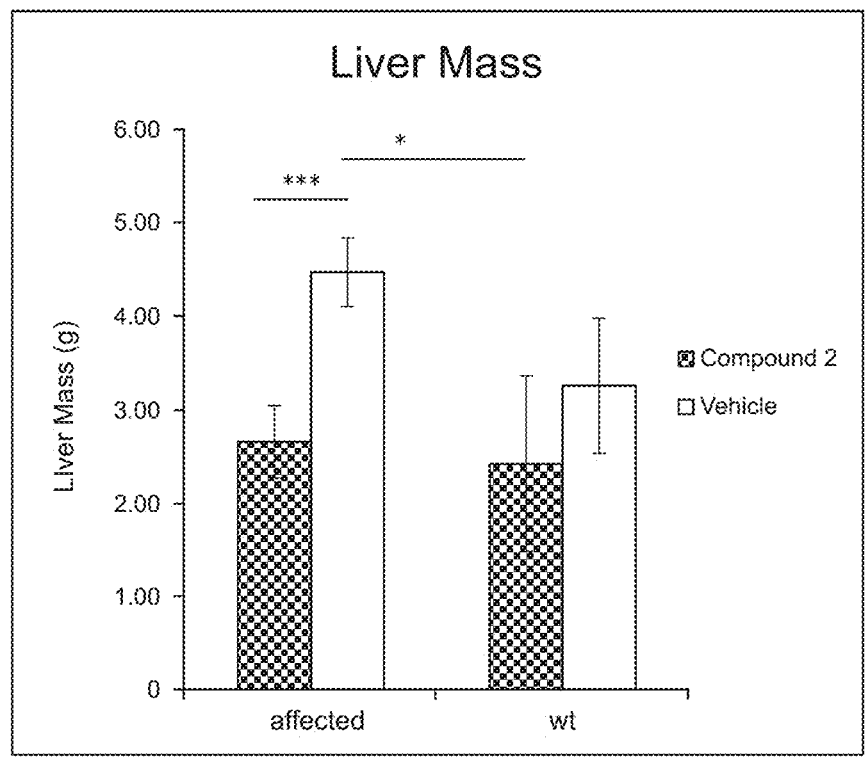
FIG. 16 shows the difference in liver mass between Compound 2-treated and Vehicle-treated mice in a G6PC−/− knockout mouse model ("affected") vs wild type mice ("wt").
Figure 17:
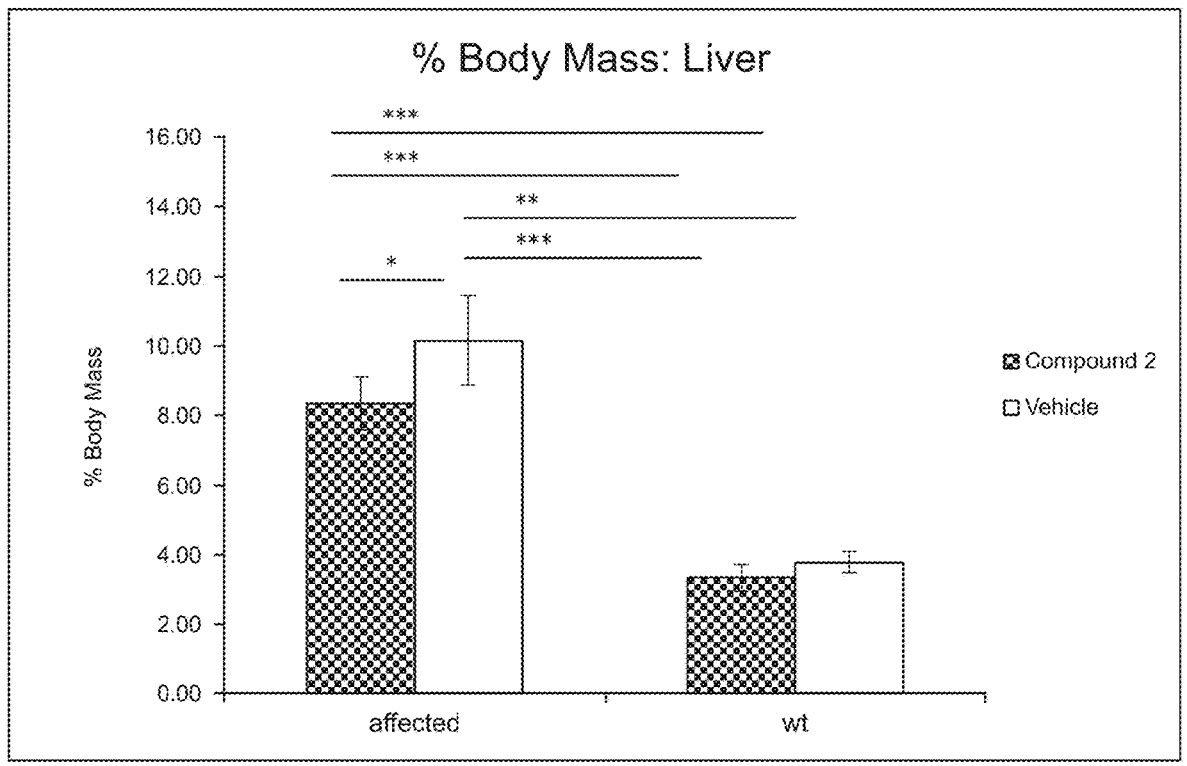
FIG. 17 shows the difference in liver mass as a percentage of body mass between Compound 2-treated and Vehicle-treated mice in a G6PC−/−knockout mouse model ("affected") vs wild type mice ("wt").
Figure 18:
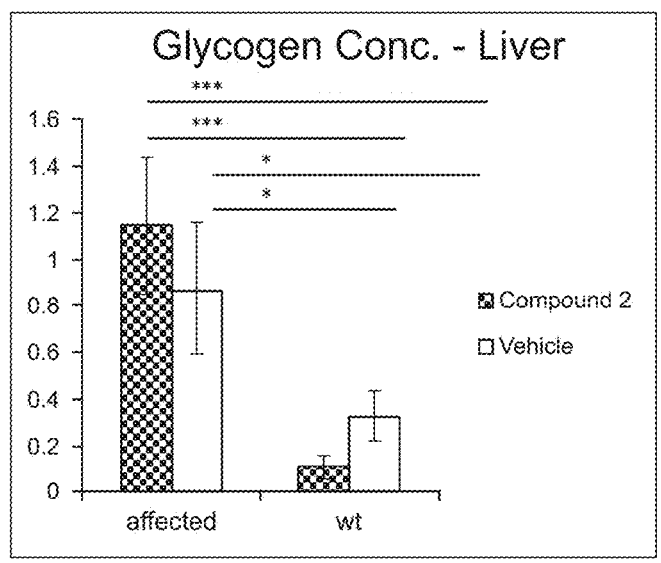
FIG. 18 shows the difference in liver glycogen concentration between Compound 2-treated and Vehicle-treated mice in a G6PC−/−knockout mouse model ("affected") vs wild type mice ("wt").
Figure 19:
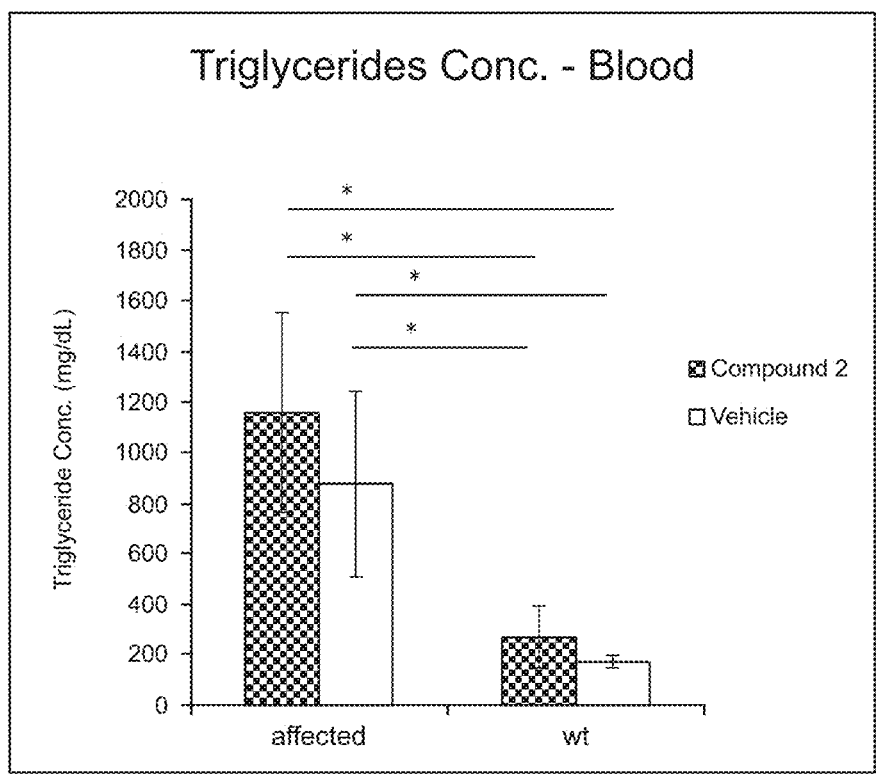
FIG. 19 shows the difference in serum triglyceride concentration between Compound 2-treated and Vehicle-treated mice in a G6PC−/−knockout mouse model ("affected") vs wild type mice ("wt").
Figure 20:
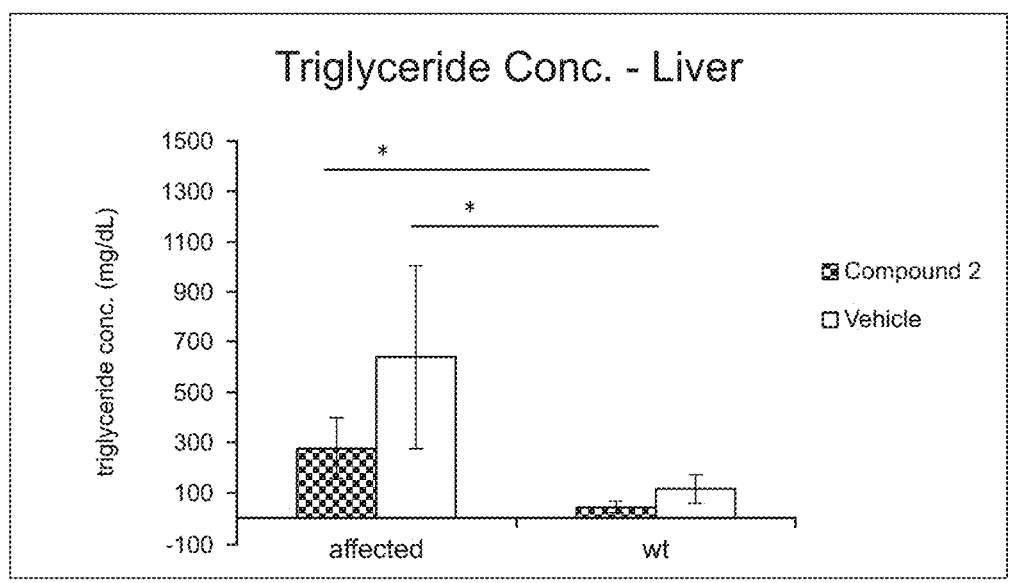
FIG. 20 shows the difference in liver triglyceride concentration between Compound 2-treated and Vehicle-treated mice in a G6PC−/−knockout mouse model ("affected") vs wild type mice ("wt").
Figure 21:
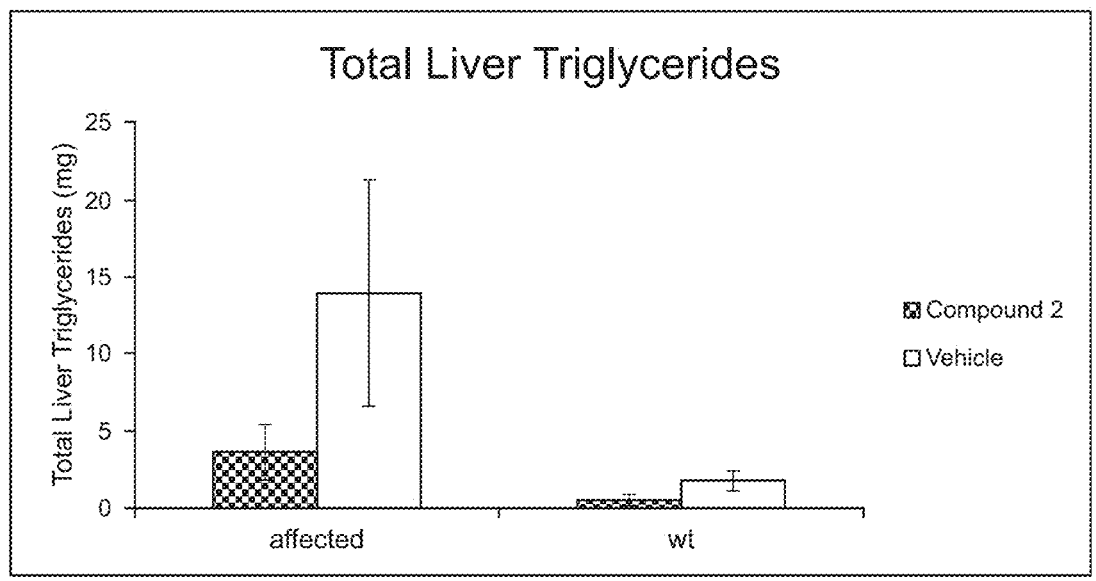
FIG. 21 shows the difference in total liver triglycerides between Compound 2-treated and Vehicle-treated mice in a G6PC−/−knockout mouse model ("affected") vs wild type mice ("wt").

Initially the GSD Ia mice were treated with Compound 2 from 5 to 10 days of age. Body mass, liver mass, liver glycogen concentration, liver triglycerides, fasting serum glucose, fasting serum triglycerides, and GSD-related cell signaling pathways were examined. Similarly, groups of GSD Ia mice were treated with vehicle for 5 days to serve as mock-treated controls for all assays. Groups of 3-4 mice were evaluated. GSD Ia mice were treated for >7 days to assess survival and longer-term effects of Compound 2 as described above (GSD Ia mice rarely survive >12 days of life without a therapeutic intervention). Metabolomic analysis of hepatic extracts were performed as described (Sinha, Farah et al. (2013), Hepatology 59(4):1366-80). Acylcarnitine and amino acid profiling were employed to detect any changes related to increased lipolysis and fatty acid beta-oxidation as described by Sinha et al. (Sinha, Farah et al. (2013), Hepatology 59(4):1366-80). Mice treated with Compound 2 showed reduced body mass (FIG. 15), reduced liver mass (FIG. 16), reduced liver mass as a percentage of body mass (FIG. 17), reduced liver triglyceride concentrations (FIG. 20), and reduced total liver triglycerides (FIG. 21) compared to vehicle-treated (mock treated) controls. These effects were seen in both wild type (wt) and G6PC−/−mice, though the effects on liver mass and liver triglycerides were more pronounced in G6PC−/−mice than in wt. Mice treated with Compound 2 showed somewhat enhanced serum triglycerides compared to vehicle-treated controls, in both the G6PC−/− and wt backgrounds (FIG. 19). G6PC−/−mice treated with Compound 2 showed somewhat enhanced liver glycogen levels relative to vehicle-treated controls, while wt mice treated with Compound 2 showed significantly reduced liver glycogen levels relative to vehicle-treated controls (FIG. 18). Mean liver triglyceride content was reduced by more than 60% in Compound 2-treated animals relative to vehicle-treated control animals, while average liver weight was reduced by more than 30% vs. controls. Importantly, average liver weight as a percent of total body weight also declined by approximately 20% in treated vs. control animals. Further, treatment with Compound 2 led to statistically significant reductions in key metabolic markers of GSD Ia.

EXAMPLE 13

The objective of this study was to determine the ability of Compound 2, a small molecule prodrug of a potent thyroid hormone beta receptor (TBR) agonist, to reduce hepatic steatosis and other metabolic derangements in the glucose-6-phosphatase catalytic subunit knockout (G6pc−/−) mouse model of glycogen storage disease type Ia (GSD Ia).

Mice were treated with Compound 2 or with vehicle, using 4 groups of 6-7 mice: G6pc−/−mice receiving Compound 2, G6pc−/−mice receiving vehicle, Wt mice receiving Compound 2, and WT mice receiving vehicle. Daily injection of 0.1 to 0.2 mL 10% dextrose subcutaneously was initiated at 3 days of age for all mice, and all mice continued to receive daily dextrose injections throughout drug or vehicle treatment. Dextrose was not administered on the day of tissue collection. Mice were treated daily with Compound 2 or with vehicle, respectively, from 5 to 8 days of age. Mice were sacrificed on Day 9, and blood and tissues were collected. The fasting serum glucose and triglycerides, hepatic lipid and glycogen content, and GSD-related cell signaling pathways were examined.

Figure 22:
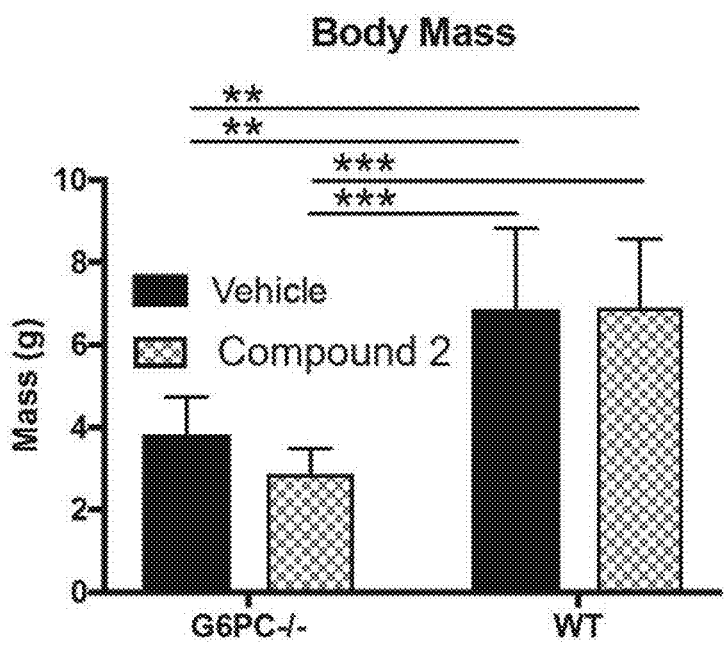
FIG. 22 shows that there was no significant difference between the body masses of Compound 2-treated and Vehicle-treated mice in a G6PC−/−knockout mouse model (G6PC−/−) vs wild type mice ("wt"). However, all G6pc−/− mice had significantly stunted growth compared to WT mice.
Figure 23A:
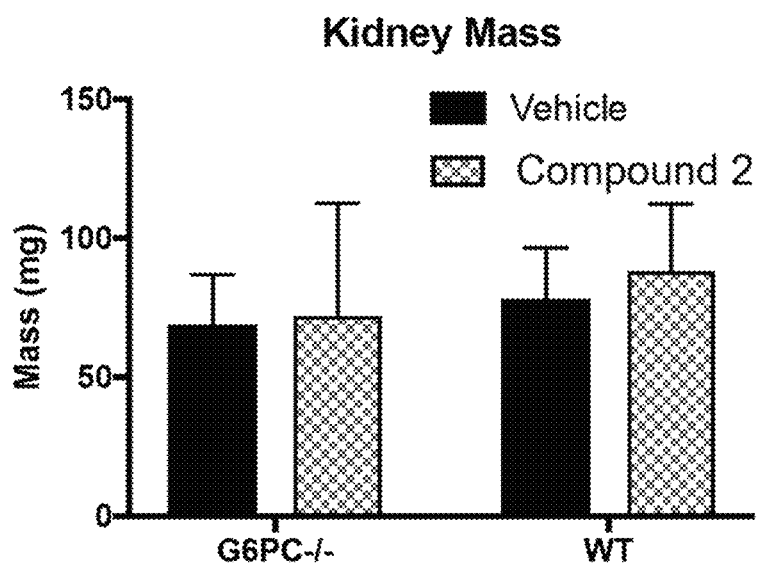
FIG. 23 shows that kidney mass is not affected by Compound 2 treatment. (A) There is no significant change in absolute kidney mass across all four treatment groups shown. (B) Compound 2 treatment of G6pc−/−mice increases kidney mass as a percentage of total body mass compared to WT kidneys, however, the difference between the kidney masses in G6pc−/−mice treated with Compound 2 vs vehicle is not significant. Mean+/− s.d. shown. *=p<0.05, =p<0.01, *=p<0.001, ****=p<0.0001 from ANOVA.
Figure 23B:
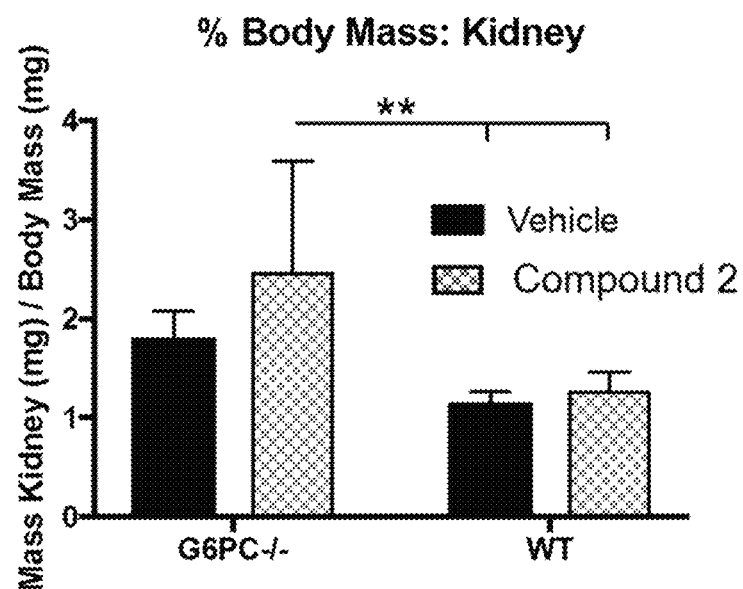
Figure 24:
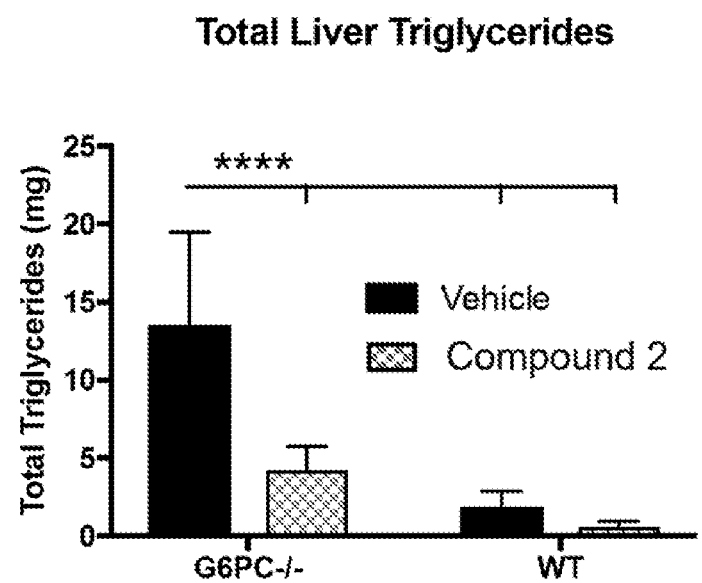
FIG. 24 shows that Compound 2 treatment significantly decreases total liver triglycerides. Total liver triglycerides were elevated in vehicle treated G6pc−/−mice compared to WT controls. This increase was attenuated in G6pc−/−mice upon Compound 2 treatment, which significantly reduced the total liver triglycerides to within levels sen in vehicle-treated WT control levels. Mean+/− s.d. shown. *=p<0.05, =p<0.01, *=p<0.001, ****=p<0.0001 from ANOVA.
Figure 25A:
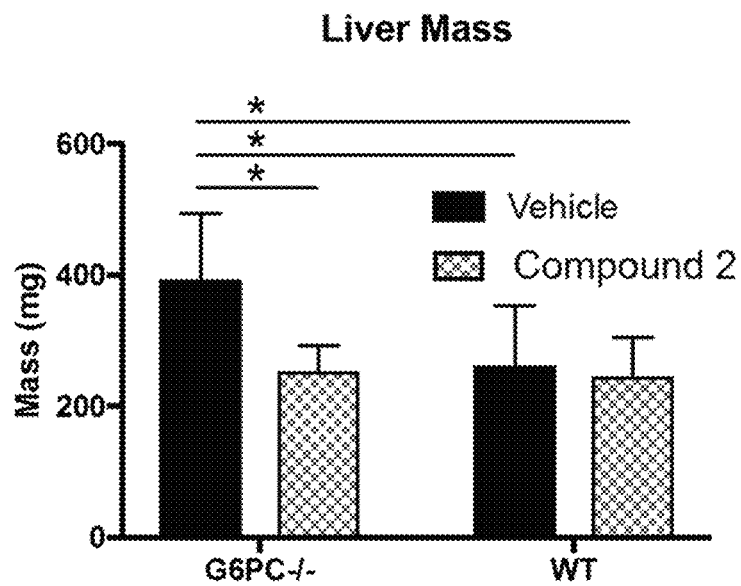
FIG. 25 shows that Compound 2 lowers liver mass in G6pc−/−mice. (A) G6pc−/−mice treated with Compound 2 had significantly smaller livers than vehicle controls. (B) G6pc−/−mice treated with Compound 2 had significantly smaller livers as a proportion of body mass than vehicle controls. Mean+/− s.d. shown. *=p<0.05, =p<0.01, *=p<0.001, ****=p<0.0001 from ANOVA.
Figure 25B:
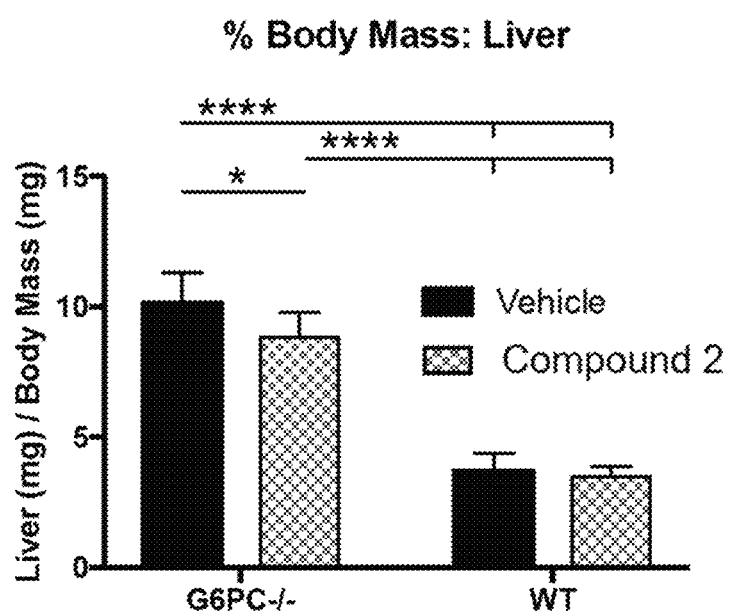
Figure 26:
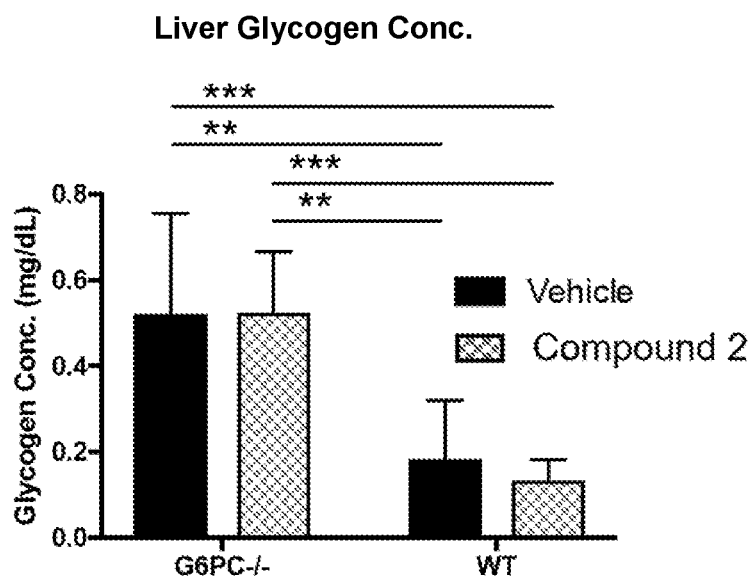
FIG. 26 shows that glycogen concentration in the livers of G6pc−/−mice did not change with Compound 2 treatment. Both G6pc−/−groups had significantly higher liver glycogen concentration than WT controls. Mean+/− s.d. shown. *=p<0.05, =p<0.01, *=p<0.001, ****=p<0.0001 from ANOVA.
Figure 27:
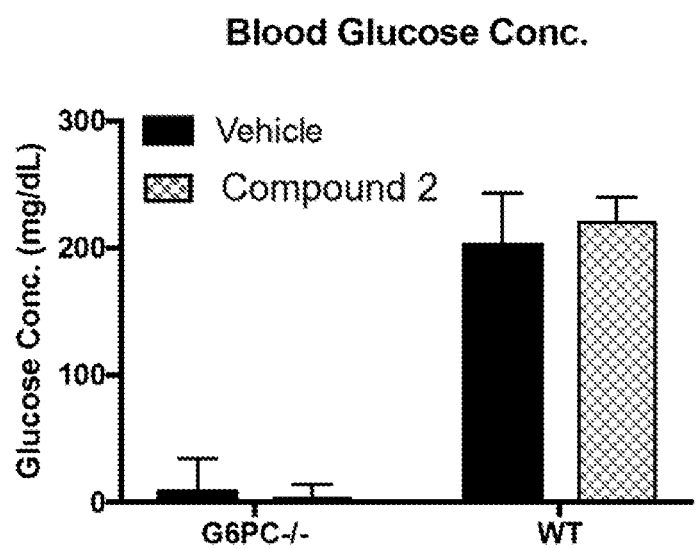
FIG. 27 shows the effect of Compound 2 on Blood Glucose concentration. All blood glucose measurements for G6pc−/−mice, aside from one vehicle treated mouse, were below the lower detection limit (20 mg/dL) of the glucometer instrument, therefore statistics were not able to be performed on this data set. Mean+/− s.d. shown. *=p<0.05, =p<0.01, *=p<0.001, ****=p<0.0001 from ANOVA.
Figure 28:
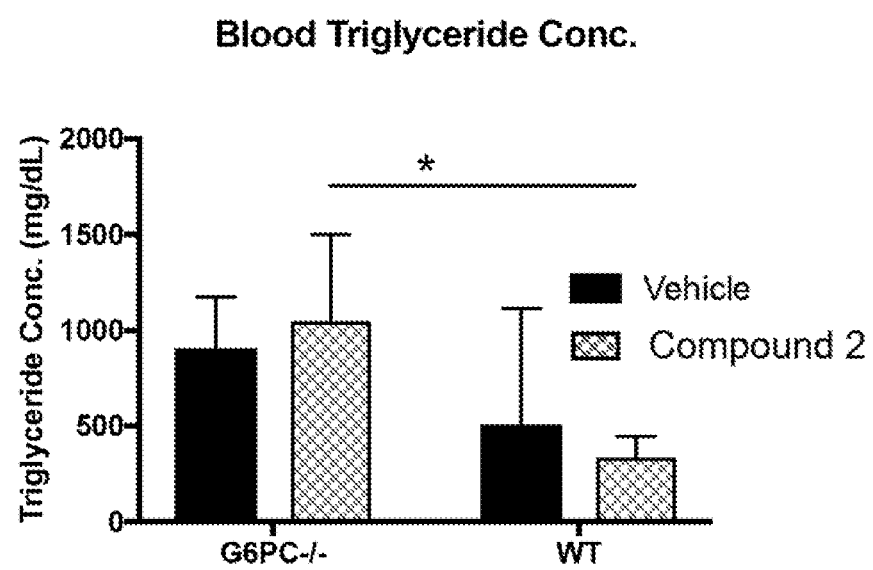
FIG. 28 shows the effect of Compound 2 on Serum triglyceride concentration. Serum triglyceride concentration was not significantly different between Compound 2 and vehicle treated G6pc−/−groups; however, there was a significant difference between G6pc−/− and WT groups treated with Compound 2. Mean+/− s.d. shown. *=p<0.05, =p<0.01, *=p<0.001, ****=p<0.0001 from ANOVA.

Body Mass and Kidney Mass were not affected by treatment with Compound 2 (FIGS. 22 and 23). Compared with vehicle-treated controls, mean total liver triglycerides in G6pc−/−mice were significantly reduced by 69.0% from 13.550 mg to 4.210 mg following 4 days of drug treatment (p<0.0001) (FIG. 24). Similarly, mean liver weights were significantly reduced by over 30% from 393.55 mg to 253.11 mg in treated vs. control G6pc−/−cohorts (p<0.05) (FIG. 25). Drug treatment also produced a decrease in mean serum triglyceride concentration by 54.0% in G6pc−/−mice, from 729.59 mg/dL to 336.58 mg/dL. Under the dosing parameters chosen, there were no significant changes in liver glycogen concentration, serum glucose concentration, or serum triglyceride concentration (FIGS. 26-28). These data suggest Compound 2 reduces hepatic steatosis in the G6pc−/−mouse model of GSD Ia.

The above-described embodiments have been provided by way of example, and the methods and cells described herein are not limited to these examples. Multiple variations and modification to the disclosed embodiments will occur, to the extent not mutually exclusive, to those skilled in the art upon consideration of the foregoing description. Additionally, other combinations, omissions, substitutions and modifications will be apparent to the skilled artisan in view of the disclosure herein. Accordingly, the methods and compositions disclosed herein are not intended to be limited by the disclosed embodiments, but are to be defined by reference to the appended claims. Those skilled in the art will recognize, or be able to ascertain using no more than routine experimentation, many equivalents to the specific embodiments of the methods and cells described herein. Such equivalents are intended to be encompassed by the following claims.

What is claimed is:

1. A method of treating glycogen storage disease Ia (GSD-Ia), comprising administering to a subject in need thereof a compound having the structure:

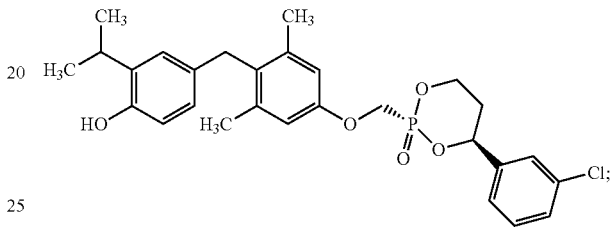

or a pharmaceutically acceptable salt thereof.

2. The method of claim 1 wherein administration of said compound results in the amelioration a glycogen storage defect.

3. The method of claim 1 wherein administration of said compound leads to a reduction in serum lipid or serum cholesterol levels.

4. The method of claim 1 wherein administration of said compound leads to the amelioration of hepatic steatosis, hypercholesterolemia, or hepatic inflammation associated with a glycogen storage disease.

5. The method of claim 1 wherein said glycogen storage disease Ia is associated with cardiomegaly, hepatomegaly, liver steatosis, hyperlipidemia, hypercholesterolemia, increased ALT, increased AST, increased serum triglycerides, liver fibrosis, cirrhosis, hepatocellular adenoma, or hepatocellular carcinoma.

6. The method of claim 1 further comprising administration of a second therapeutic agent.

7. The method of claim 6 wherein the second therapeutic agent is selected from the group consisting of a starch, a sugar, an amino acid, a peptide, an enzyme, and a gene therapy, or any combination thereof.

8. The method of claim 6 wherein the second therapeutic agent is selected from the group consisting of corn starch, potato starch, wheat starch, vegetable starch, and cassava, or any combination thereof.

9. The method of claim 6 wherein the second therapeutic agent comprises glucose, galactose, fructose, sucrose, maltose, lactose, arabinose, or another sugar, or any combination thereof.

10. The method of claim 6 wherein the second therapeutic agent is selected from the group consisting of alglucosidase alfa, a glucose-6-phosphatase, a debranching enzyme, a glycogen synthase, a glucose-6-phosphatase translocase, a phosphatase translocase, an alpha-1-4-glucosidase, an amylo-1-6-glucosidase, an amylo-1,4-to-1,6-transglucosidase, a glycogen phosphorylase, a phosphofructokinase, a cyclic-3',5' AMP-dependent kinase, a type 2 glucose transporter, and an aldolase A, or any combination thereof.

11. The method of claim 6 wherein the second therapeutic agent is selected from the group consisting of an insulin, an insulin-like peptide, a glucagon, and a glucagon-like peptide, or any combination thereof.

12. The method of claim 1 wherein said compound is administered in association with a liver, kidney, or bone marrow transplant.

13. The method of claim 1 wherein administration of said compound leads to reductions in body mass, liver mass, liver mass as a percentage of body mass, or liver triglyceride levels.

* * * * *